(12) United States Patent
Cha et al.

(10) Patent No.: US 10,981,876 B2
(45) Date of Patent: Apr. 20, 2021

(54) SPIRO COMPOUND AND ORGANIC LIGHT EMITTING ELEMENT COMPRISING SAME

(71) Applicant: LG Chem, Ltd., Seoul (KR)

(72) Inventors: Yongbum Cha, Daejeon (KR); Jin Joo Kim, Daejeon (KR); Sang Duk Suh, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 15/556,074

(22) PCT Filed: Sep. 30, 2016

(86) PCT No.: PCT/KR2016/011023
§ 371 (c)(1),
(2) Date: Sep. 6, 2017

(87) PCT Pub. No.: WO2017/057976
PCT Pub. Date: Apr. 6, 2017

(65) Prior Publication Data
US 2018/0265477 A1    Sep. 20, 2018

(30) Foreign Application Priority Data

Sep. 30, 2015   (KR) .................. 10-2015-0138092

(51) Int. Cl.
*C07D 219/02*   (2006.01)
*H01L 51/00*   (2006.01)
(Continued)

(52) U.S. Cl.
CPC ......... *C07D 219/02* (2013.01); *C07D 401/04* (2013.01); *C07D 401/10* (2013.01);
(Continued)

(58) Field of Classification Search
CPC .. C07D 219/02; C07D 401/04; C07D 401/10; C07D 409/04; C07D 471/04;
(Continued)

(56) References Cited

U.S. PATENT DOCUMENTS

2007/0247059 A1   10/2007   Cho et al.
2007/0292715 A1   12/2007   Yoon et al.
(Continued)

FOREIGN PATENT DOCUMENTS

| CN | 104892578 A | 9/2015 |
|---|---|---|
| JP | 2008510800 A | 4/2008 |

(Continued)

OTHER PUBLICATIONS

Romain, M., Tondelier, D., Geffroy, B., Jeannin, O., Jacques, E., Rault-Berthelot, J. and Poriel, C. (2015), Donor/Acceptor Dihydroindeno[1,2-a ]fluorene and Dihydroindeno[2,1-b ]fluorene: Towards New Families of Organic Semiconductors. Chem. Eur. J., 21: 9426-9439. doi:10.1002/chem.201500336 (Year: 2015).*

(Continued)

*Primary Examiner* — Dylan C Kershner
*Assistant Examiner* — Elizabeth M. Dahlburg
(74) *Attorney, Agent, or Firm* — Lerner, David, Littenberg, Krumholz & Mentlik, LLP

(57) ABSTRACT

The present specification provides a spiro structured compound represented by the following Chemical Formula 1 and an organic light emitting device including the same:

(Continued)

[Chemical Formula 1]

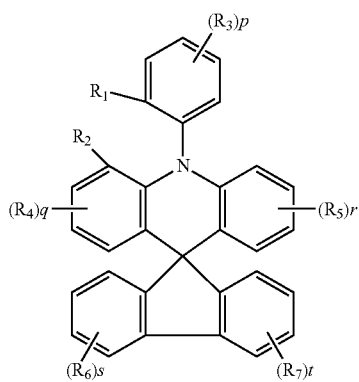

wherein $L_1$, n, $Ar_1$, $R_1$ to $R_7$, p, q, r, s, and t are defined herein.

18 Claims, 1 Drawing Sheet

(51) Int. Cl.
*H01L 51/50* (2006.01)
*C09K 11/06* (2006.01)
*C07D 401/10* (2006.01)
*C07D 401/04* (2006.01)
*C07D 409/04* (2006.01)
*C07D 471/04* (2006.01)

(52) U.S. Cl.
CPC ......... *C07D 409/04* (2013.01); *C07D 471/04* (2013.01); *C09K 11/06* (2013.01); *H01L 51/00* (2013.01); *H01L 51/0052* (2013.01); *H01L 51/0072* (2013.01); *H01L 51/50* (2013.01); *H01L 51/5056* (2013.01); *H01L 51/5096* (2013.01)

(58) Field of Classification Search
CPC .. C07D 219/04; C07D 219/06; C07D 219/08; C07D 405/04; C07D 405/10; C07D 409/10; C07D 471/02; C07D 471/10; H01L 51/0072; H01L 51/00; H01L 51/0052; H01L 51/50; H01L 51/5056; H01L 51/5096; H01L 51/5048; H01L 51/5052; H01L 51/506; H01L 51/5064; H01L 51/5088; C09K 11/06
See application file for complete search history.

(56) References Cited

U.S. PATENT DOCUMENTS

| | | |
|---|---|---|
| 2008/0093982 A1 | 4/2008 | Cho et al. |
| 2008/0303434 A1* | 12/2008 | Cho ............... C07D 221/20 313/506 |
| 2009/0045721 A1 | 2/2009 | Cho et al. |
| 2011/0278549 A1 | 11/2011 | Kim et al. |
| 2014/0174538 A1 | 6/2014 | Park et al. |
| 2014/0209884 A1 | 7/2014 | Park et al. |
| 2015/0200372 A1 | 7/2015 | Park et al. |
| 2015/0218163 A1 | 8/2015 | Park et al. |
| 2015/0259347 A1 | 9/2015 | Park et al. |

FOREIGN PATENT DOCUMENTS

| | | |
|---|---|---|
| JP | 2008510801 A | 4/2008 |
| JP | 2008511160 A | 4/2008 |
| JP | 2015522523 A | 8/2015 |
| KR | 20000051826 A | 8/2000 |
| KR | 20060051619 A | 5/2006 |
| KR | 20130142064 A | 12/2013 |
| KR | 20140020208 A | 2/2014 |
| KR | 20140045266 A | 4/2014 |
| KR | 20150010016 A | 1/2015 |
| WO | 2014058123 A1 | 4/2014 |
| WO | 2014104704 A1 | 7/2014 |
| WO | 2014175627 A1 | 10/2014 |
| WO | 2015009076 A1 | 1/2015 |

OTHER PUBLICATIONS

Romain, M., Tondelier, D., Geffroy, B., Jeannin, O., Jacques, E., Rault-Berthelot, J. and Poriel, C. (2015), Donor/Acceptor Dihydroindeno[1,2-a ]fluorene and Dihydroindeno[2,1-b ]fluorene: Towards New Families of Organic Semiconductors. Chem. Eur. J., 21: 9426-9439. Supporting Information (Year: 2015).*
International Search Report for Application No. PCT/KR2016/011023 dated Jan. 10, 2017.
Extended European Search Report including Written Opinion for Application No. EP16852122.7 dated Mar. 4, 2019.
Maxime Romain et al: "Donor/Acceptor Dihydroindeno[1,2-a ]fluorene and Dihydroindeno[2,1-b]fluorene: Towards New Familes of Organic Semiconductors", Chemistry—A European Journal, Jun. 22, 2015, vol. 21, No. 26, pp. 9426-9439, XP055495548.
Shou-Cheng Dong et al: "Spiro-annulated triarylamine-based hosts incorporating dibenzothiophene for highly efficient single-emitting layer white phosphorescent organic light-emitting diodes", Journal of Materials Chemistry C, Jan. 1, 2013, vol. 1, No. 40, pp. 6575-6584, XP055192026.

* cited by examiner

SPIRO COMPOUND AND ORGANIC LIGHT EMITTING ELEMENT COMPRISING SAME

TECHNICAL FIELD

The present application is a national phase entry under 35 U.S.C. § 371 of International Application No. PCT/KR2016/011023 filed Sep. 30, 2016, published in Korean, which claims priority from Korean Patent Application No. 10-2015-0138092, filed Sep. 30, 2015, all of which are incorporated herein by reference.

The present specification relates to a spiro structured compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826

DETAILED DESCRIPTION OF THE INVENTION

Technical Problem

The present specification describes a spiro structured compound and an organic light emitting device including the same.

Technical Solution

An exemplary embodiment of the present specification provides a compound represented by the following Chemical Formula 1:

[Chemical Formula 1]

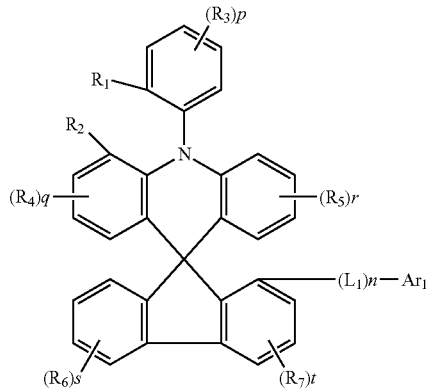

In Chemical Formula 1, $L_1$ is a direct bond; a substituted or unsubstituted arylene group; or a substituted or unsubstituted heteroarylene, n is an integer of 0 to 2, and when n is 2 or more, $L_1$'s are the same as or different from each other, and $Ar_1$ and $R_1$ to $R_7$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or may combine with an adjacent group to form a ring, p, s, and r are each an integer of 0 to 4, q and t are an integer of 0 to 3, and when p, q, r, s, and t are each 2 or more, groups in the parenthesis are the same as or different from each other.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound described in the present specification may be used as a material for an organic material layer of an organic light emitting device. The compound according to at least one exemplary embodiment of the present specification may improve the efficiency, achieve low driving voltage and/or improve lifetime characteristics in the organic light emitting device. In particular, the compound described in the present specification may be used as a material for hole injection, hole transport, hole injection and hole transport, light emission, electron transport, electron blocking, or electron injection. In addition, the compound described in the present specification may be used as a material for an organic solar cell or an organic transistor in addition to the organic light emitting device.

MODE FOR INVENTION

Figure 1:
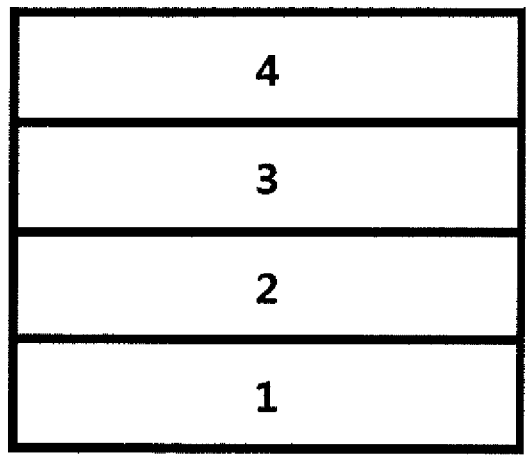
FIG. 1 illustrates an example of an organic light emitting device composed of a substrate 1, a positive electrode 2, a light emitting layer 3, and a negative electrode 4.

Hereinafter, the present specification will be described in more detail.

Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamino group; an aralkylamino group; a heteroarylamino group; an arylamino group; an arylphosphine group; and a heterocyclic group, or being unsubstituted or substituted with a substituent to which two or more substituents among the substituents exemplified above are linked. For example, "the substituent to which two or more substituents are linked" may be an aryl group substituted with a heteroaryl group.

In the present specification, the number of carbon atoms of a carbonyl group is not particularly limited, but is preferably 1 to 40. Specifically, the carbonyl group may be a compound having the following structures, but is not limited thereto.

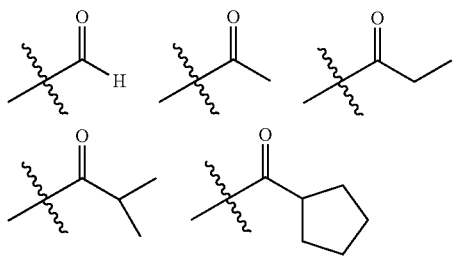

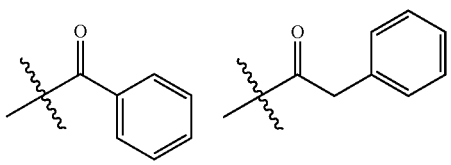

In the present specification, for an ester group, the oxygen of the ester group may be substituted with a straight-chained, branch-chained, or cyclic alkyl group having 1 to 25 carbon atoms, or an aryl group having 6 to 25 carbon atoms. Specifically, the ester group may be a compound having the following structural formulae, but is not limited thereto.

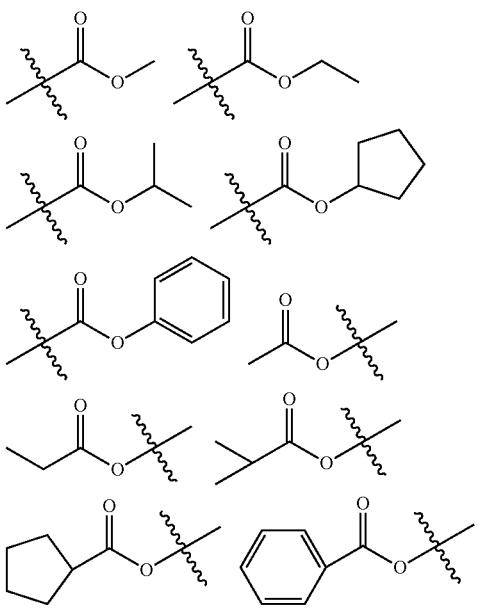

In the present specification, the number of carbon atoms of an imide group is not particularly limited, but is preferably 1 to 25. Specifically, the imide group may be a compound having the following structures, but is not limited thereto.

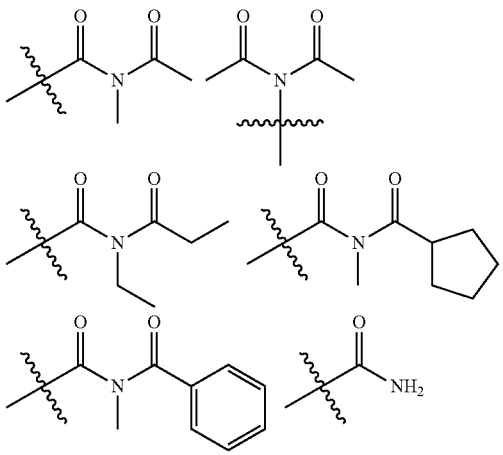

-continued

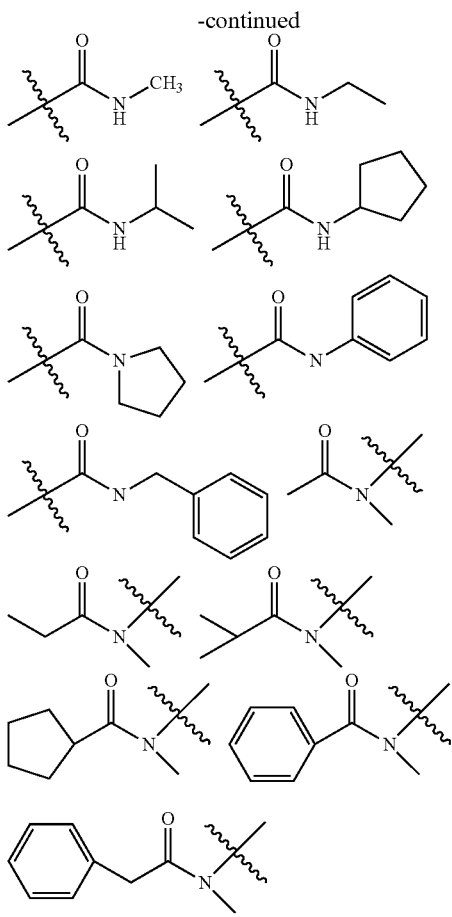

In the present specification, a silyl group may be represented by a chemical formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a chemical formula of —BRR', and R and R' may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, examples of a halogen group include fluorine, chlorine, bromine or iodine.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to still yet another exemplary embodiment, the number of carbon atoms of the cycloalkyl group is 3 to 20. According to a further exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group is not particularly limited, but has preferably 1 to 40 carbon atoms. According to an exemplary embodiment, the number of carbon atoms of the alkoxy group is 1 to 10. According to another exemplary embodiment, the number of carbon atoms of the alkoxy group is 1 to 6. Specific examples of the alkoxy group include a methoxy group, an ethoxy group, a propoxy group, an isobutyloxy group, a sec-butyloxy group, a pentyloxy group, an iso-amyloxy group, a hexyloxy group, and the like, but are not limited thereto.

In the present specification, the number of carbon atoms of an amino group is not particularly limited, but is preferably 1 to 30. Specific examples of the amino group include a methylamino group, a dimethylamino group, an ethylamino group, a diethylamino group, a phenylamino group, a naphthylamino group, a biphenylamino group, an anthracenylamino group, a 9-methyl-anthracenylamino group, a diphenylamino group, a phenylnaphthylamino group, a ditolylamino group, a phenyltolylamino group, a triphenylamino group, and the like, but are not limited thereto.

In the present specification, examples of an arylamino group include a substituted or unsubstituted monoarylamino group, a substituted or unsubstituted diarylamino group, or a substituted or unsubstituted triarylamino group. The aryl group in the arylamino group may be a monocyclic aryl group, and may be a polycyclic aryl group. The arylamino group including two or more aryl groups may include a monocyclic aryl group, a polycyclic aryl group, or both a monocyclic aryl group and a polycyclic aryl group. Specific examples of the arylamino group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamino group, a phenylnaphthylamino group, a ditolylamino group, a phenyltolylamino group, carbazole, a triphenylamino group, and the like, but are not limited thereto.

In the present specification, examples of a heteroarylamino group include a substituted or unsubstituted monoheteroarylamino group, a substituted or unsubstituted diheteroarylamino group, or a substituted or unsubstituted triheteroarylamino group. The heteroaryl group in the heteroarylamino group may be a monocyclic heterocyclic group, and may be a polycyclic heterocyclic group. The heteroarylamino group including two or more heterocyclic groups may include a monocyclic heterocyclic group, a polycyclic heterocyclic group, or both a monocyclic heterocyclic group and a polycyclic heterocyclic group.

In the present specification, an arylheteroarylamino group means an amino group substituted with an aryl group and a heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a triphenylene group, and the like, but are not limited thereto.

In the present specification, a fluorenyl group may be substituted, and two substituents may combine with each other to form a spiro structure.

When the fluorenyl group is substituted, the fluorenyl group may be

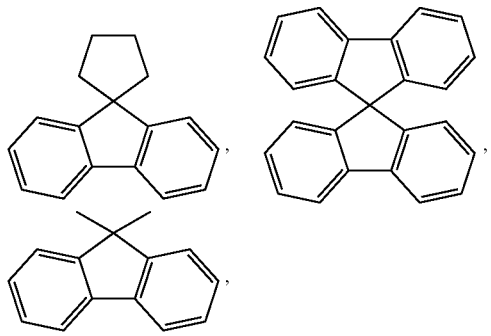

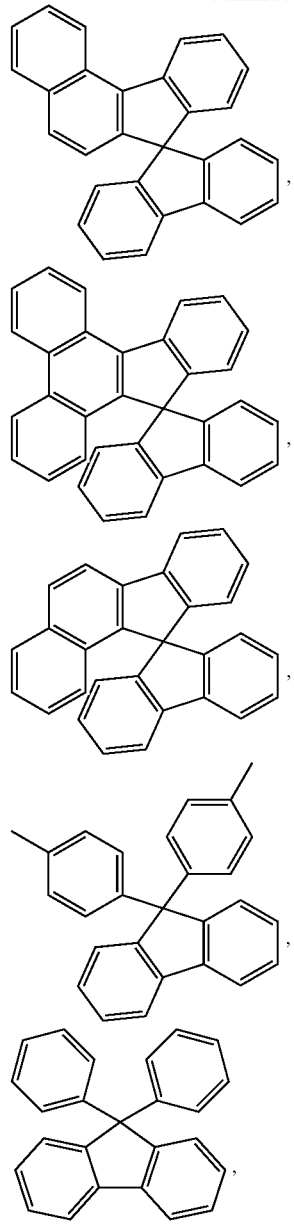

and the like. However, the fluorenyl group is not limited thereto.

In the present specification, a heterocyclic group is a heterocyclic group including one or more of N, O, S, Si, and Se as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the above-described description on the heterocyclic group may be applied to a heteroaryl group except for an aromatic heteroaryl group.

In the present specification, the above-described description on the aryl group may be applied to an aryl group in an aryloxy group, an arylthioxy group, an arylsulfoxy group, an arylphosphine group, an aralkyl group, an aralkylamino group, an aralkenyl group, an alkylaryl group, an arylamino group, and an arylheteroarylamino group.

In the present specification, the above-described description on the alkyl group may be applied to an alkyl group in an alkylthioxy group, an alkylsulfoxy group, an aralkyl group, an aralkylamino group, an alkylaryl group, and an alkylamino group.

In the present specification, the above-described description on the heterocyclic group may be applied to a heteroaryl group in a heteroaryl group, a heteroarylamino group, and an arylheteroarylamino group.

In the present specification, the above-described description on the alkenyl group may be applied to an alkenyl group in an aralkenyl group.

In the present specification, the above-described description on the aryl group may be applied to an arylene except for a divalent arylene group.

In the present specification, the above-described description on the heterocyclic group may be applied to a heteroarylene except for a divalent heteroarylene group.

In the present specification, combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof. The aliphatic hydrocarbon ring is a ring which is not an aromatic ring, and is a ring composed of only carbon and hydrogen atoms. Examples of the aromatic hydrocarbon ring include benzene, naphthalene, anthracene, and the like, but are not limited thereto. The aliphatic hetero ring is an aliphatic ring including one or more heteroatoms. The aromatic hetero ring is an aromatic ring including one or more heteroatoms. The hetero ring may include O, S, Se, N, or Si as a heteroatom. The aliphatic hydrocarbon ring, the aromatic hydrocarbon ring, the aliphatic hetero ring, and the aromatic hetero ring may be monocyclic or polycyclic.

According to an exemplary embodiment of the present specification, Chemical Formula 1 may be represented by the following Chemical Formula 2 or 3.

[Chemical Formula 2]

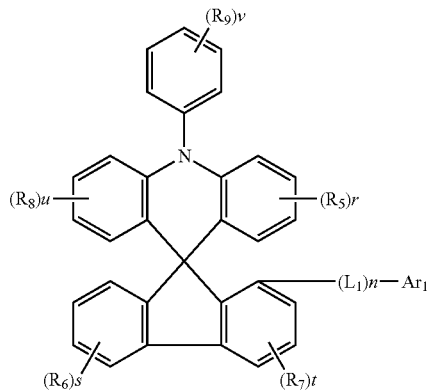

In Chemical Formula 2, $R_5$ to $R_7$, r, s, t, $L_1$, n, and $Ar_1$ are the same as those defined in Chemical Formula 1, $R_8$ and $R_9$ are the same as or different from each other, and are the same as the definitions of $R_1$ to $R_7$ of Chemical Formula 1, u is an integer of 1 to 4, v is an integer of 1 to 5, and when u and v are each 2 or more, groups in the parenthesis are the same as or different from each other.

[Chemical Formula 3]

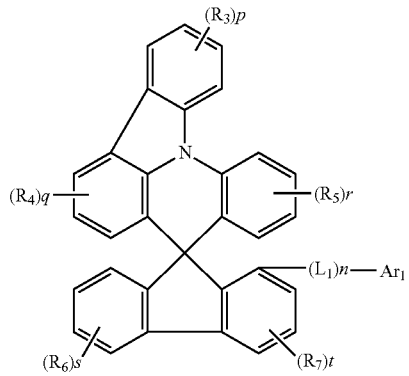

In Chemical Formula 3, $R_3$ to $R_7$, p, q, r, s, t, $L_1$, n, and $Ar_1$ are the same as those defined in Chemical Formula 1.

According to an exemplary embodiment of the present invention, in Chemical Formula 1, $R_1$ and $R_2$ are hydrogen.

According to an exemplary embodiment of the present invention, in Chemical Formulae 1 to 3, $Ar_1$ is a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combines with an adjacent group to form a ring, and when these groups are substituted, the substituent is hydrogen, deuterium, a halogen group, a nitrile group, a silyl group, an alkyl group, an alkylamine group, an aralkylamine group, a heteroarylamine group, an arylamine group, an arylheteroarylamine group, an arylphosphine group, a phosphine oxide group, an aryl group, or a heterocyclic group.

According to an exemplary embodiment of the present invention, in Chemical Formulae 1 to 3, $Ar_1$ is a substituted or unsubstituted aryl group; a substituted or unsubstituted heterocyclic group; a substituted or unsubstituted arylamino group; a substituted or unsubstituted arylphosphine group; or a substituted or unsubstituted silyl group.

According to an exemplary embodiment of the present invention, in Chemical Formulae 1 to 3, $Ar_1$ is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; an arylphosphine group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a trialkylsilyl group; or a triarylsilyl group. The group to which two or more groups are bonded may be a group to which two or more substituents exemplified above are bonded, for example, a heteroaryl group substituted with an aryl group, an aryl group substituted with a heteroaryl group, an aryl group substituted with an arylamino group, an aryl group substituted with an arylphosphine group, and the like, and are not limited to these examples.

According to an exemplary embodiment of the present invention, in Chemical Formulae 1 to 3, $Ar_1$ is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; an arylphosphine group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a trialkylsilyl group; or a triarylsilyl group, and here, the halogen group is a fluorine group, the alkyl group is a straight-chained or branch-chained alkyl group having 1 to 20 carbon atoms, for example, 1 to 6 carbon atoms, the silyl group is trialkylsilyl, for example, a trimethylsilyl group or a triphenylsilyl, the aryl group and aryl are phenyl, biphenylyl, terphenylyl, quarterphenyl, naphthyl, phenanthrenyl, a triphenylene group, fluorenyl, and a spirobifluorene group, and the heteroaryl group may be pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or a substituent of Group A, but these groups are not limited to these examples.

[Group A]

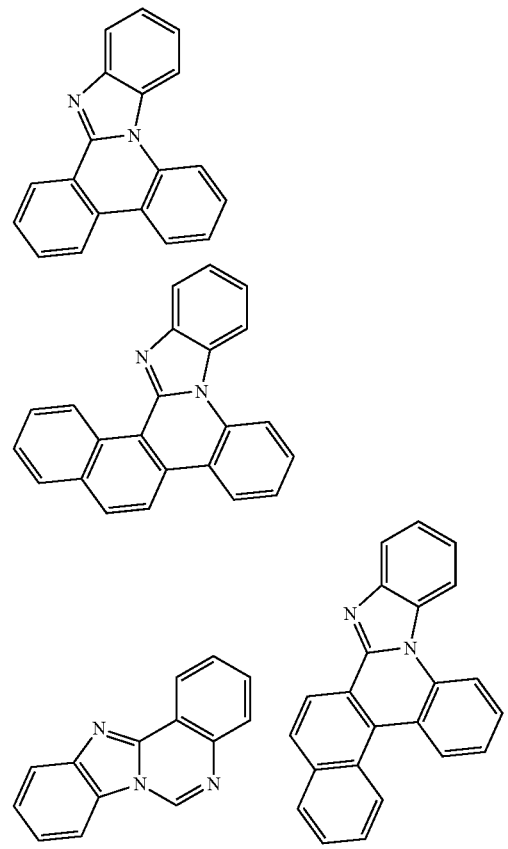

In the structural formulae, any one carbon is a linking moiety for forming a monovalent group, and the other carbons are a group to which one or two or more groups of hydrogen or a substituent, for example, a halogen group, a nitrile group, an alkyl group, a silyl group, an arylamino group, an arylphosphine group, an aryl group, and a heteroaryl group is or are bonded.

According to an exemplary embodiment of the present invention, in Chemical Formulae 1 to 3, $Ar_1$ is selected from the following structural formulae.

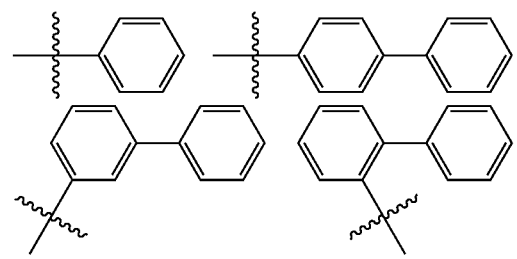

-continued
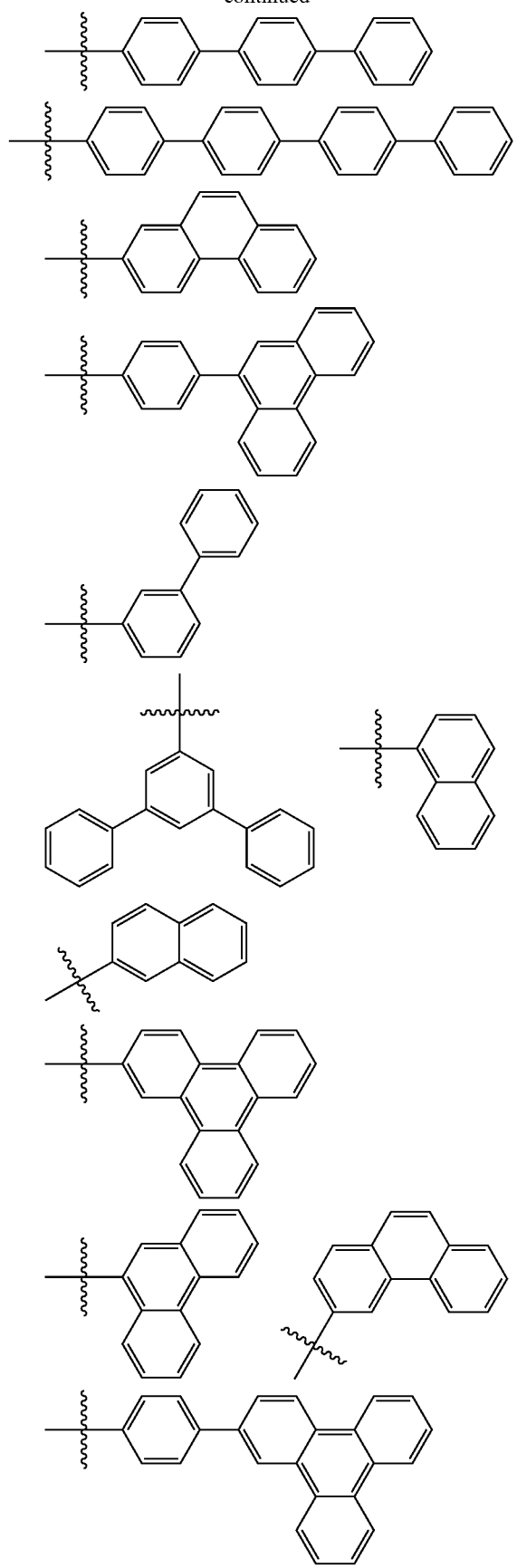
-continued
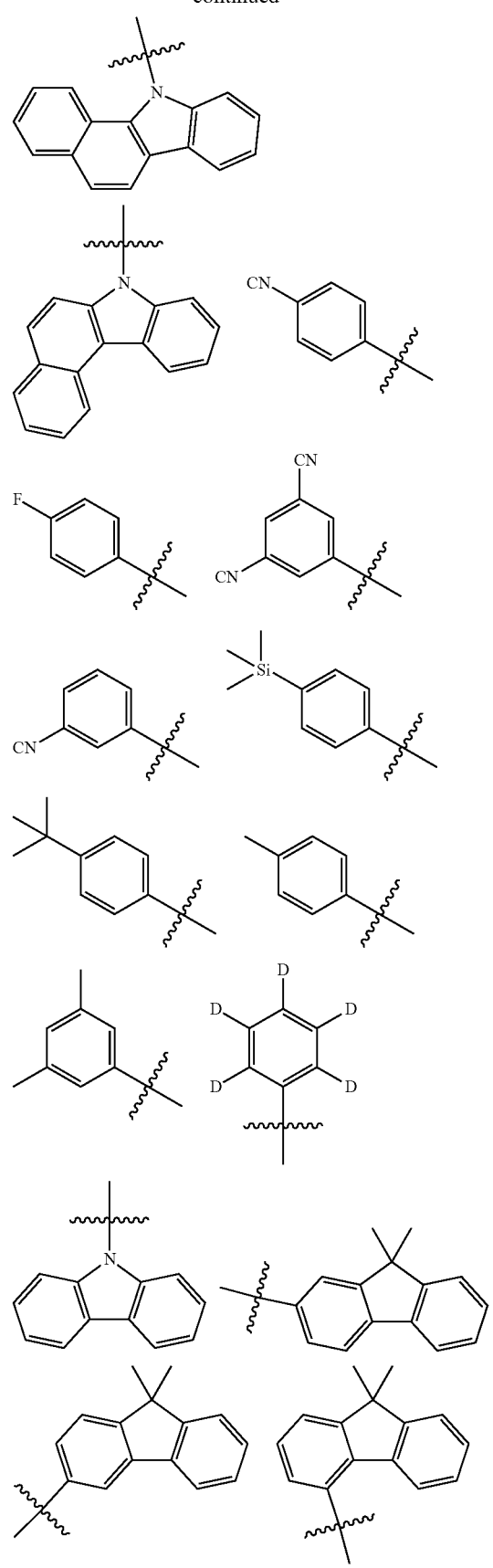

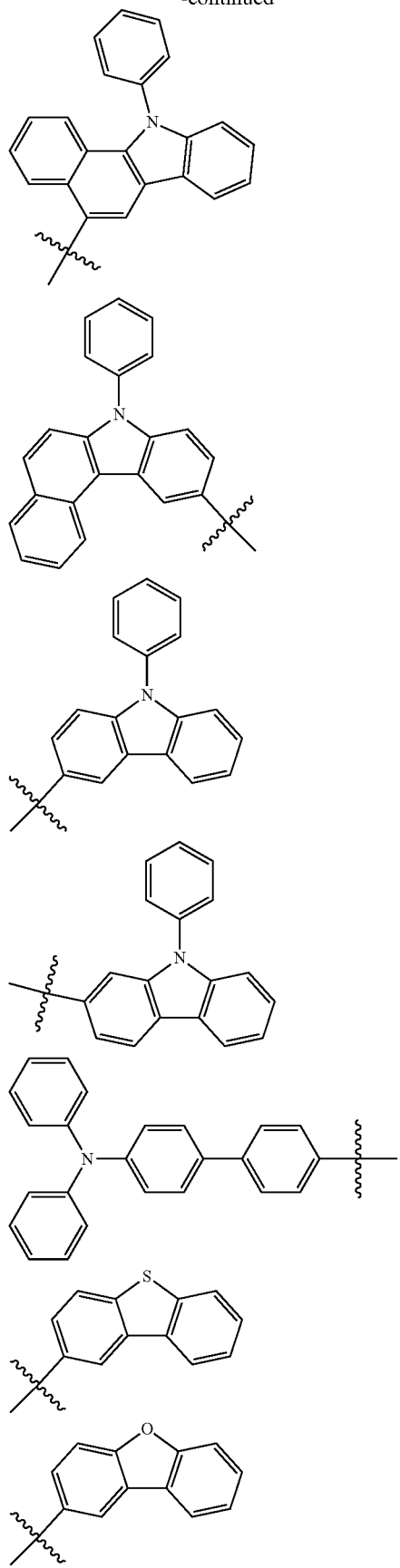
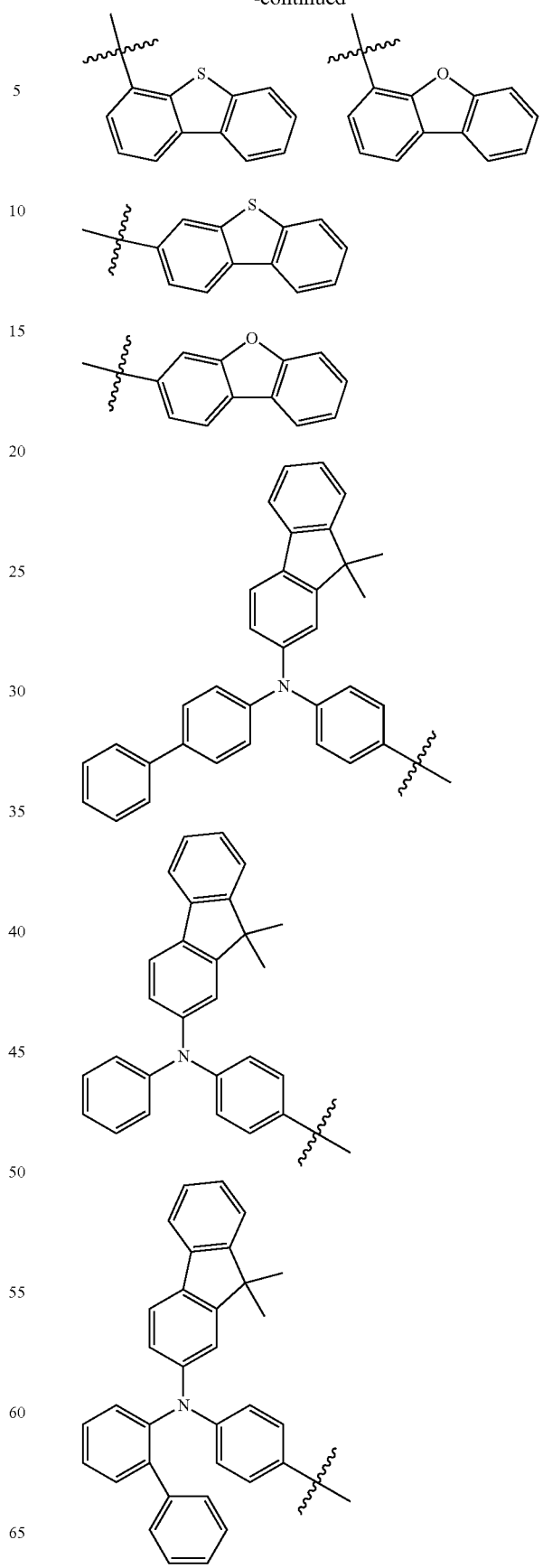

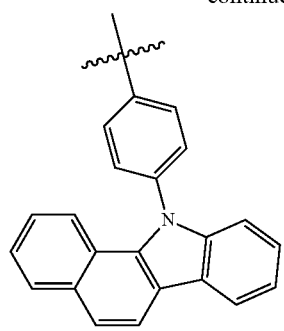
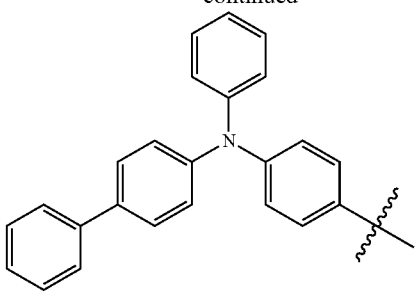
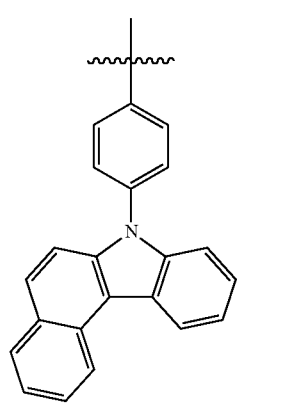
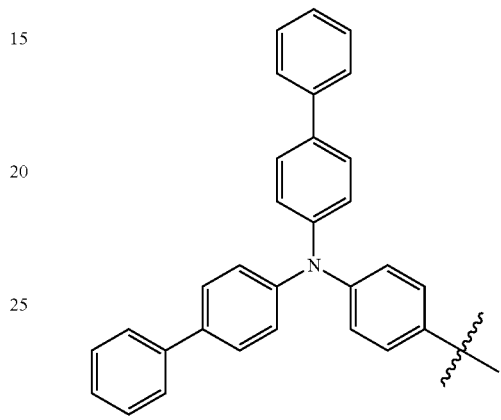
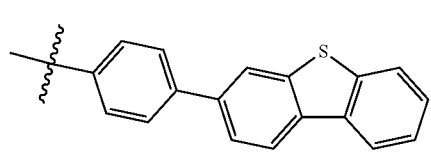
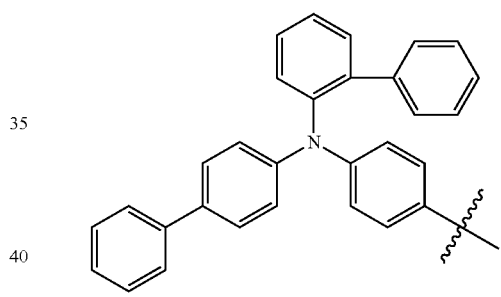
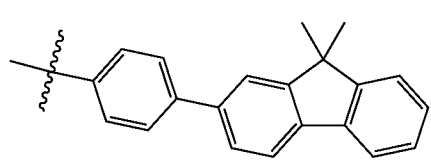
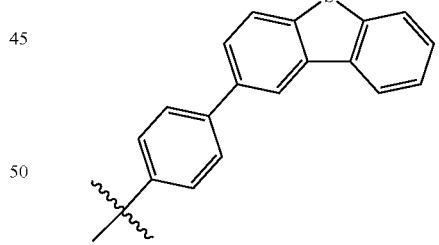
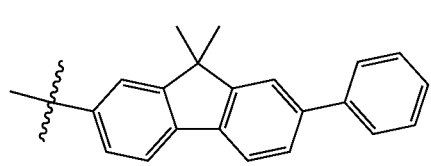
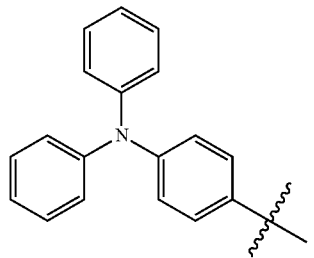
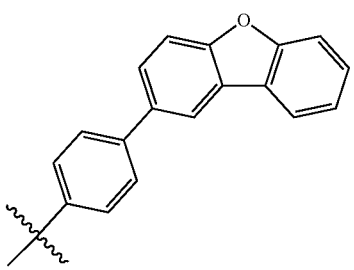

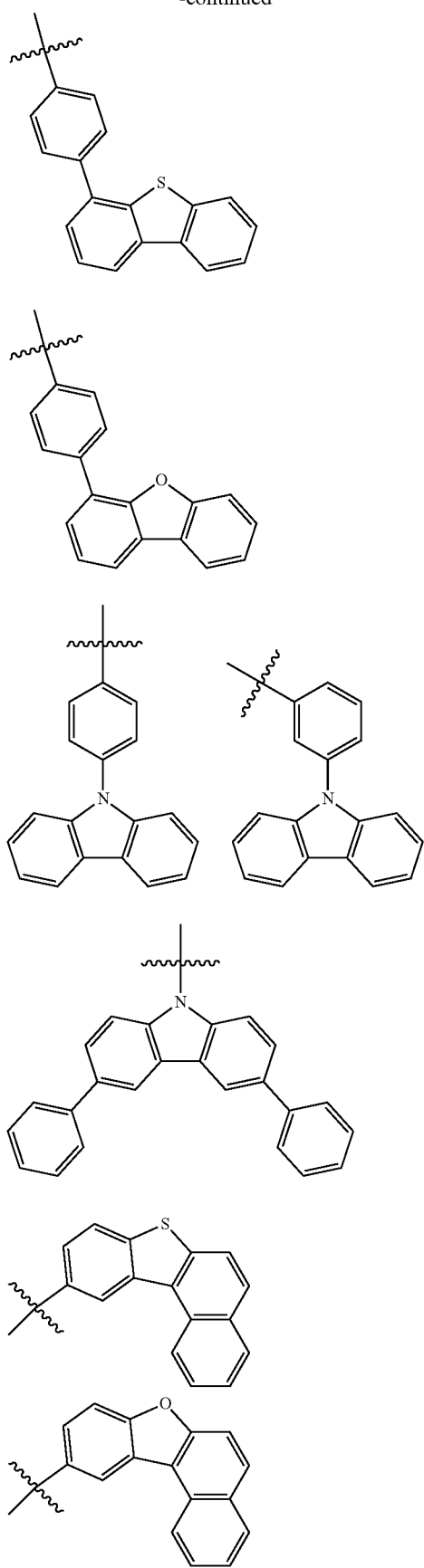
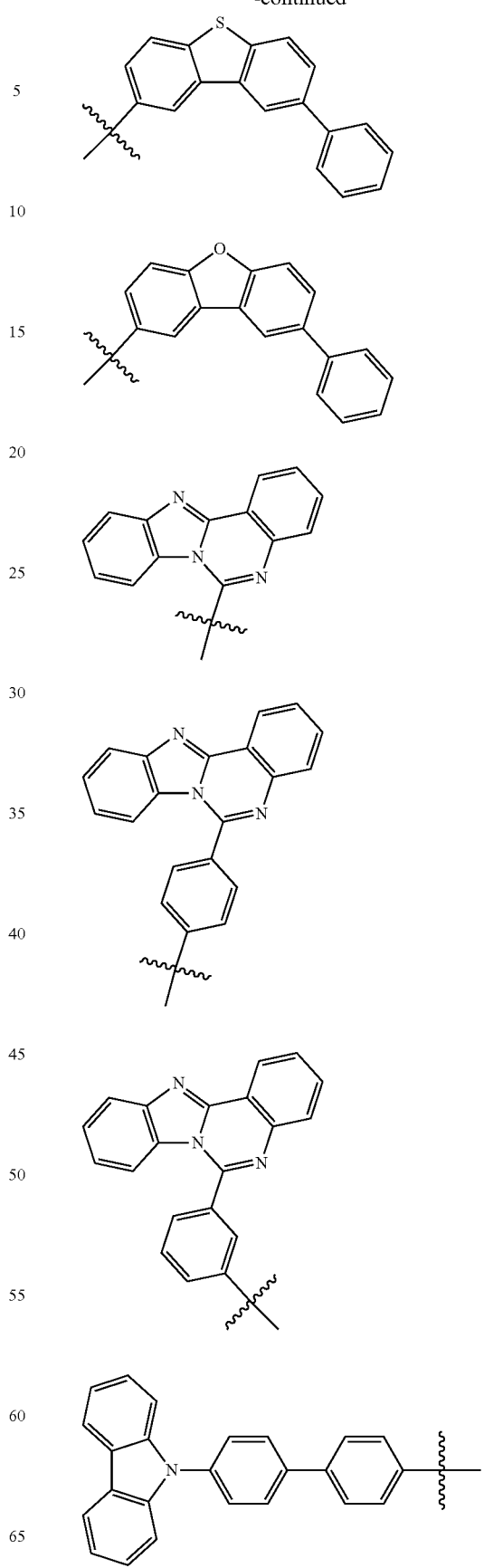

-continued
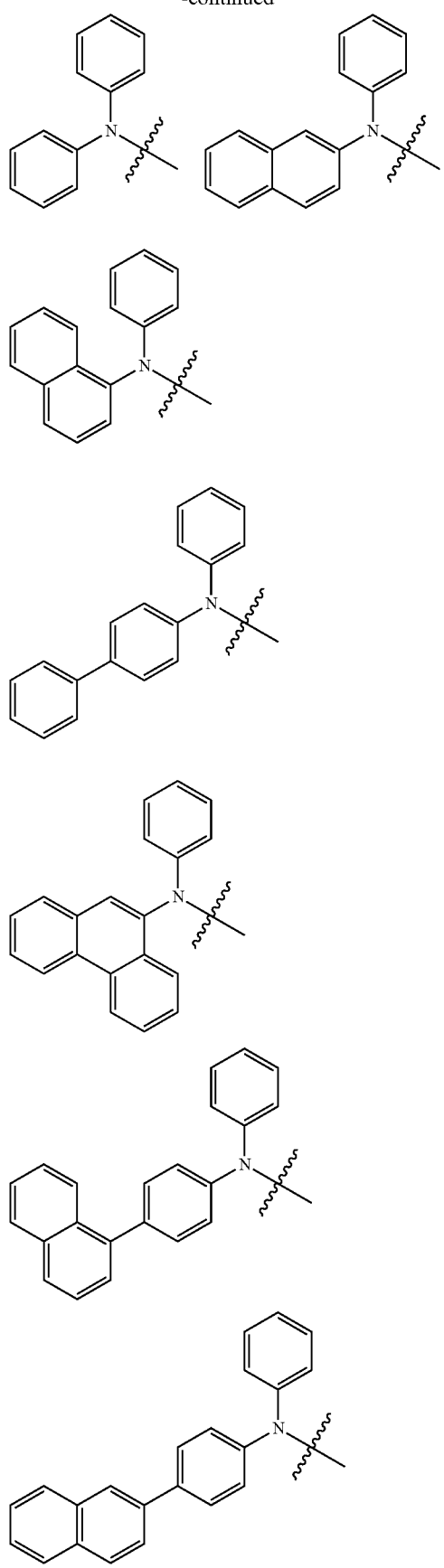
-continued
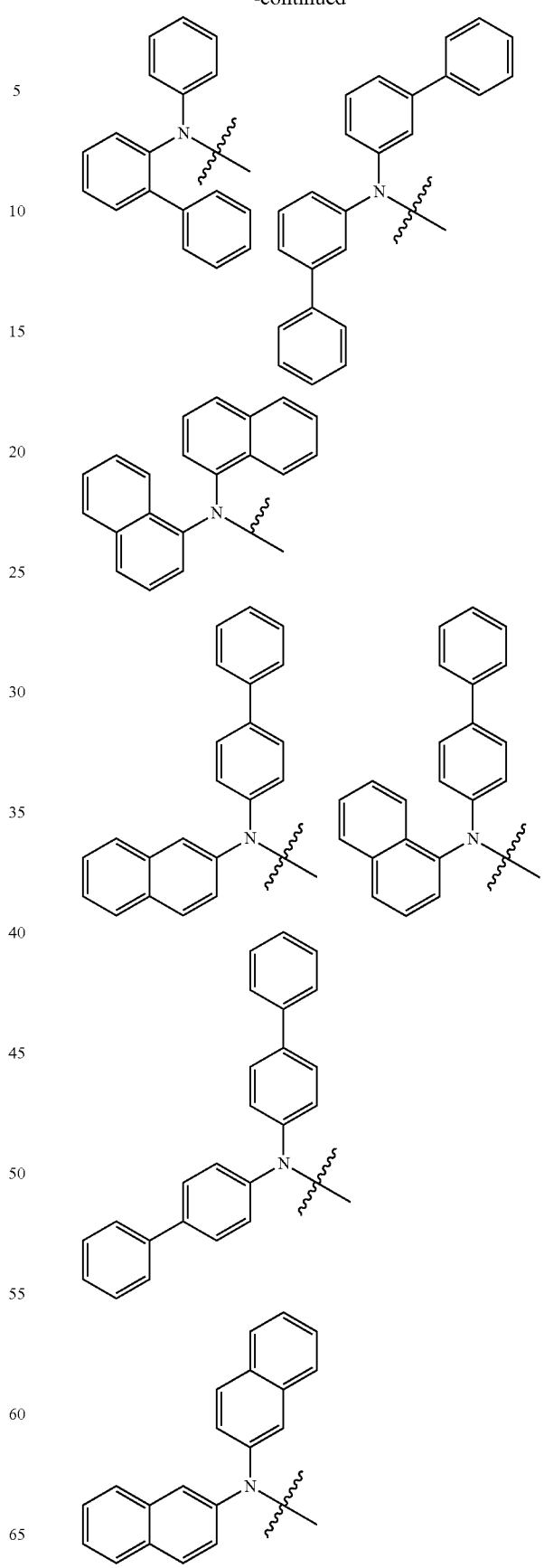

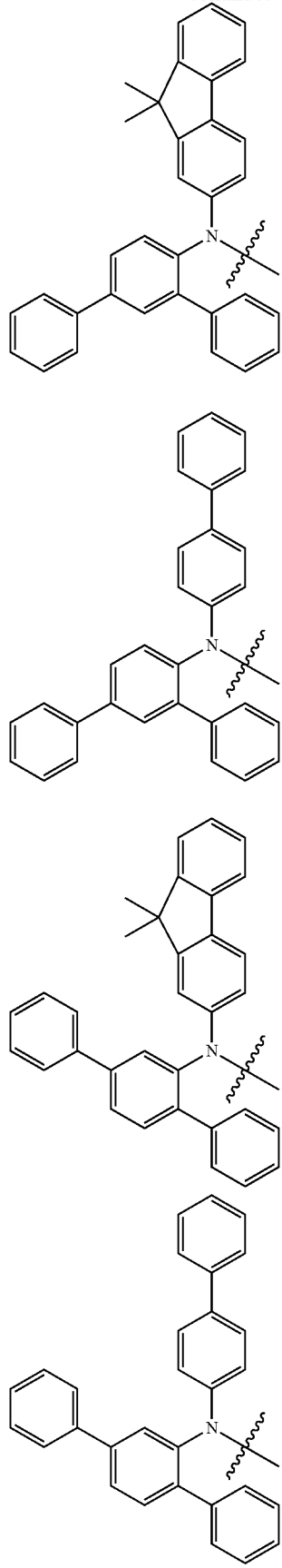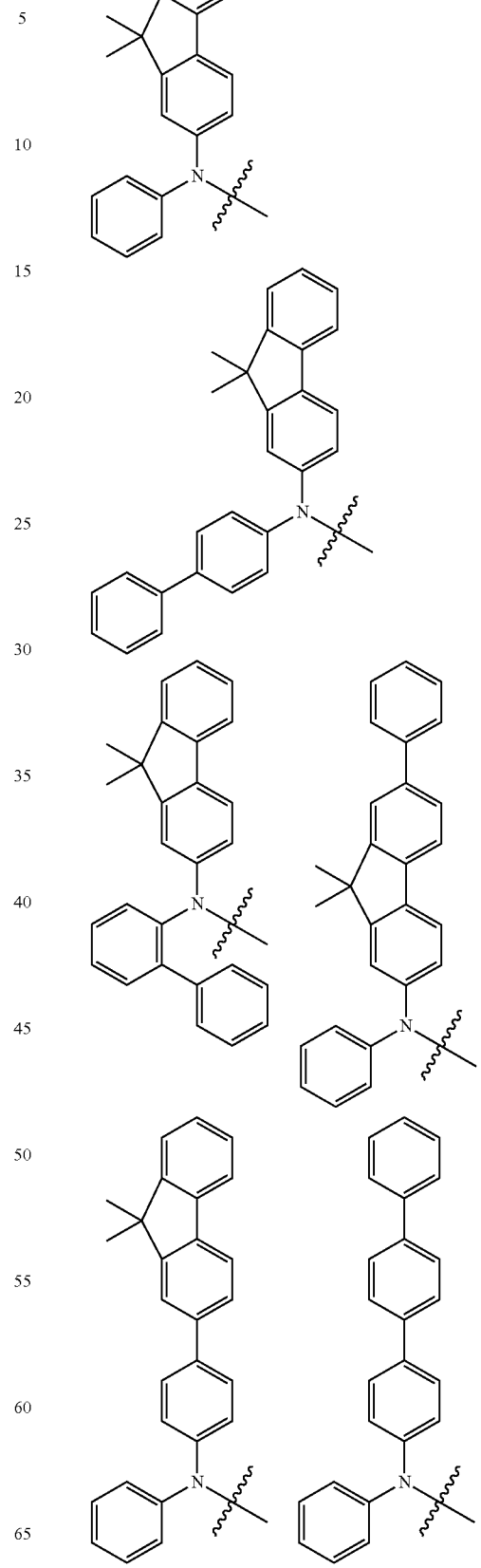

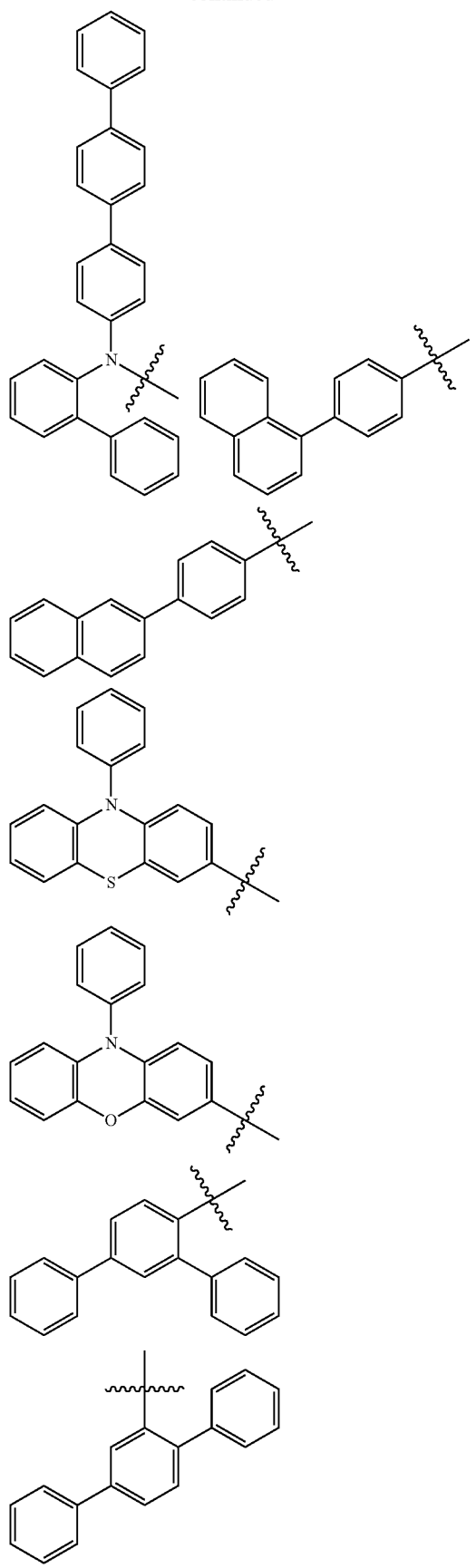
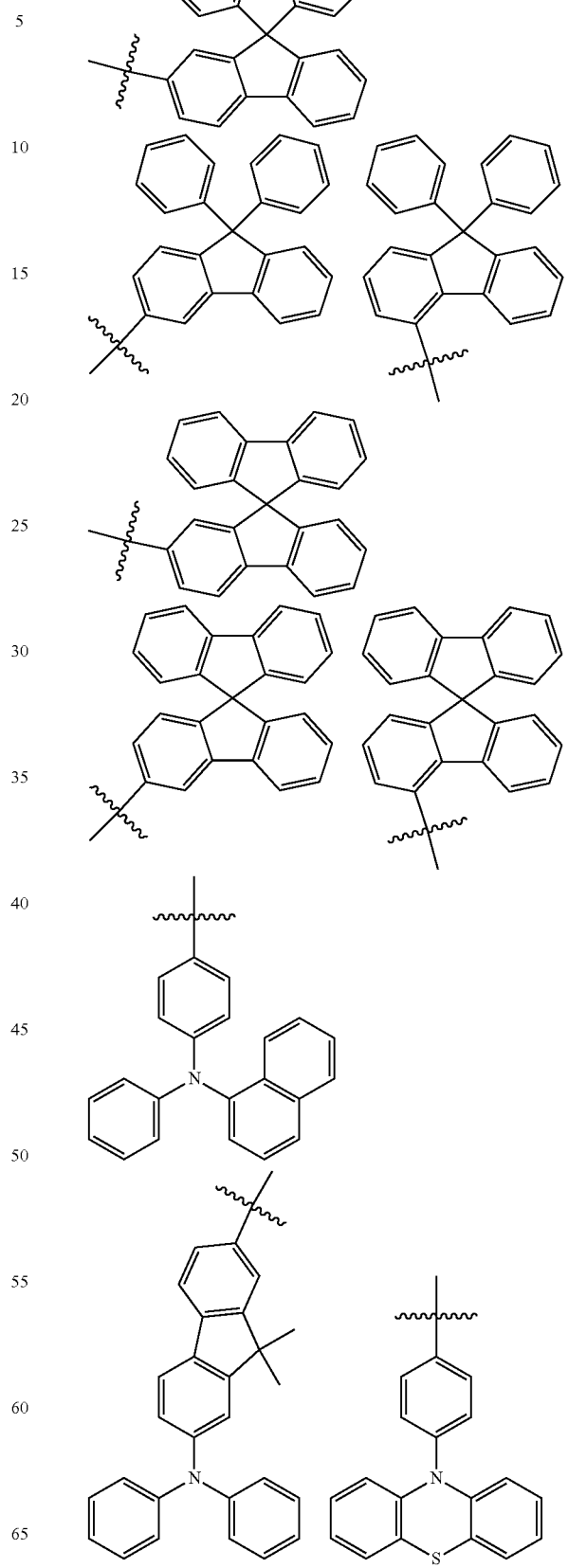

-continued
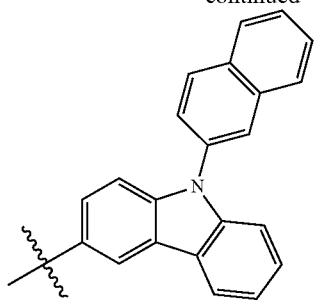
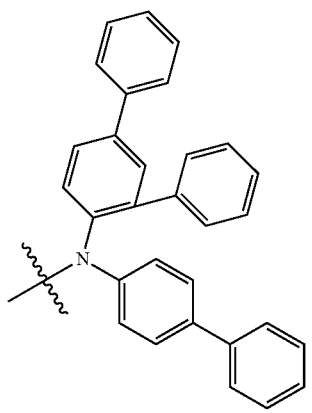
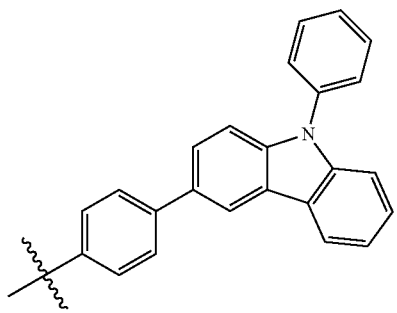
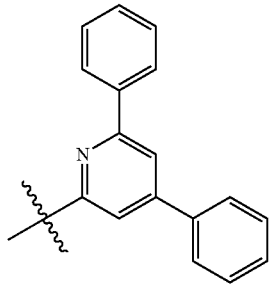
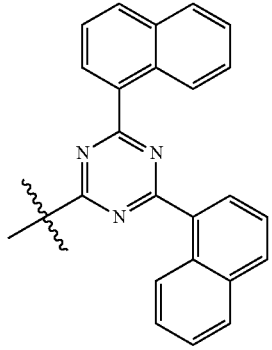
-continued
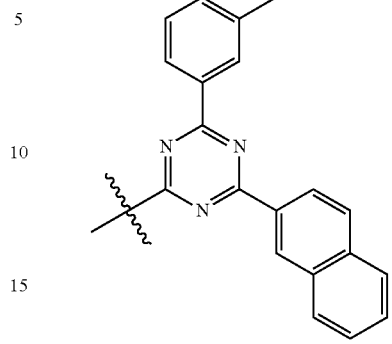
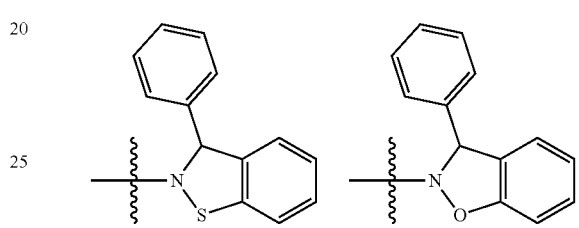
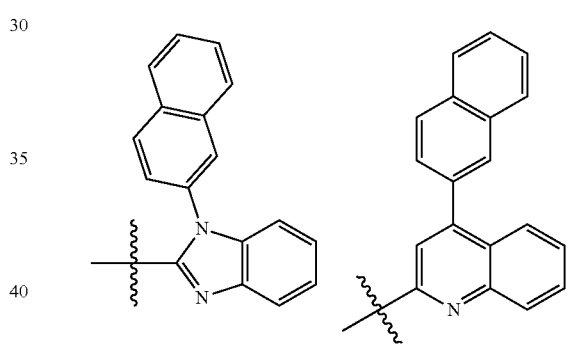
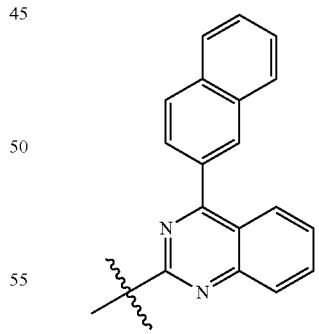
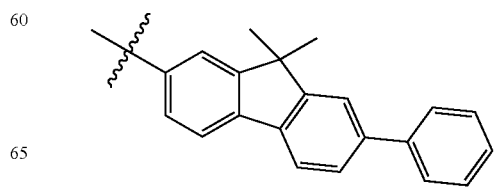

-continued
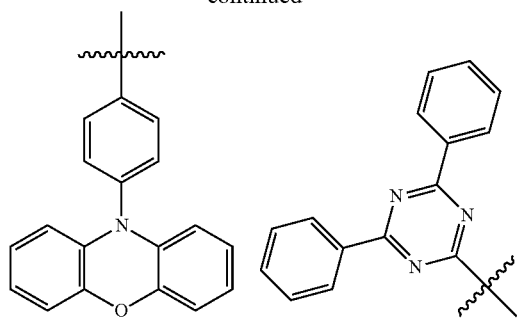
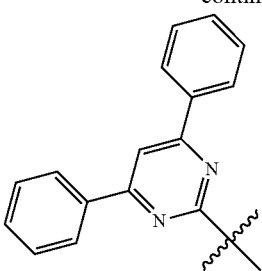
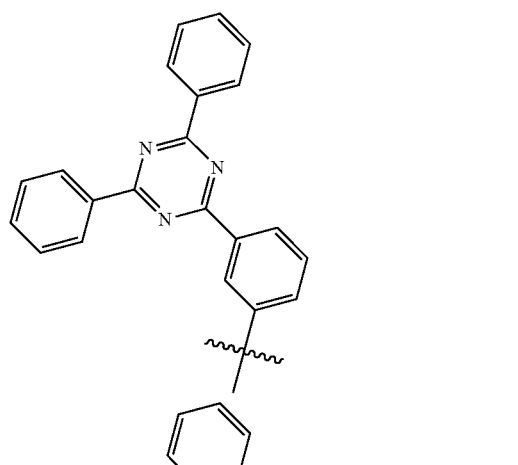
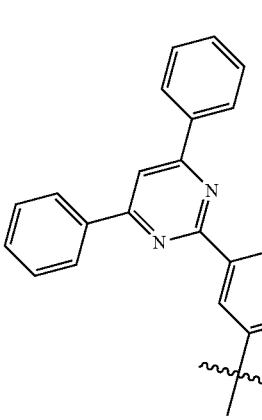
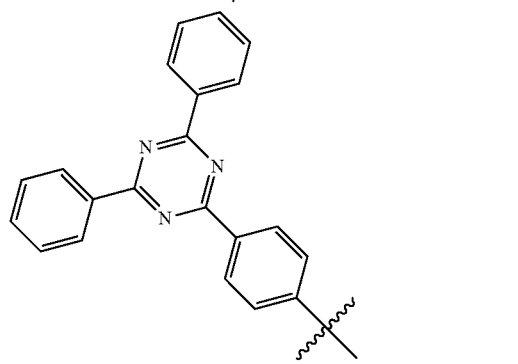
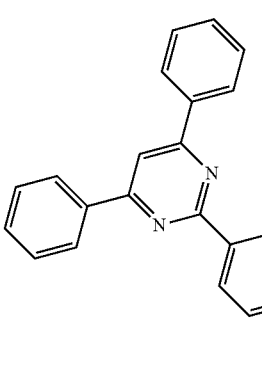
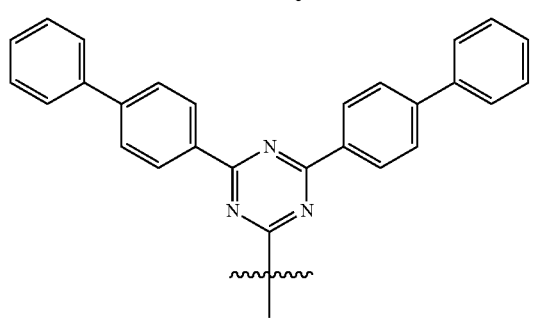
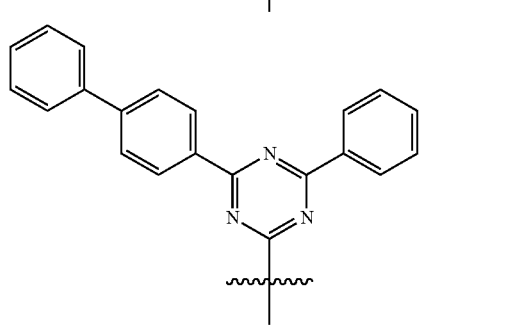
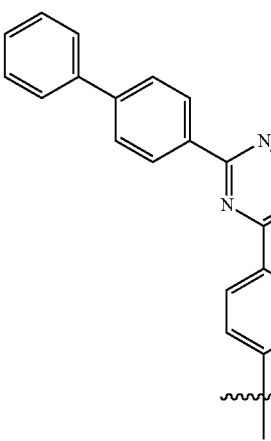

31
-continued
32
-continued
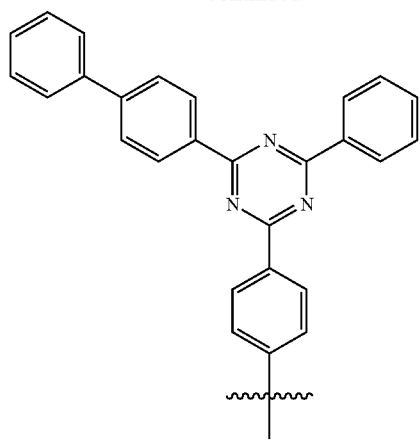
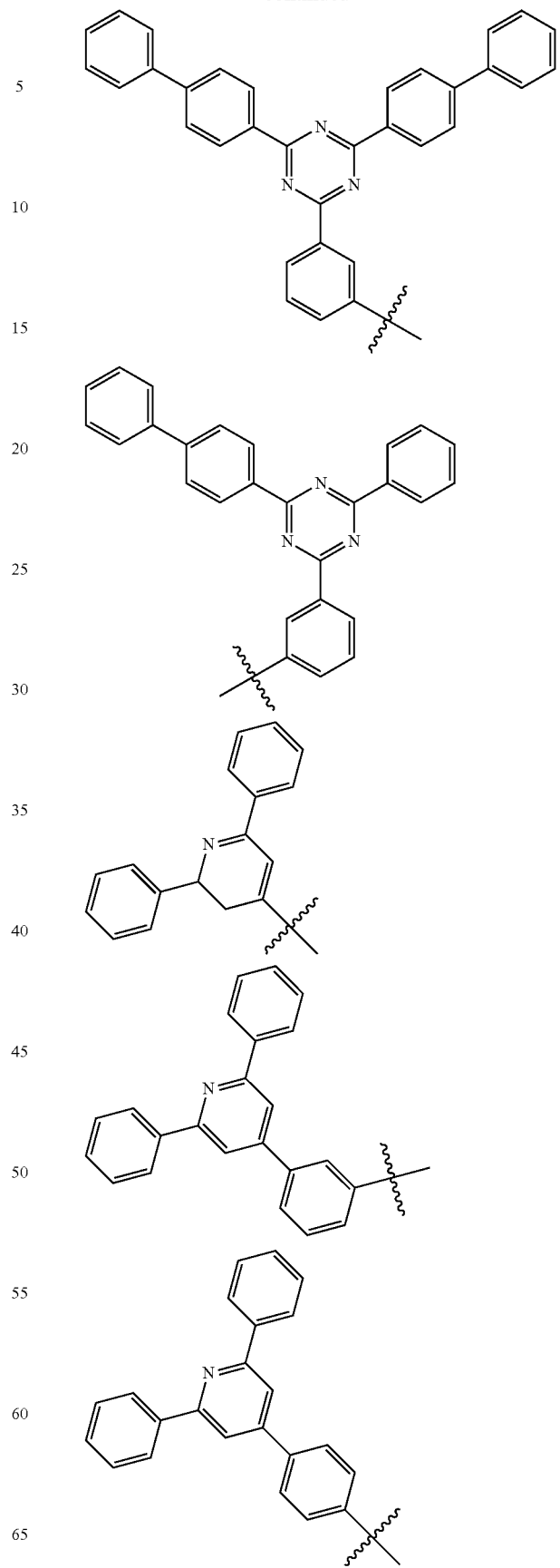

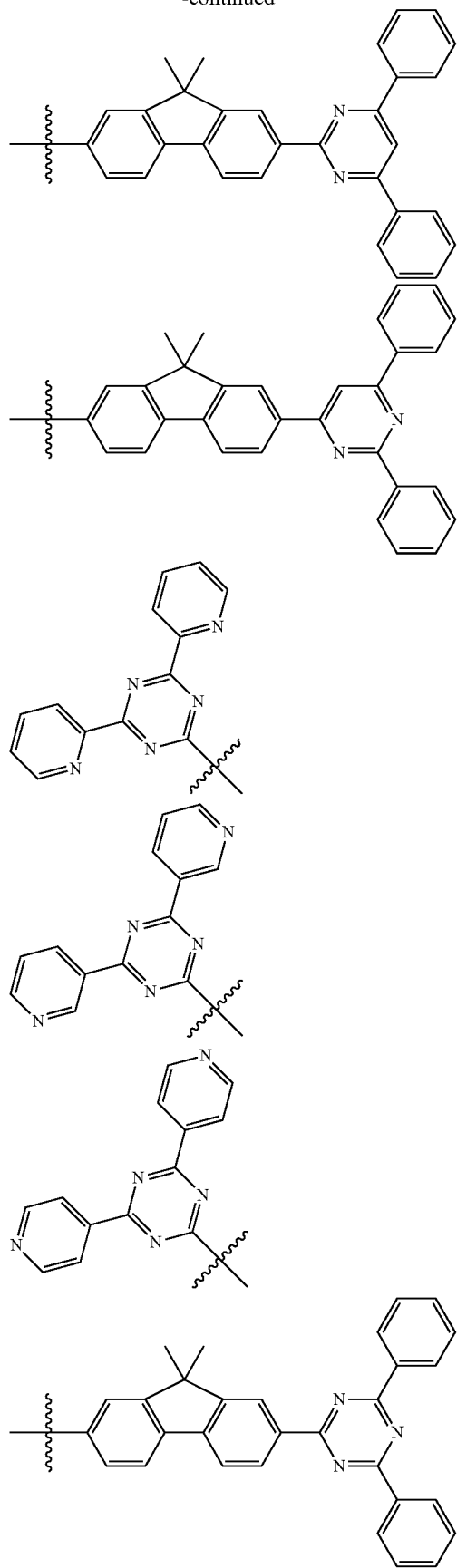

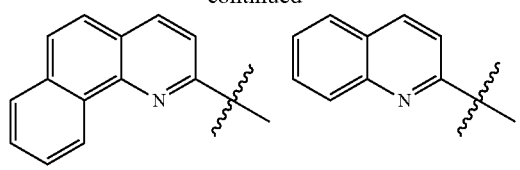
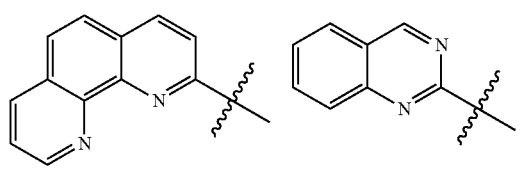
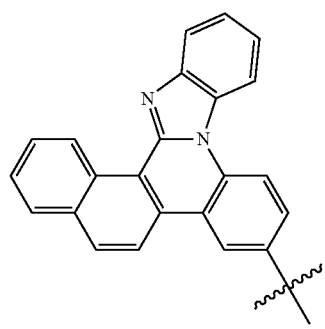
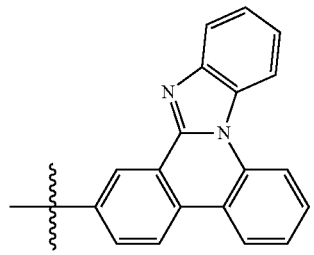
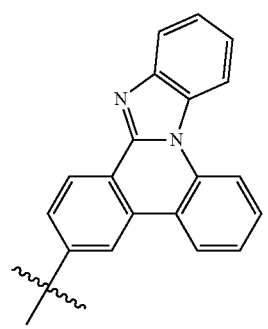
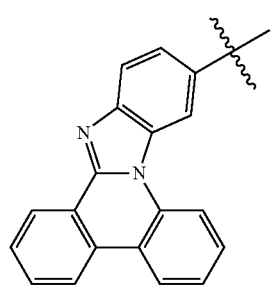
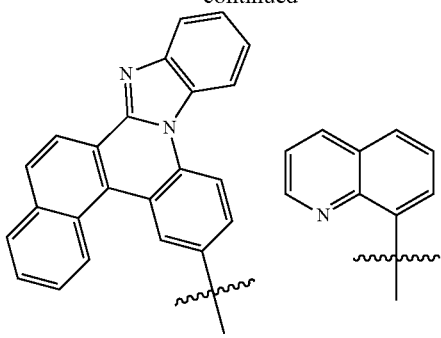
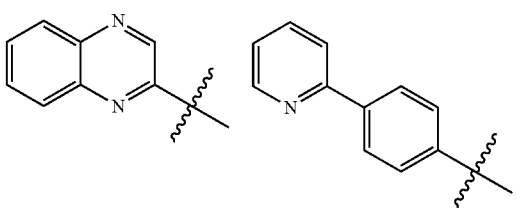
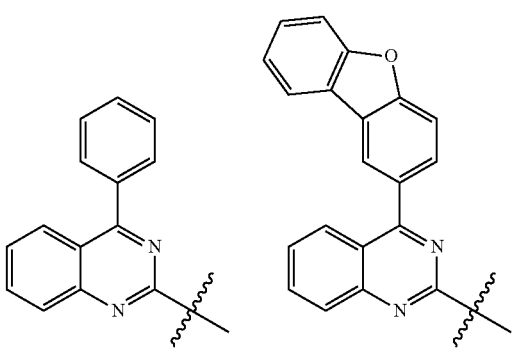
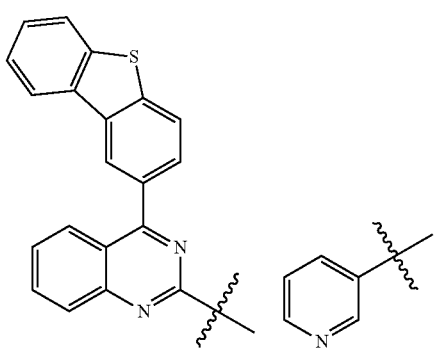
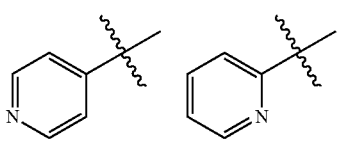

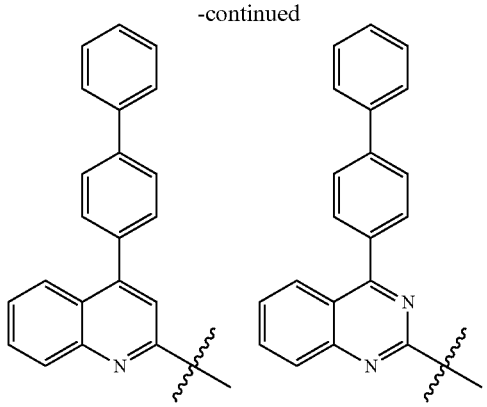
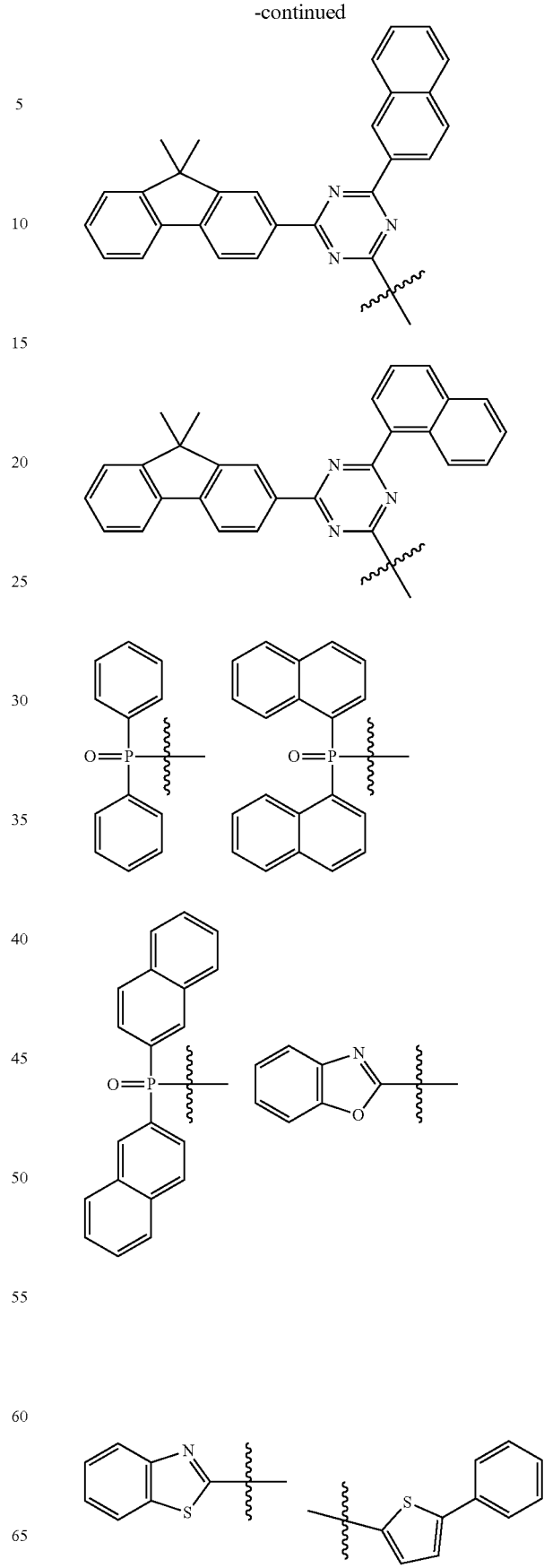

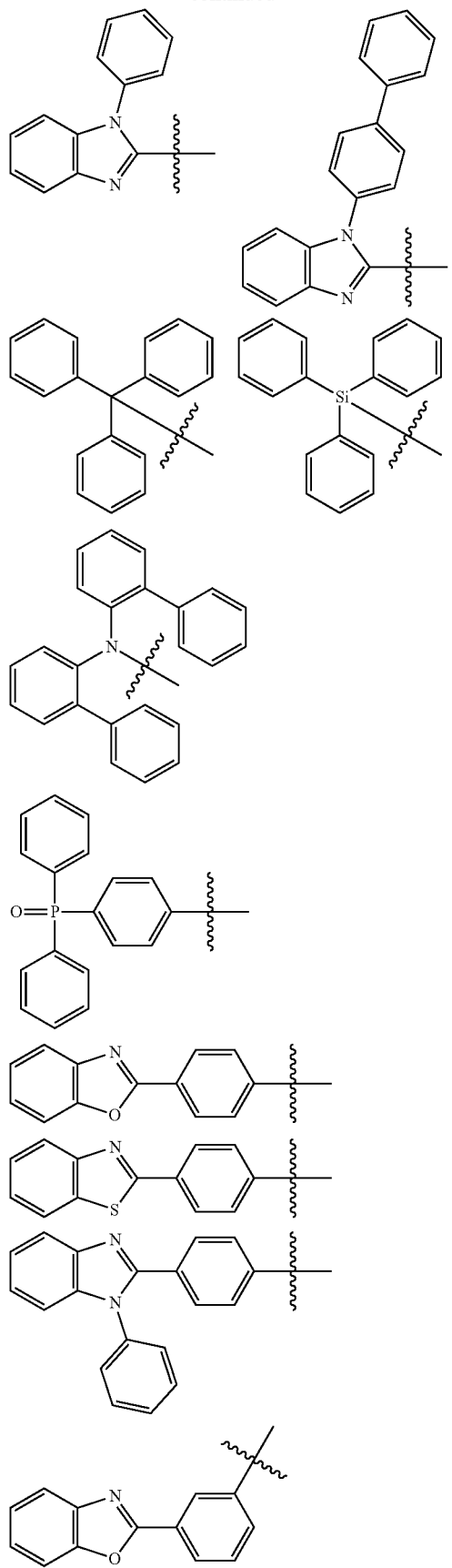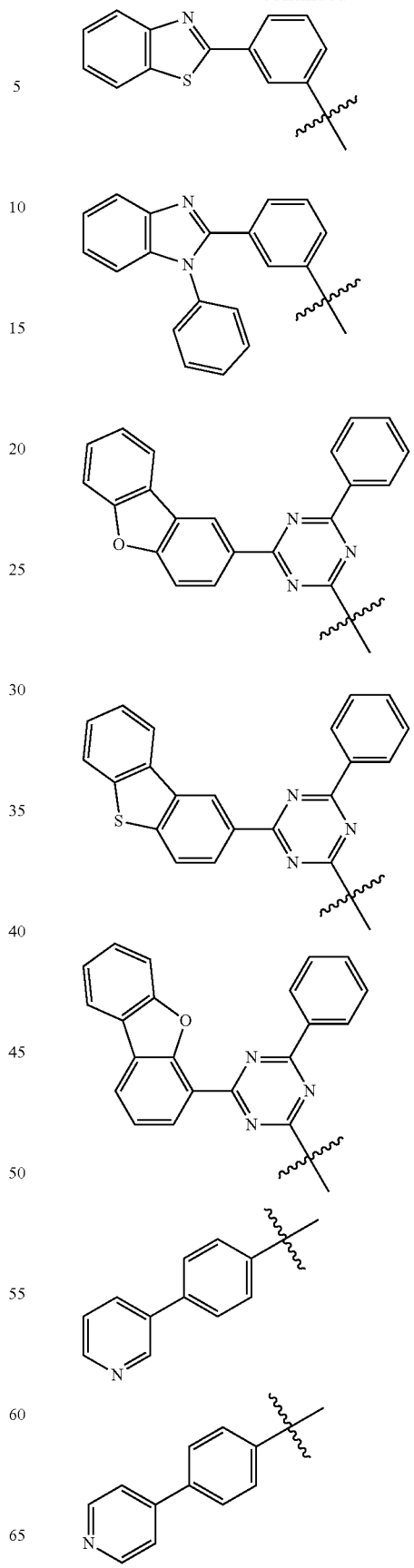

-continued

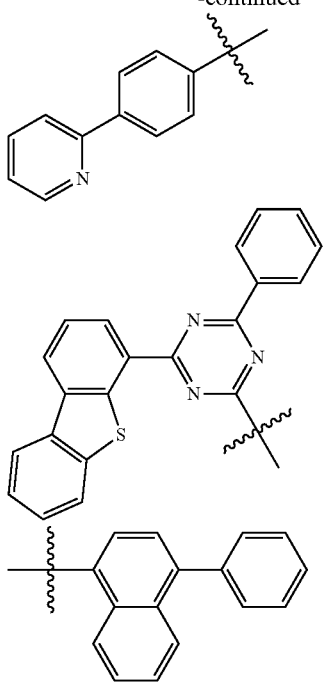

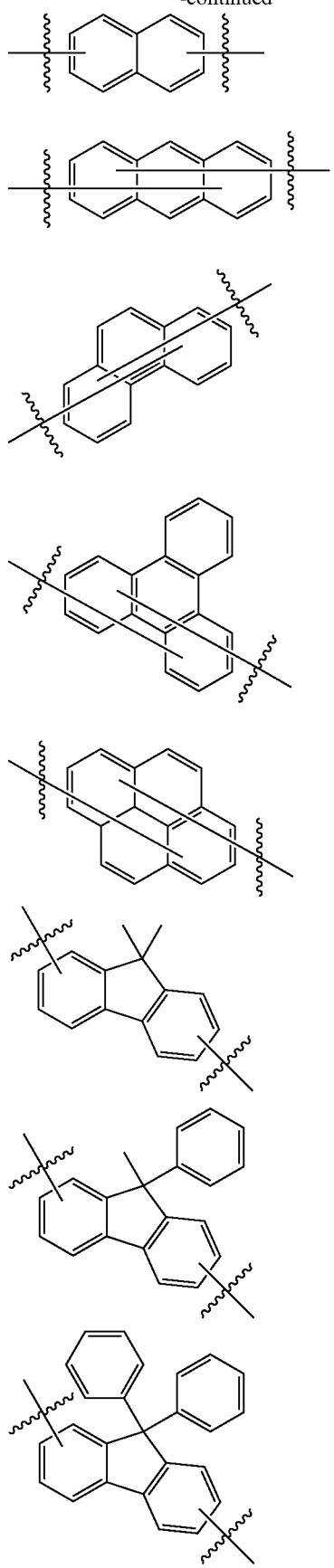

According to an exemplary embodiment of the present invention, in Chemical Formulae 1 to 3, $L_1$ is a direct bond, a substituted or unsubstituted arylene, a substituted or unsubstituted heteroarylene, or a substituted or unsubstituted divalent amine.

According to an exemplary embodiment of the present invention, in Chemical Formulae 1 to 3, $L_1$ is a direct bond, a substituted or unsubstituted phenylene, a substituted or unsubstituted biphenylylene, a substituted or unsubstituted terphenylylene, a substituted or unsubstituted quarterphenylylene, a substituted or unsubstituted naphthylene, a substituted or unsubstituted anthrylene, a substituted or unsubstituted fluorene, a substituted or unsubstituted phenanthrene, a substituted or unsubstituted pyrene, or a substituted or unsubstituted triphenylene.

According to an exemplary embodiment of the present invention, in Chemical Formulae 1 to 3, $L_1$ is a direct bond, phenylene, biphenylylene, terphenylylene, quarterphenylylene, naphthylene, anthrylene, fluorene, phenanthrene, pyrene, or triphenylene.

According to an exemplary embodiment of the present invention, in Chemical Formulae 1 to 3, $L_1$ may be selected from a direct bond, or the following structural formulae.

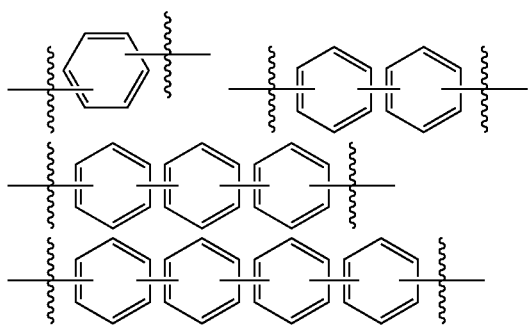

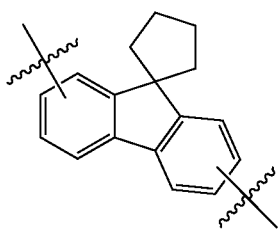
According to an exemplary embodiment of the present invention, in Chemical Formulae 1 to 3, n is 0 or 1.
According to an exemplary embodiment of the present invention, $R_1$ to $R_7$ are hydrogen or deuterium.
According to an exemplary embodiment of the present invention, the compound of Chemical Formula 1 may be any one selected from the following compounds.
7-1
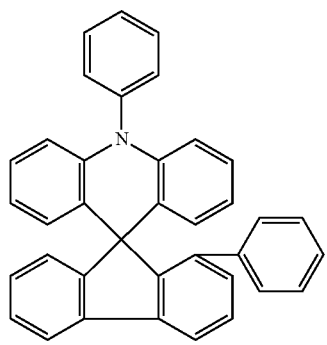
7-2
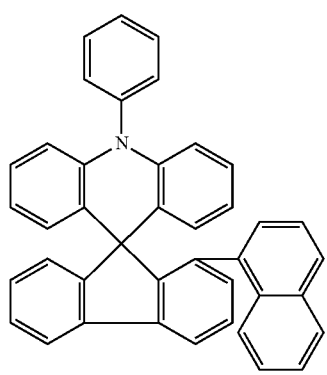
7-3
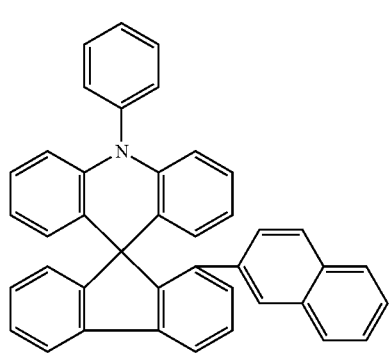
7-4
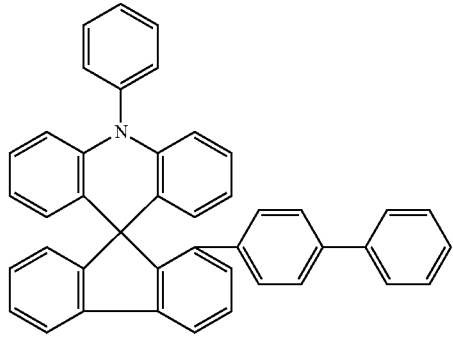
7-5
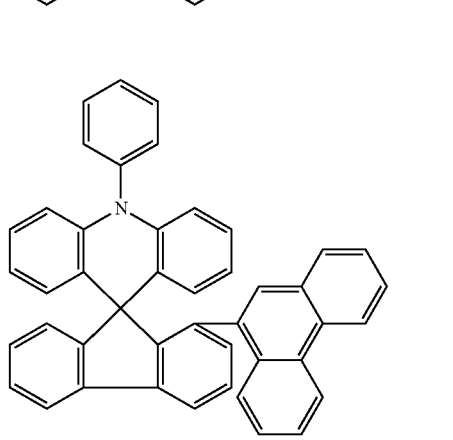
7-6
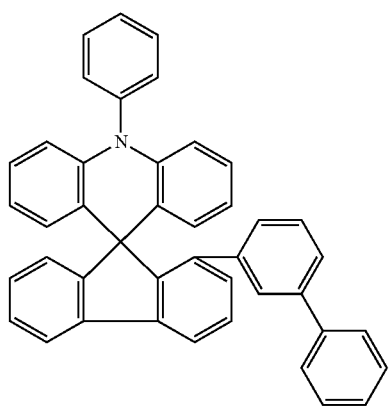
7-7
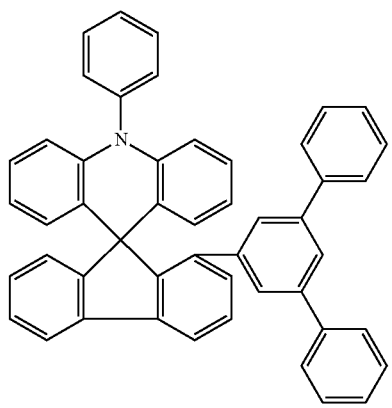

7-8
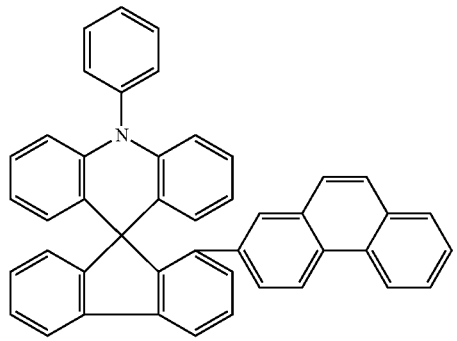
7-9
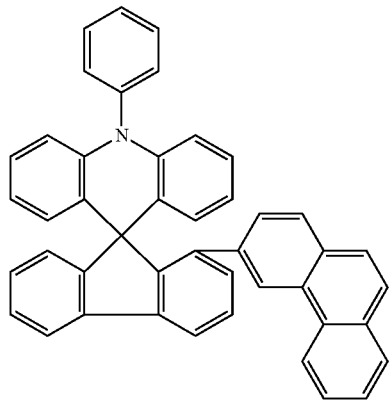
7-10
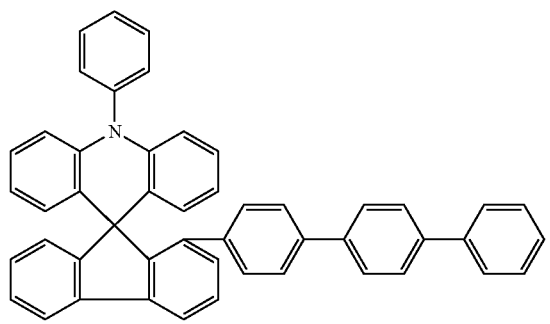
7-11
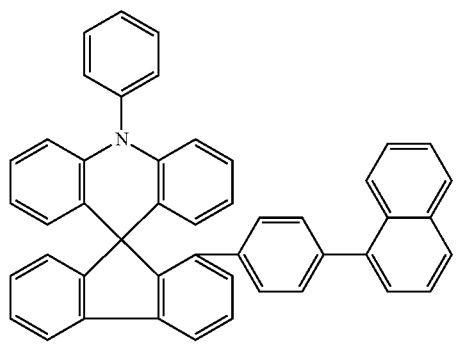
7-12
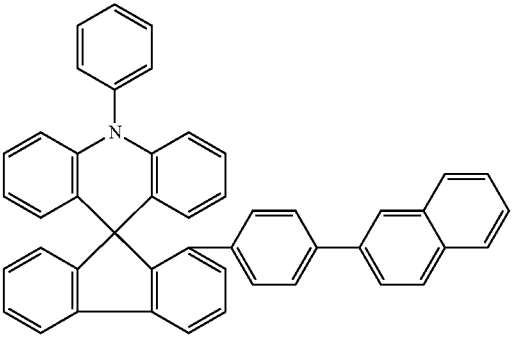
7-13
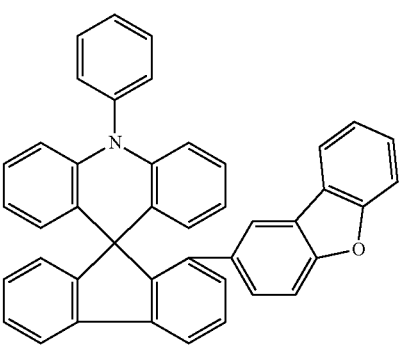
7-14
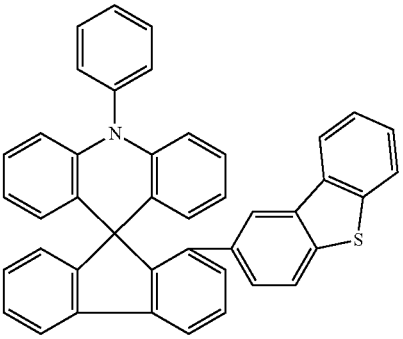
7-15
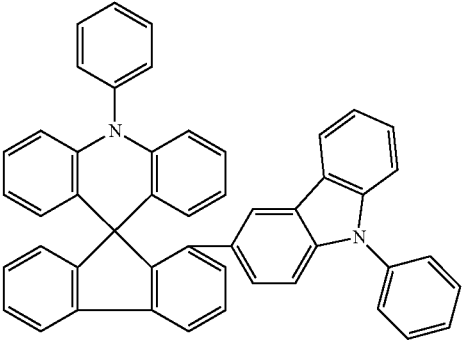

7-16
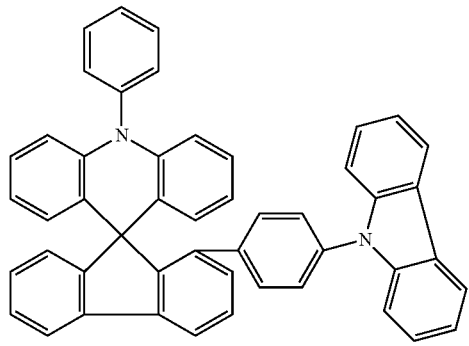
7-17
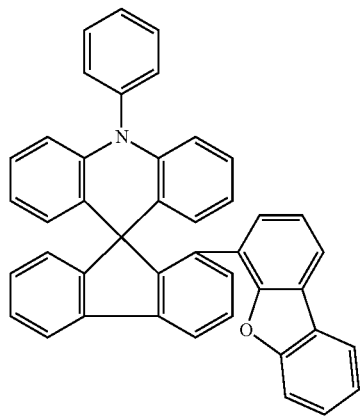
7-18
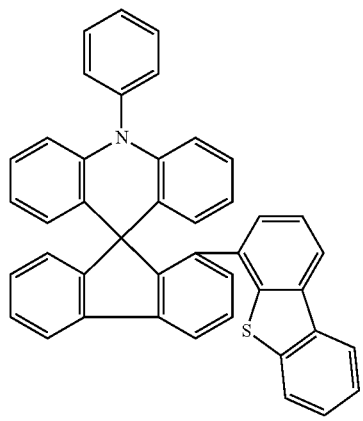
7-19
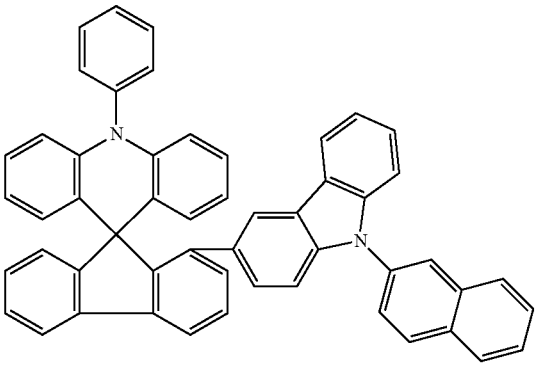
7-20
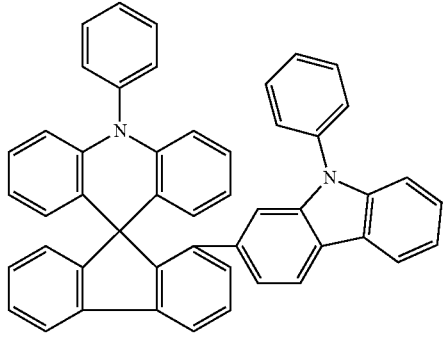
7-21
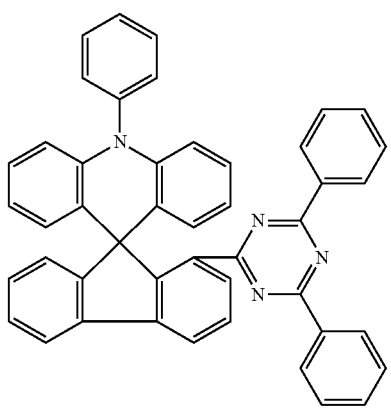
7-22
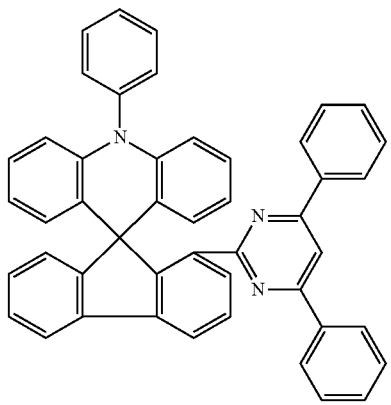
7-23
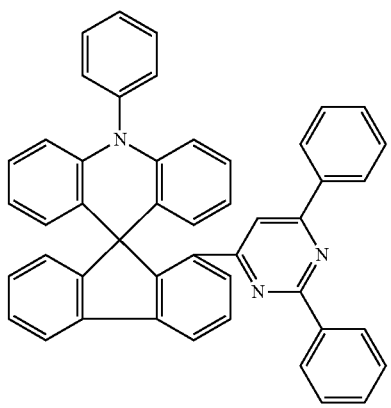

7-24
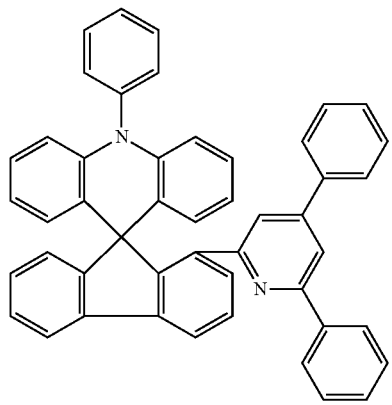
7-27
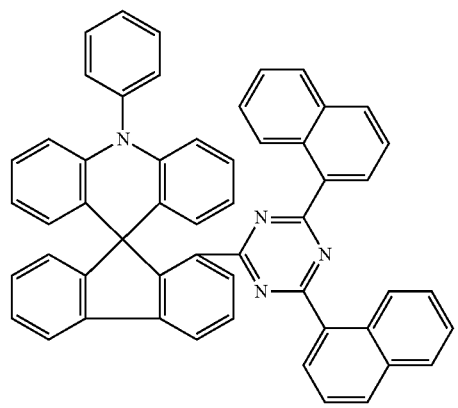
7-25
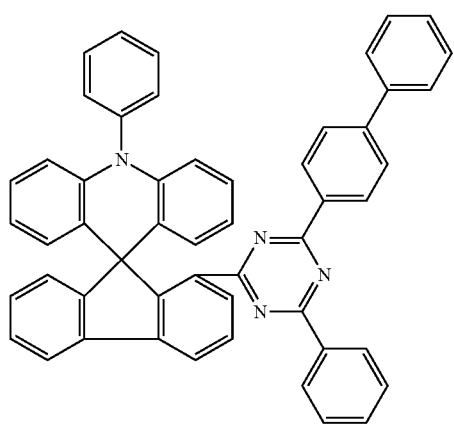
7-28
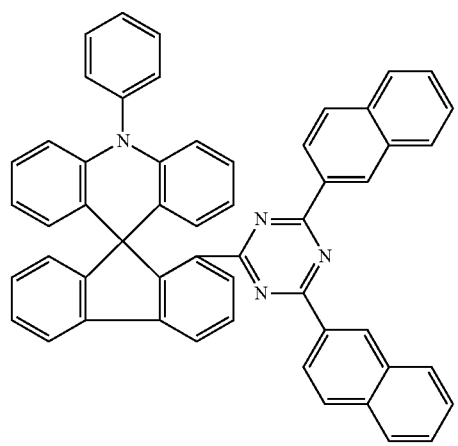
7-26
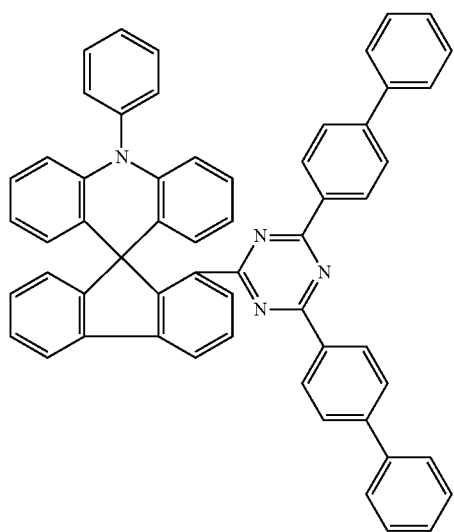
7-29
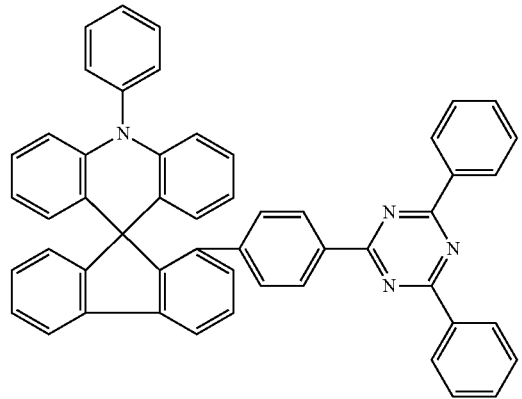

7-30
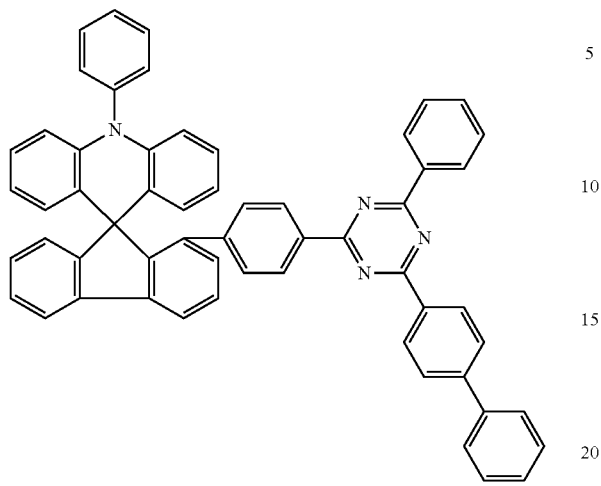
7-31
7-32
7-33
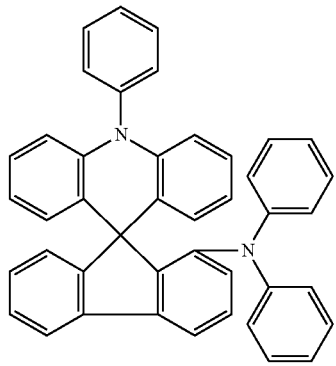
7-34
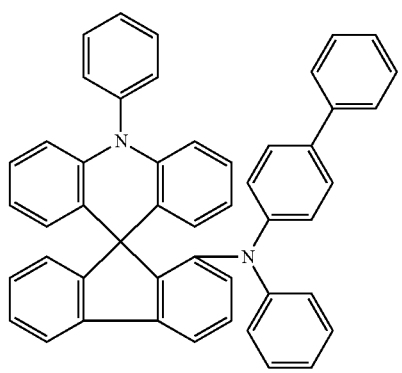
7-35
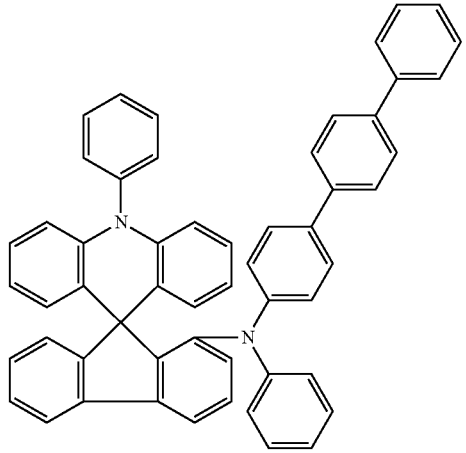

7-36
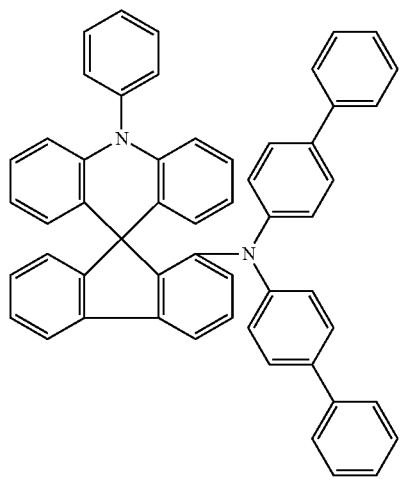
7-39
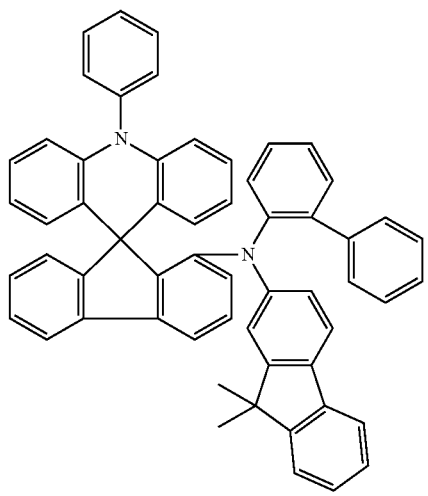
7-37
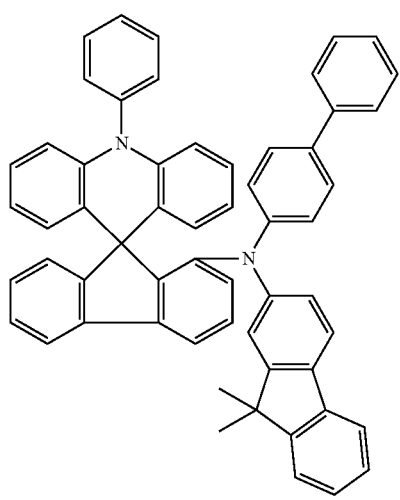
7-40
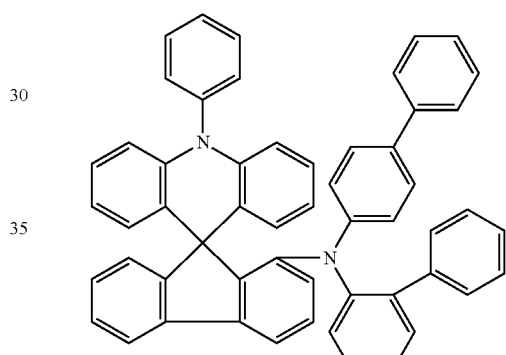
7-38
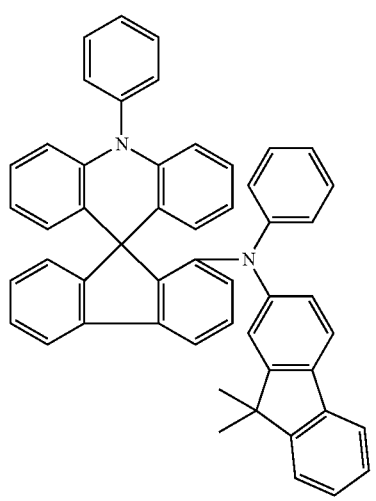
7-41
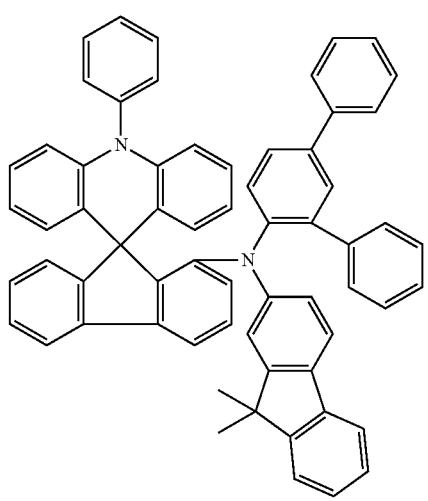

7-42
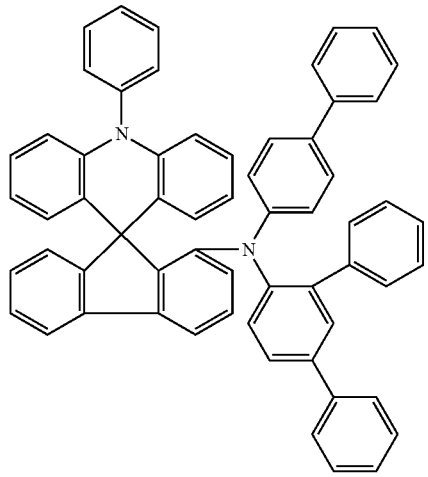
7-45
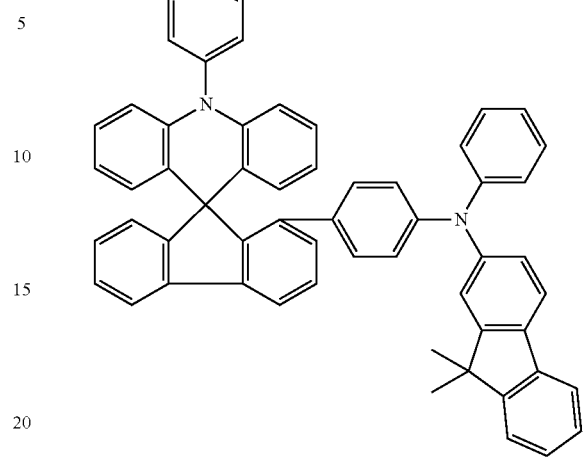
7-43
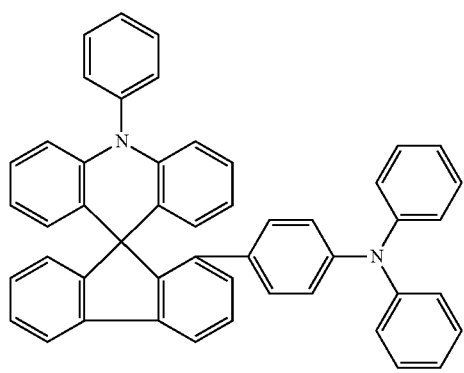
7-46
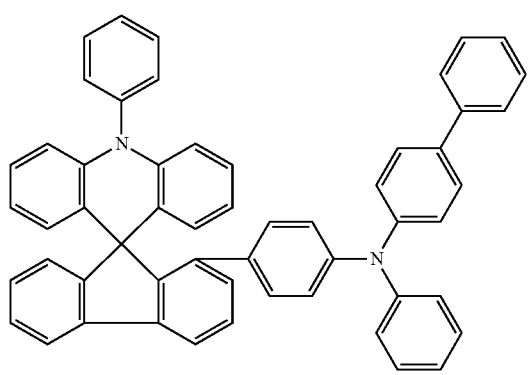
7-44
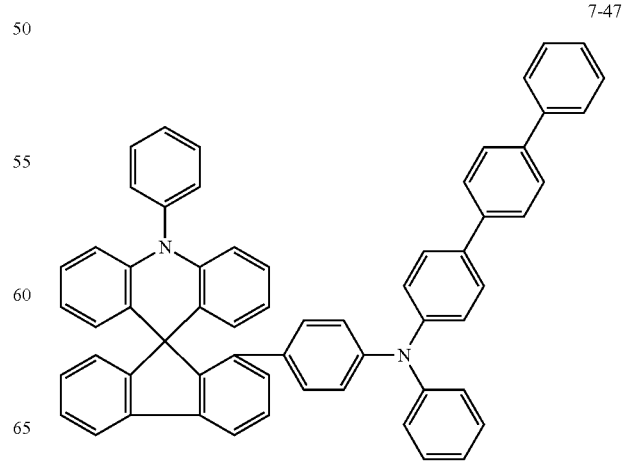
7-47

-continued
7-48
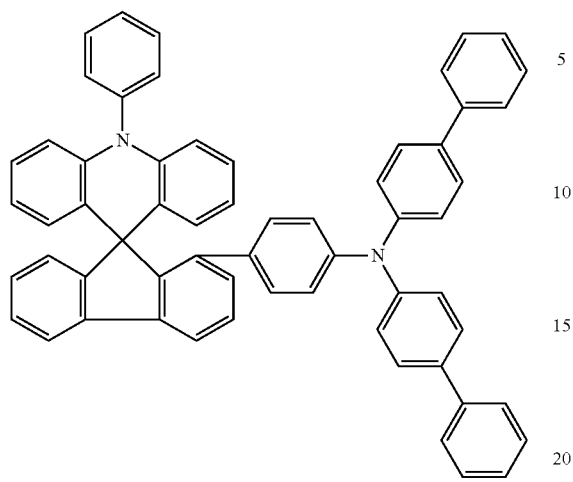
7-49
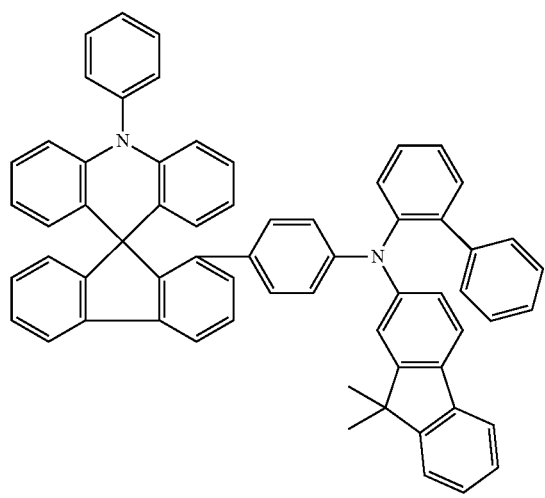
7-50
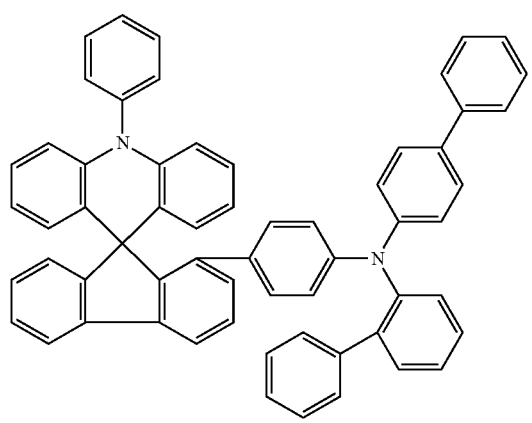
-continued
7-51
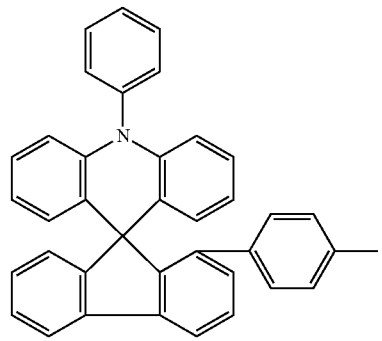
7-52
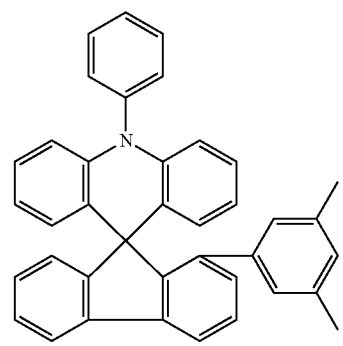
7-53
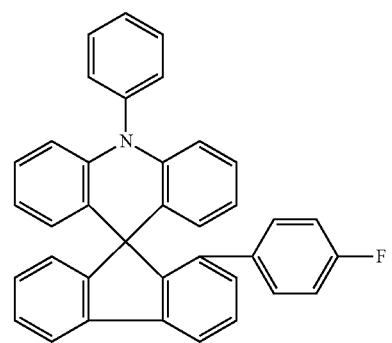
7-54
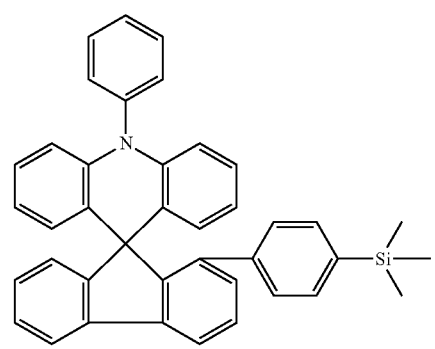

7-55
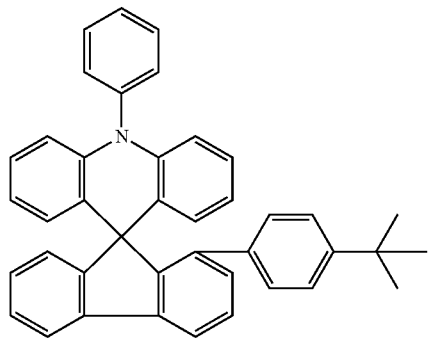
7-56
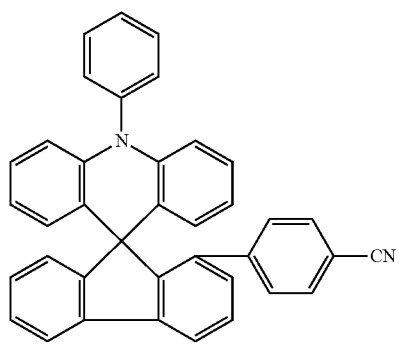
7-57
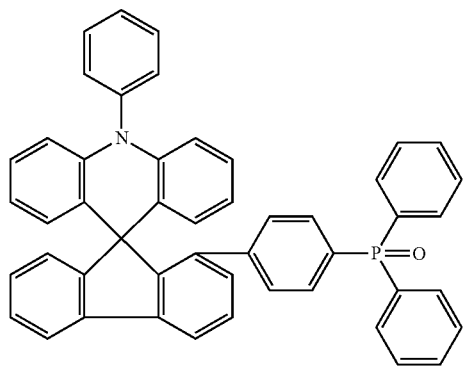
7-58
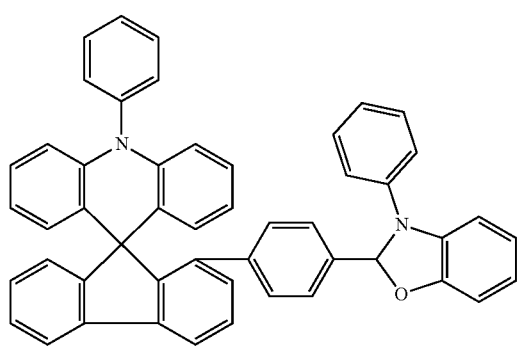
7-59
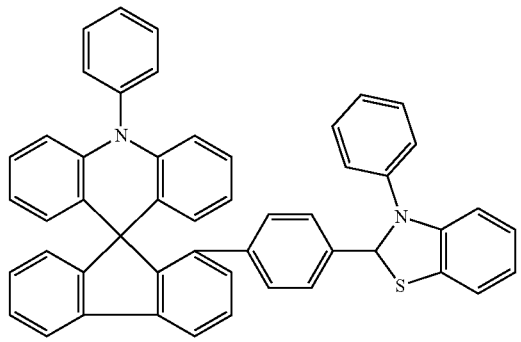
7-60
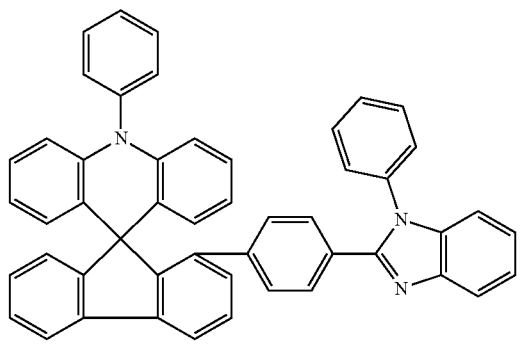
7-61
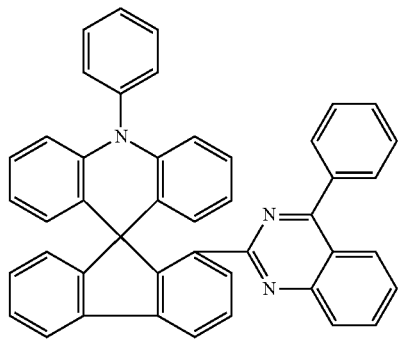
7-62
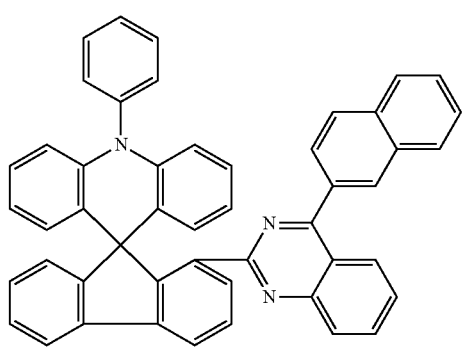

7-63
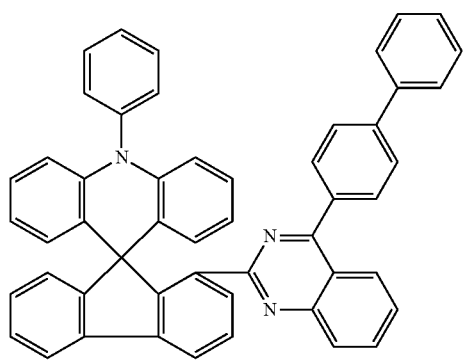
7-64
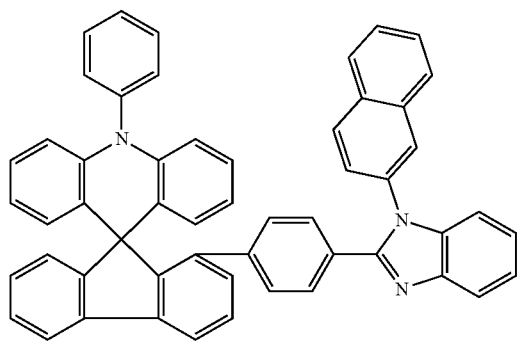
7-65
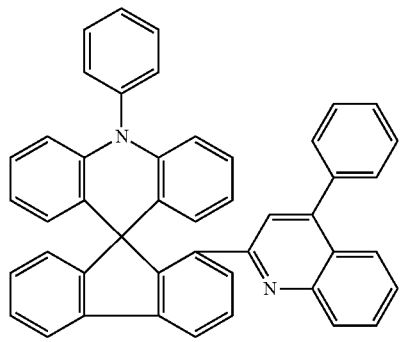
7-66
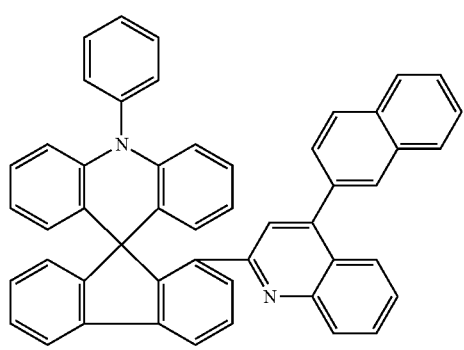
7-67
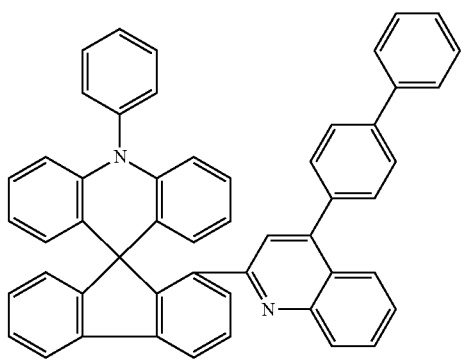
7-68
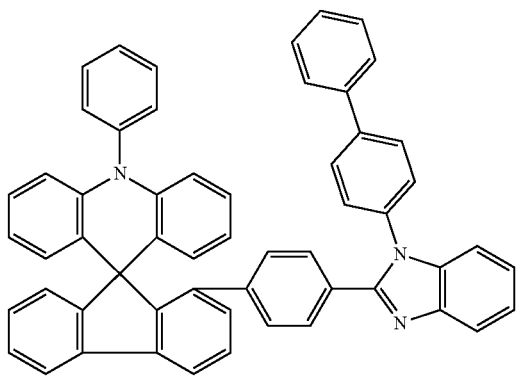
7-69
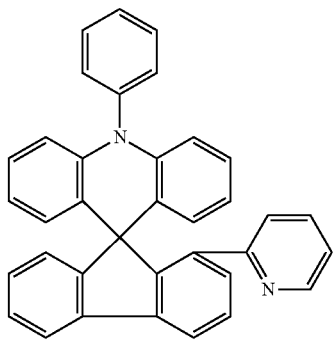
7-70
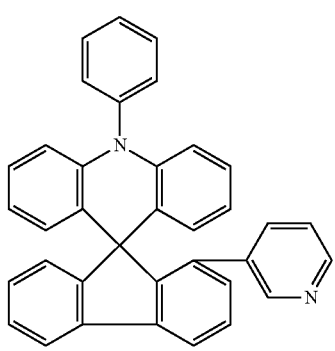

7-71
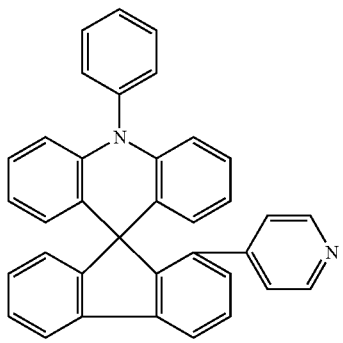
7-72
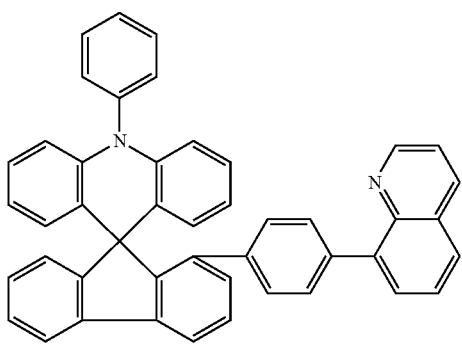
7-73
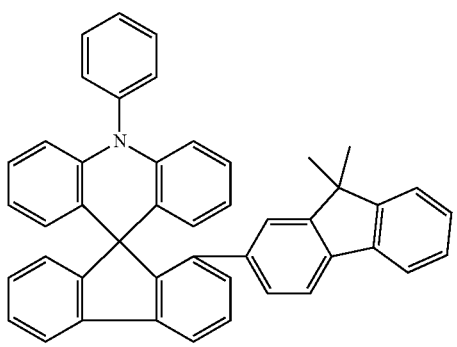
7-74
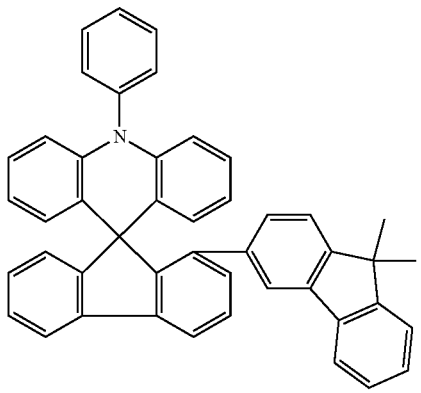
7-75
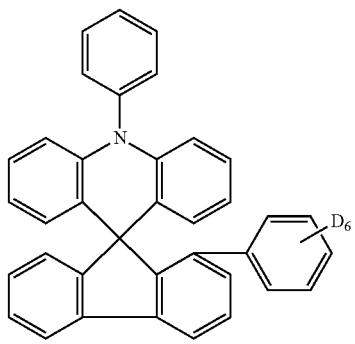
7-76
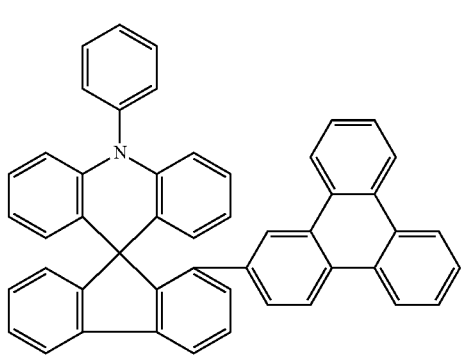
7-77
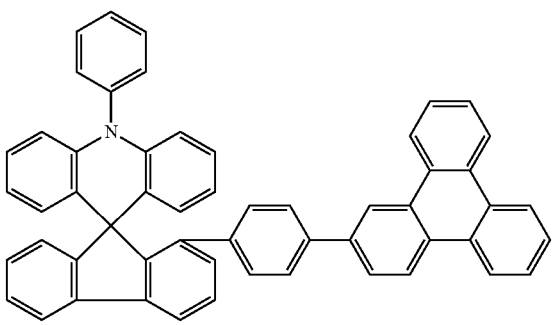
7-78
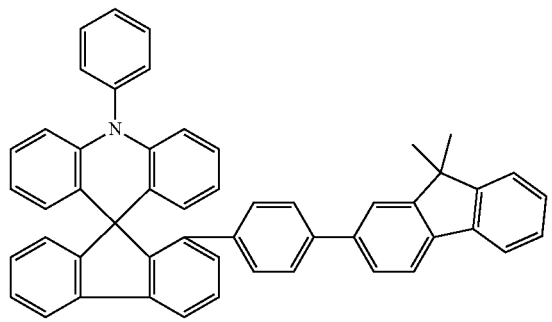

7-79
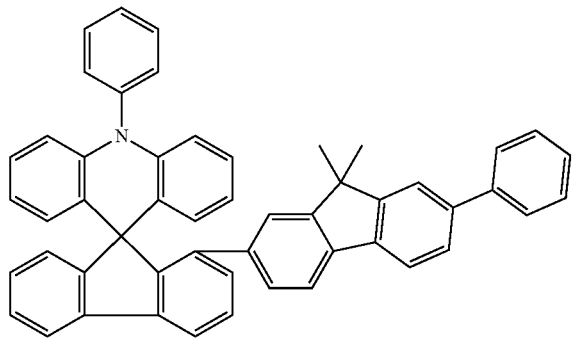
7-80
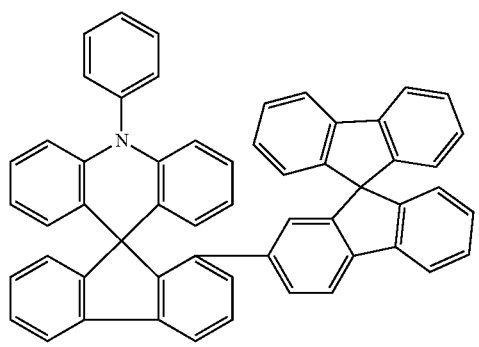
7-81
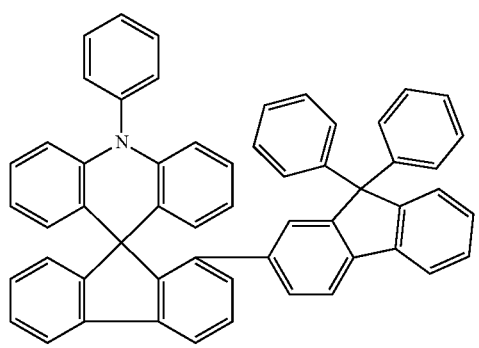
7-82
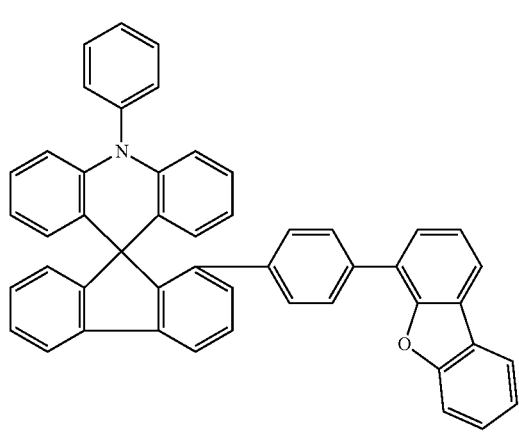
7-83
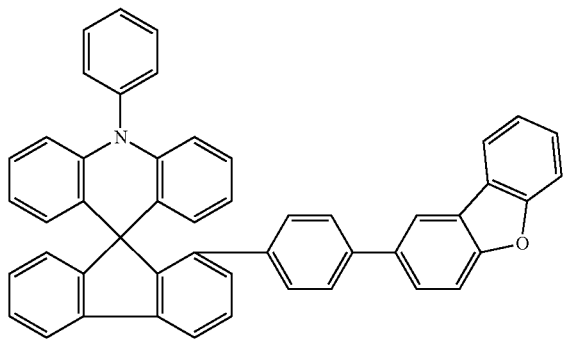
7-84
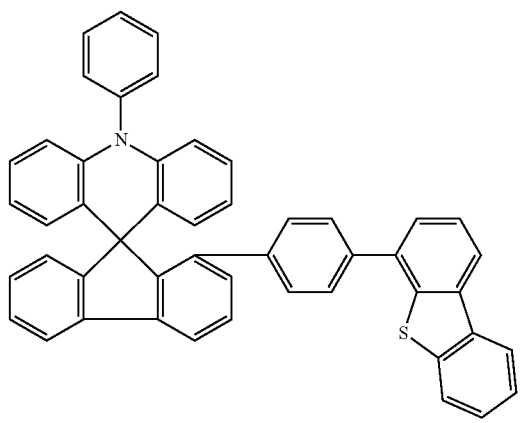
8-1
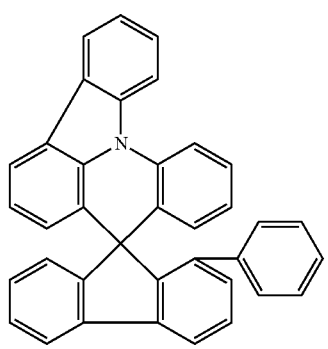
8-2

-continued
8-3
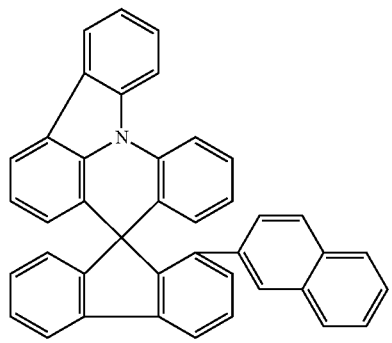
8-4
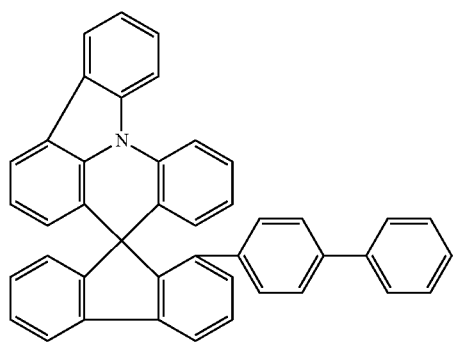
8-5
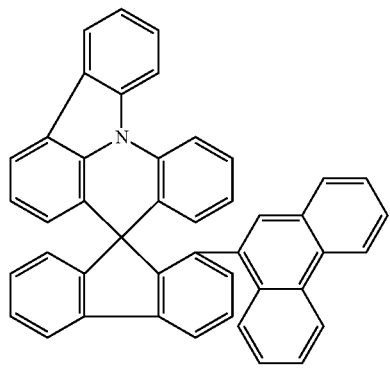
8-6
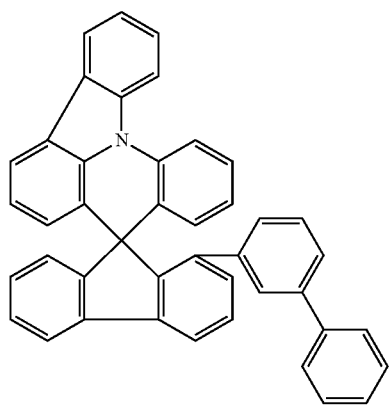
-continued
8-7
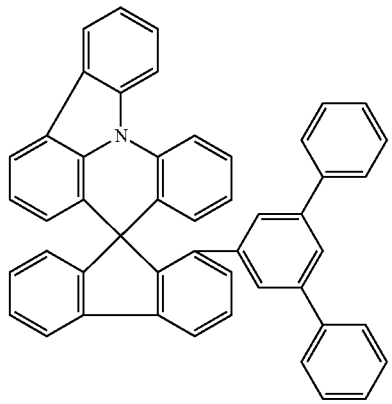
8-8
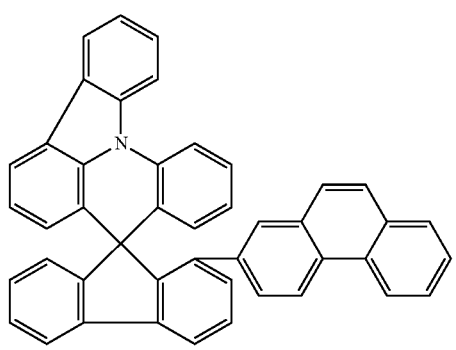
8-9
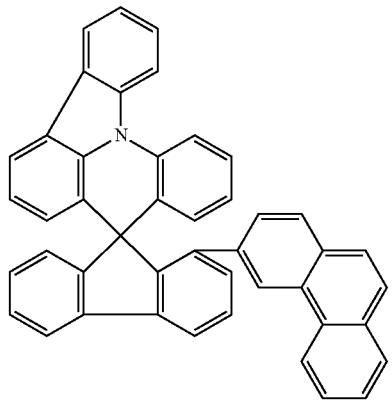
8-10
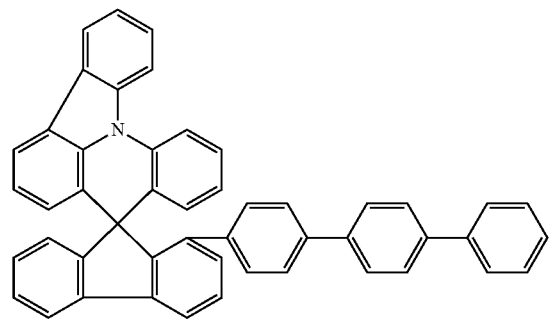

8-11
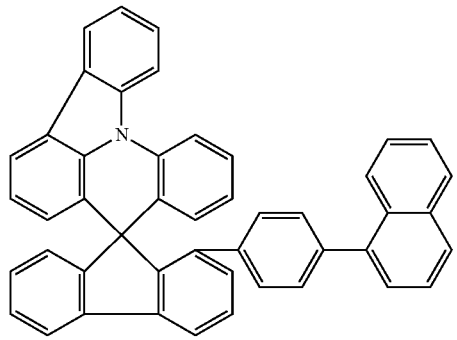
8-15
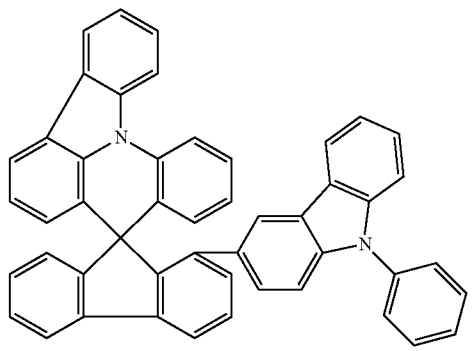
8-12
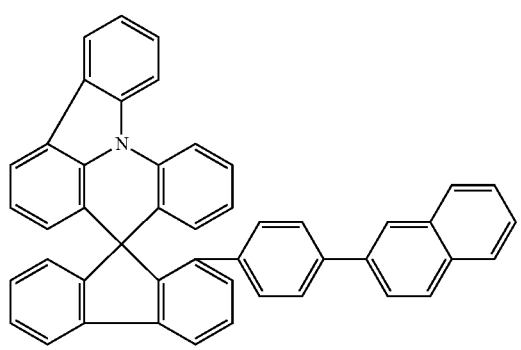
8-16
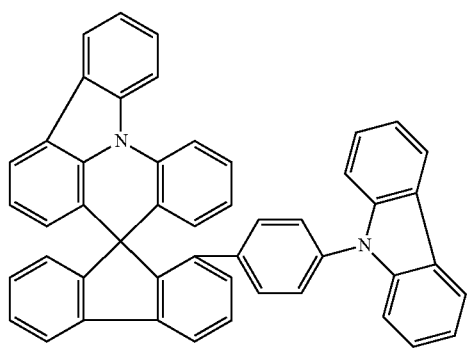
8-13
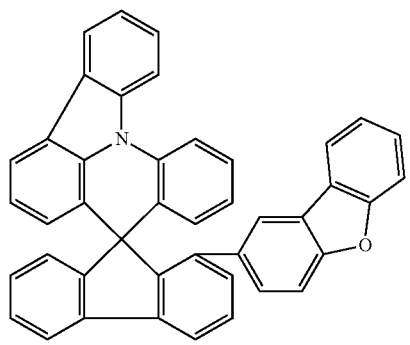
8-17
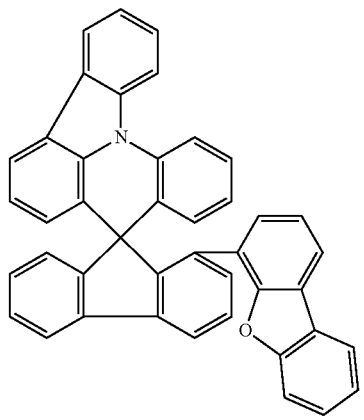
8-14
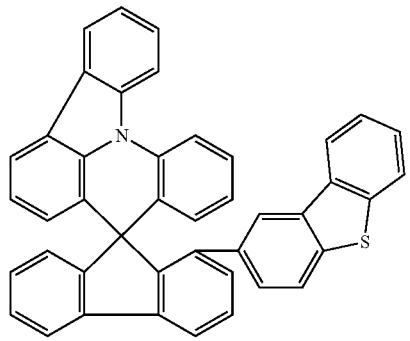
8-18
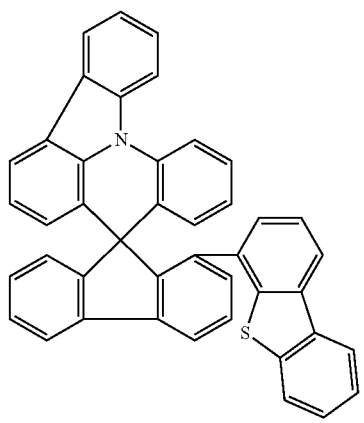

8-19
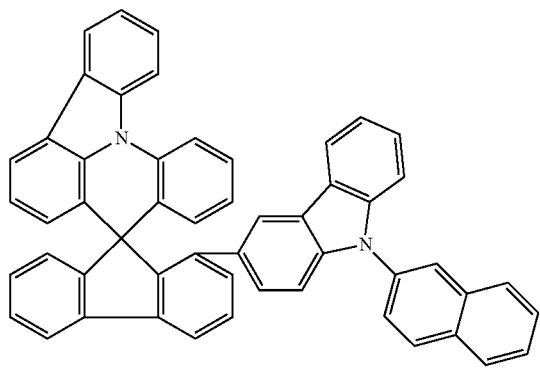
8-20
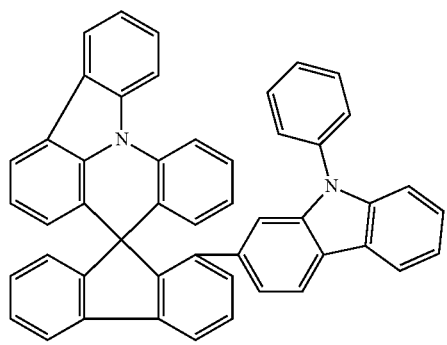
8-21
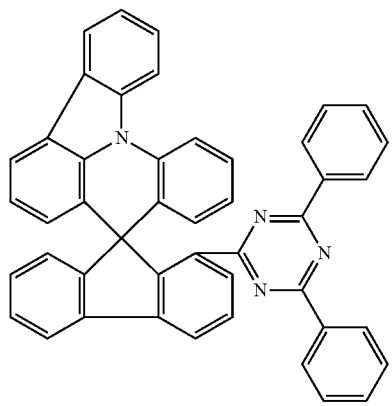
8-22
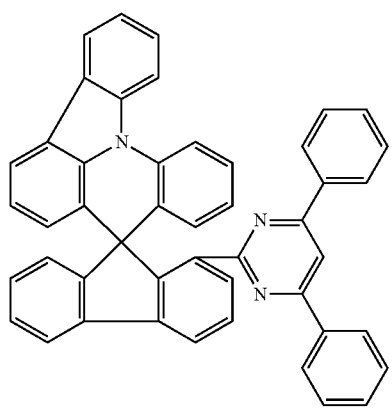
8-23
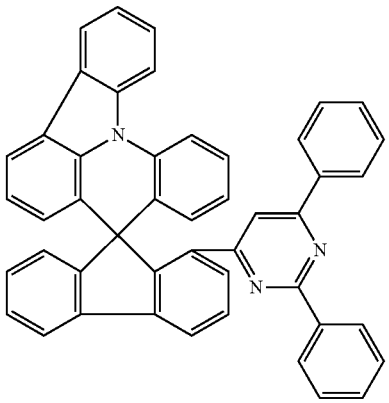
8-24
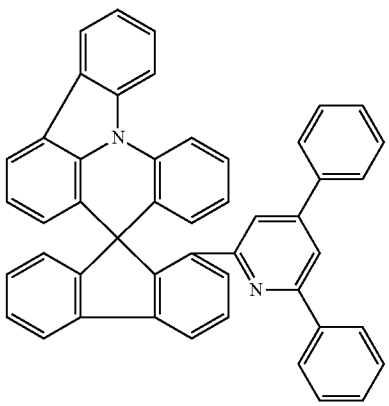
8-25
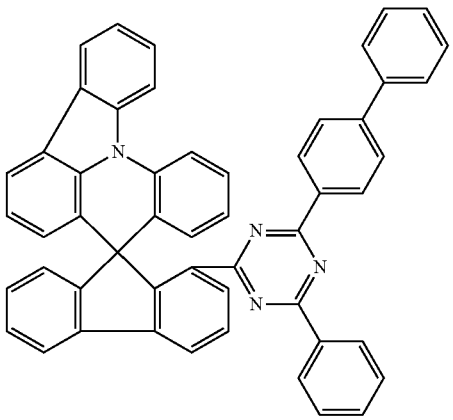

8-26
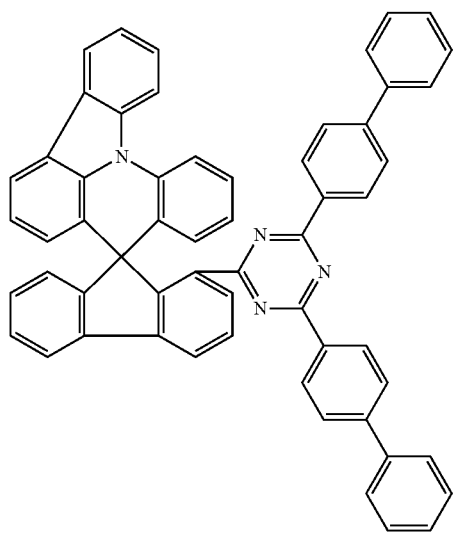
8-27
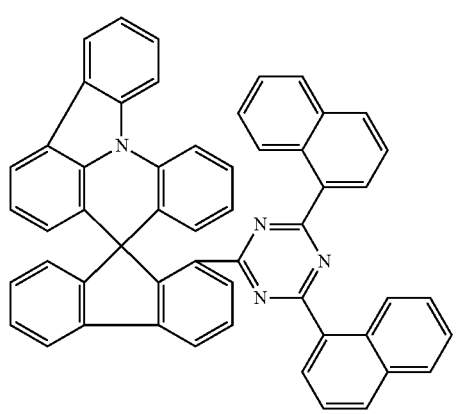
8-28
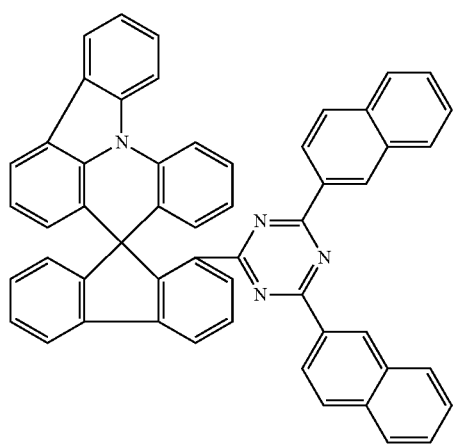
8-29
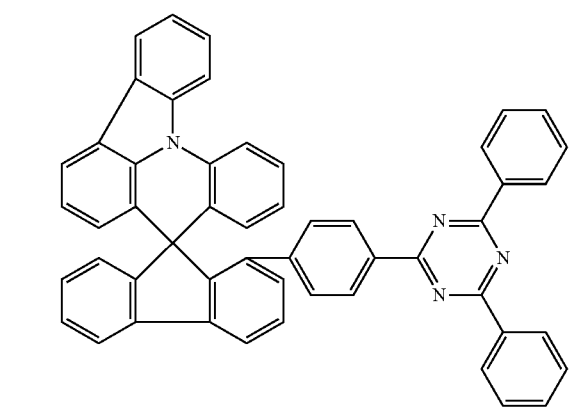
8-30
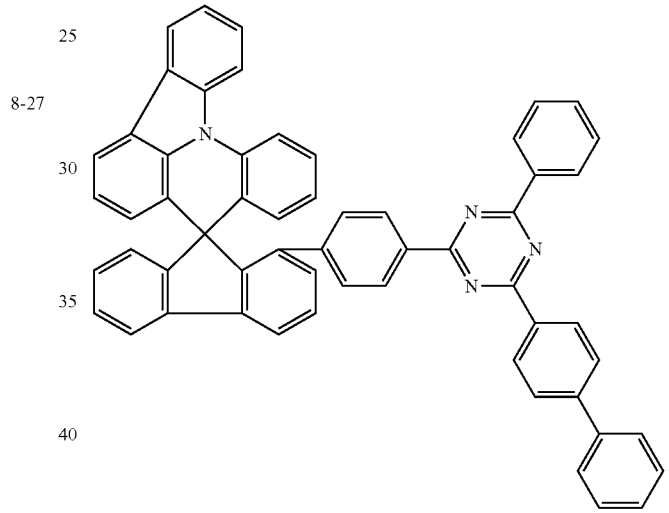
8-31
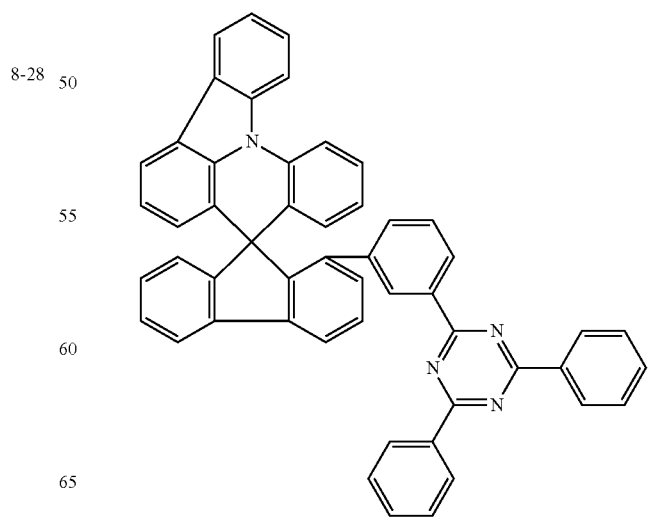

-continued
8-32
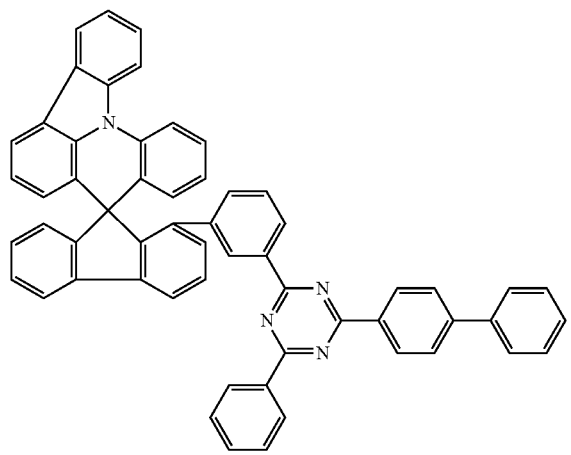
8-33
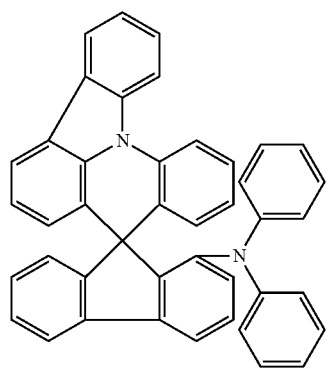
8-34
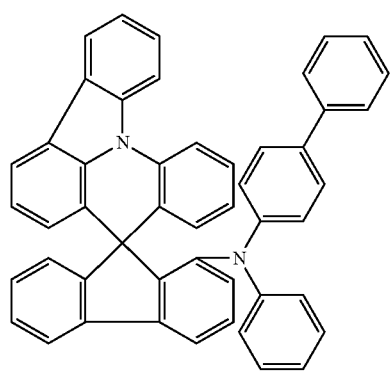
-continued
8-35
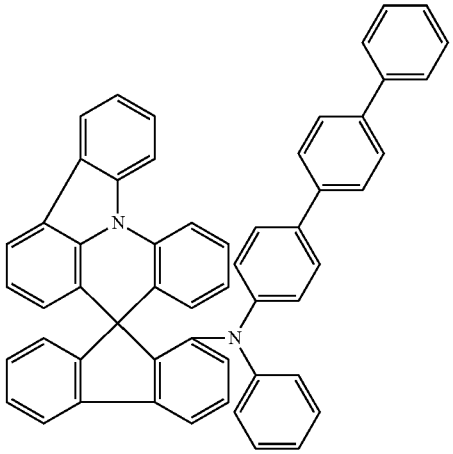
8-36
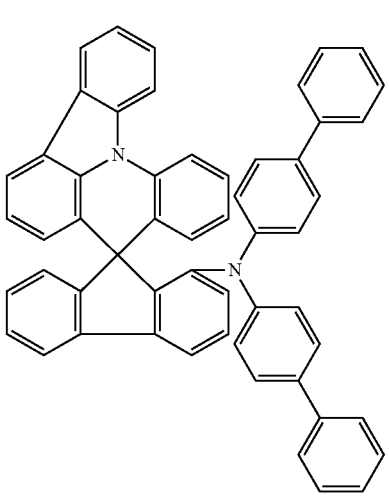
8-39
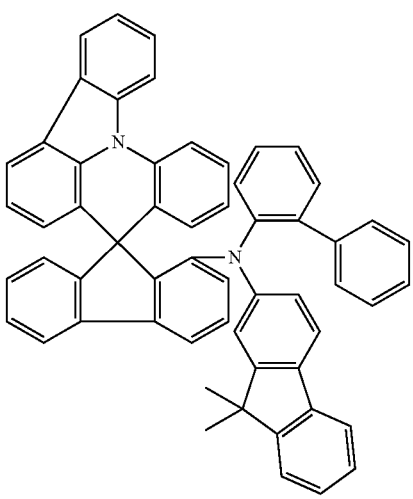

8-40
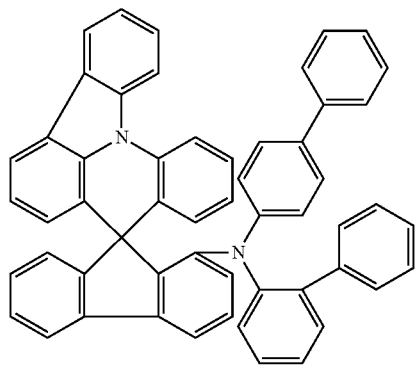
8-41
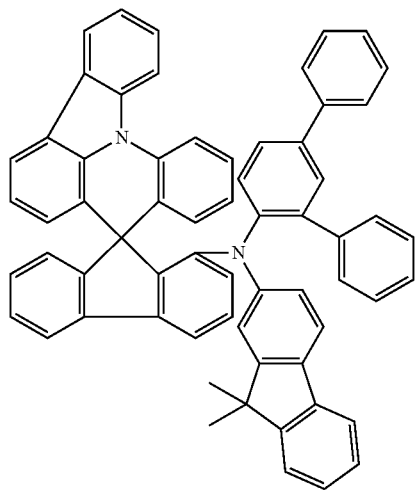
8-42
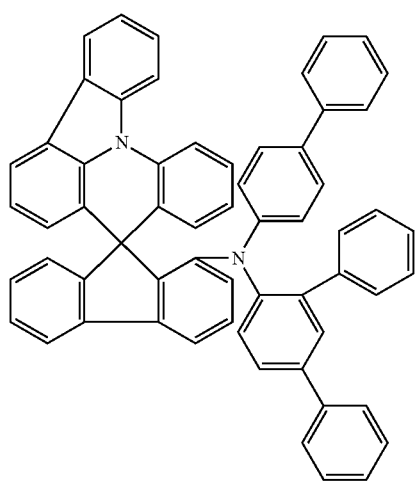
8-43
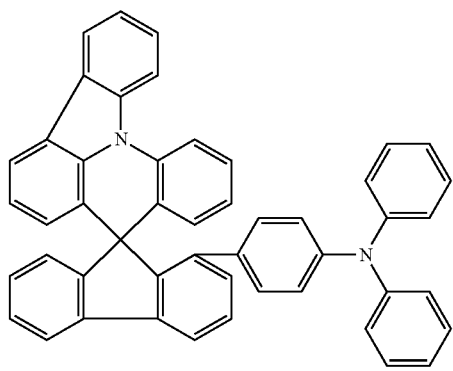
8-44
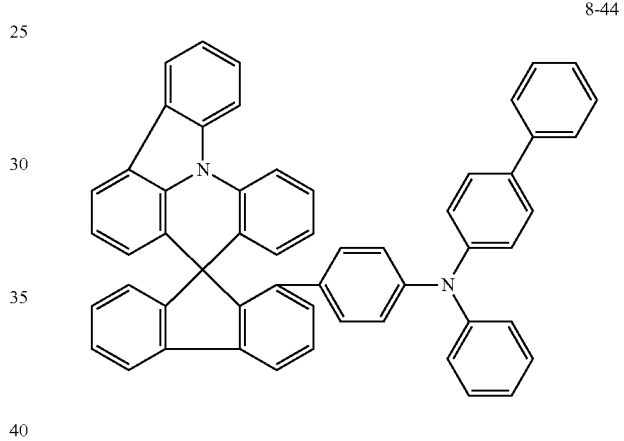
8-45
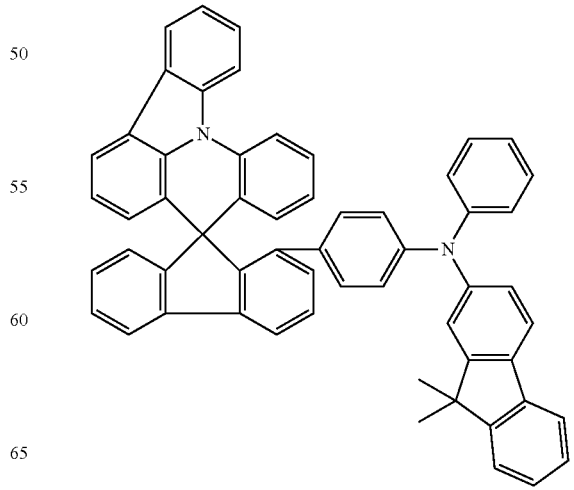

8-46
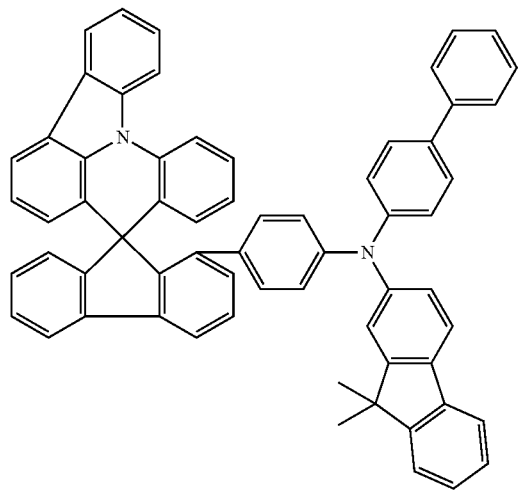
8-47
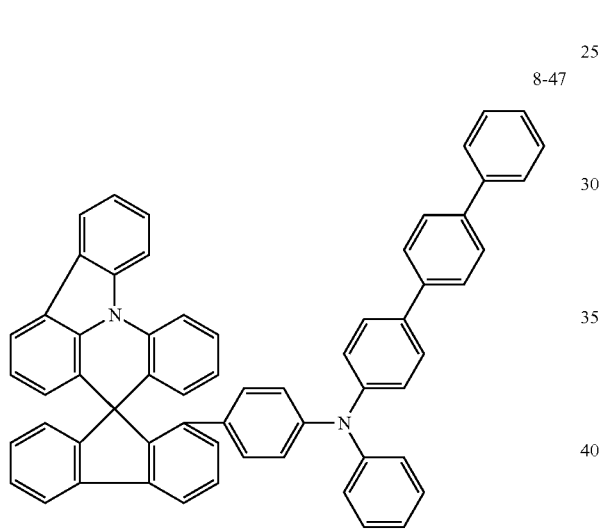
8-48
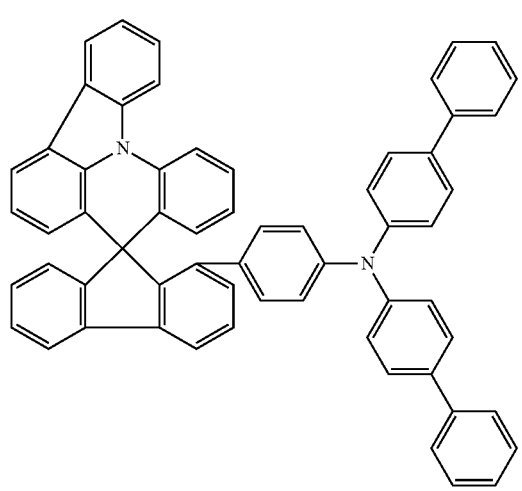
8-49
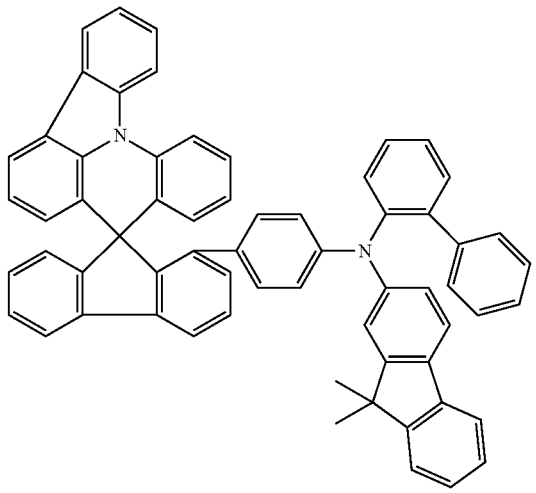
8-50
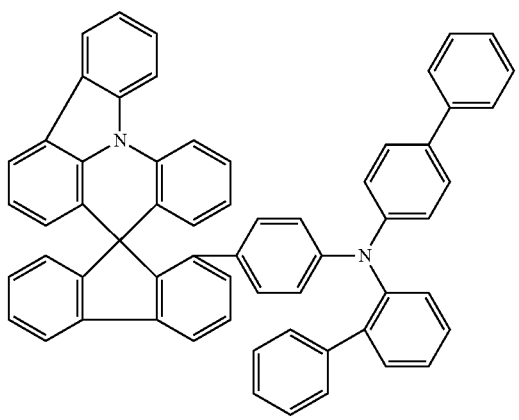
8-51
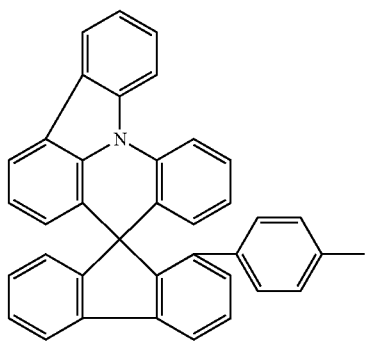
8-52

8-53
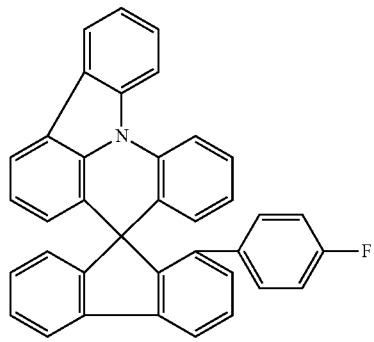
8-54
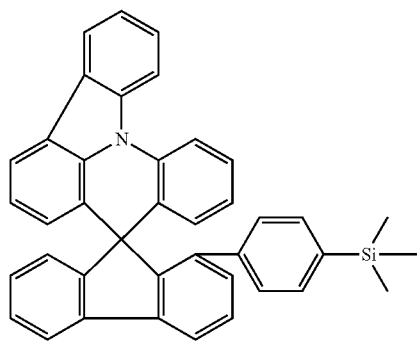
8-55
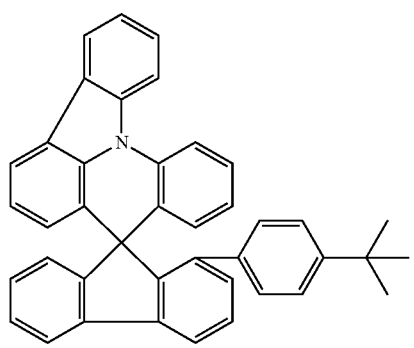
8-56
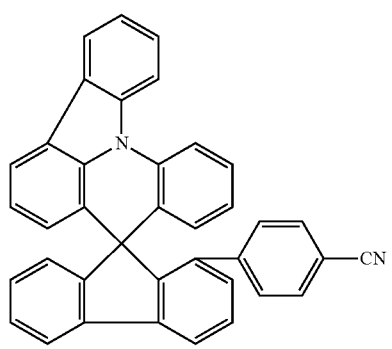
8-57
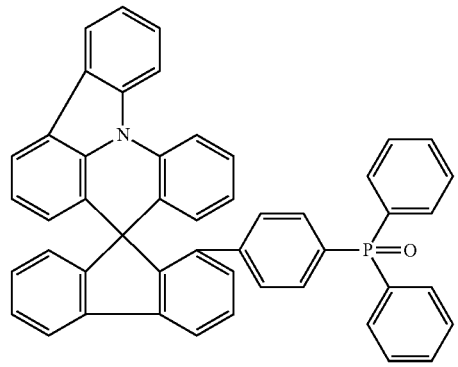
8-58
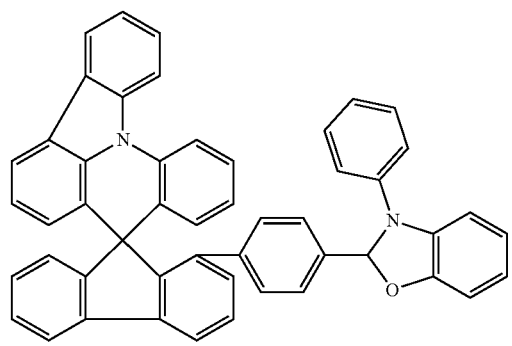
8-59
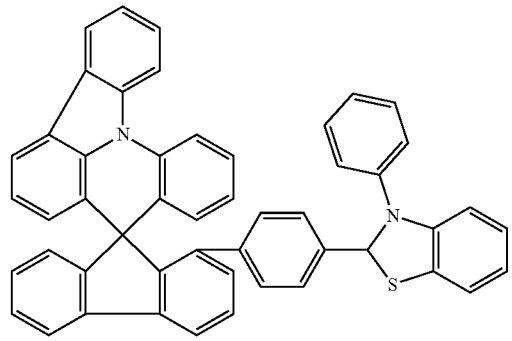
8-60
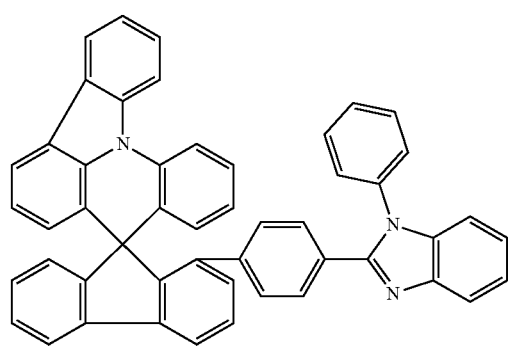

8-61
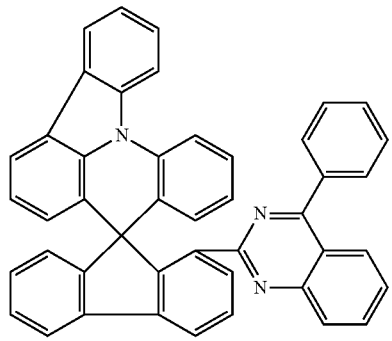
8-62
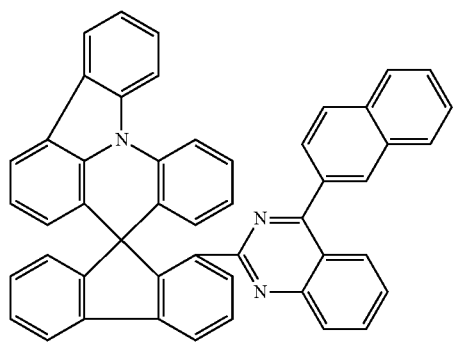
8-63
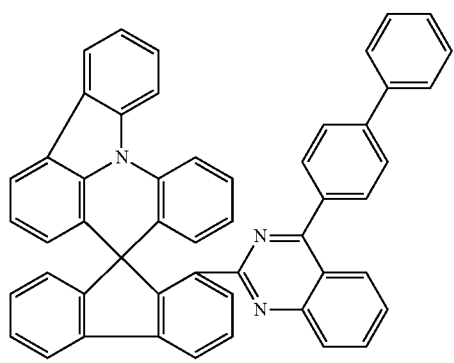
8-64
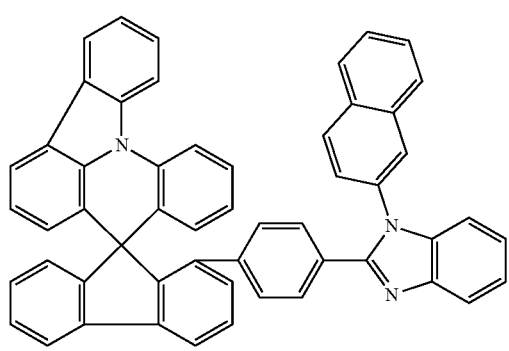
8-65
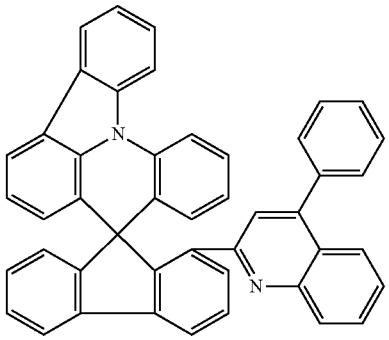
8-66
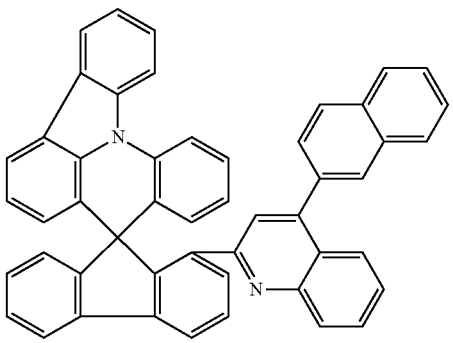
8-67
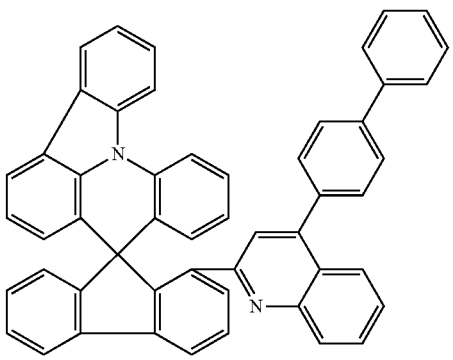
8-68
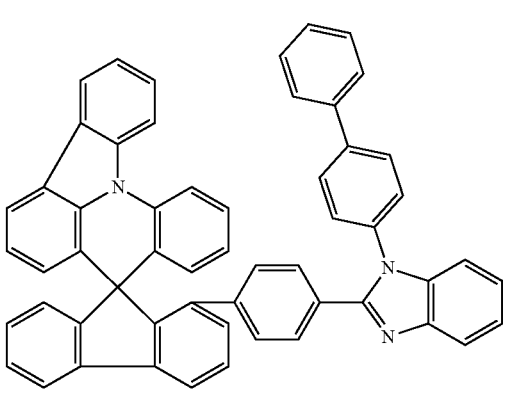

8-69
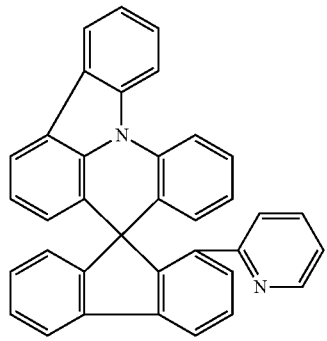
8-70
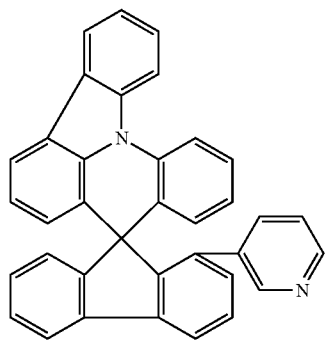
8-71
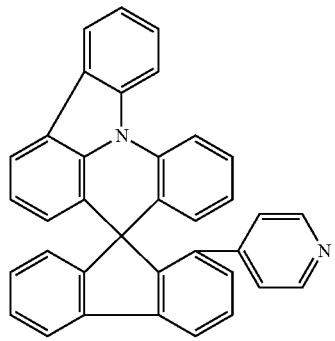
8-72
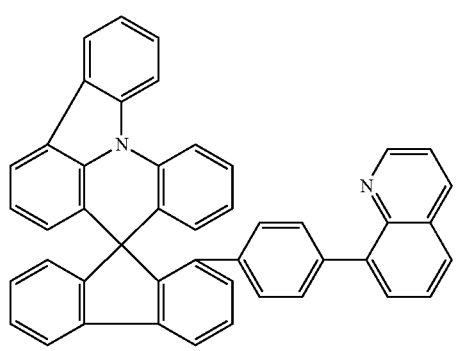
8-73
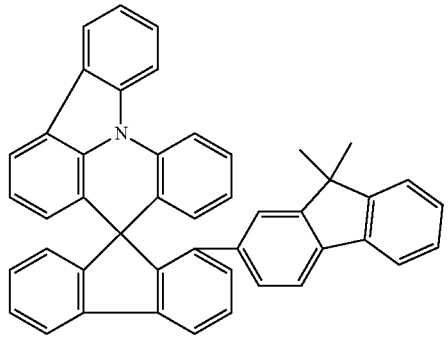
8-74
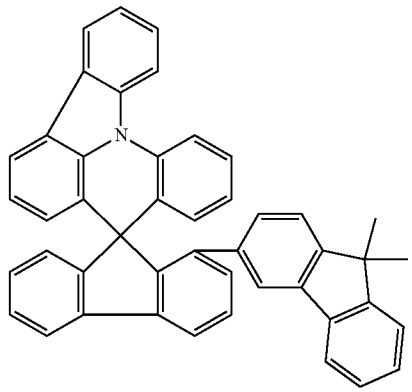
8-75
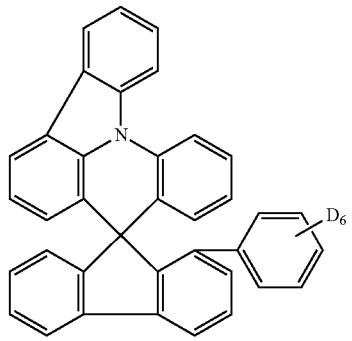
8-76
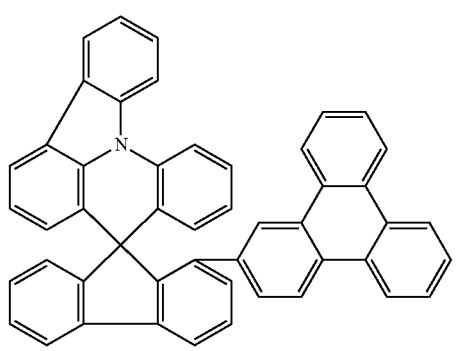

-continued
8-77
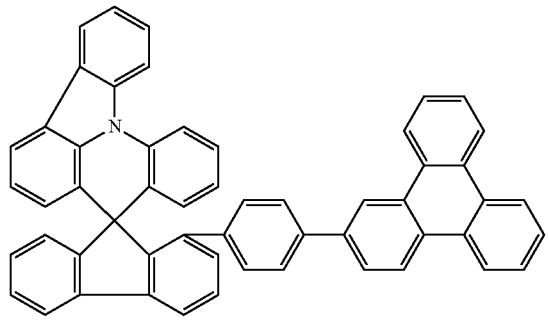
8-78
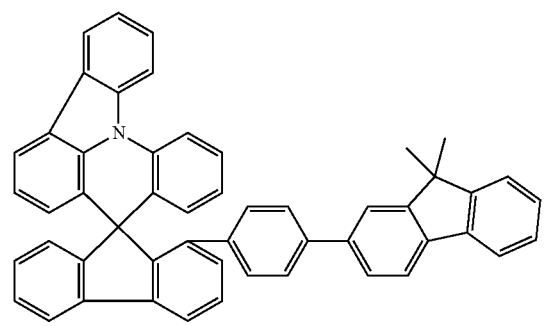
8-79
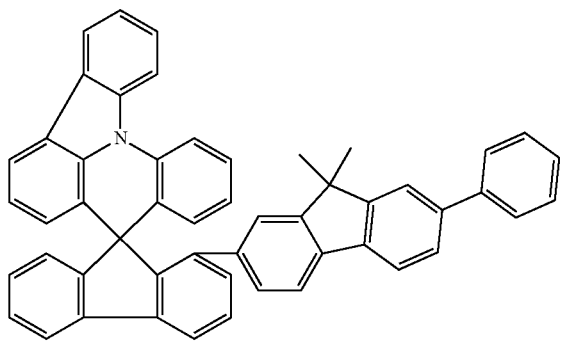
8-80
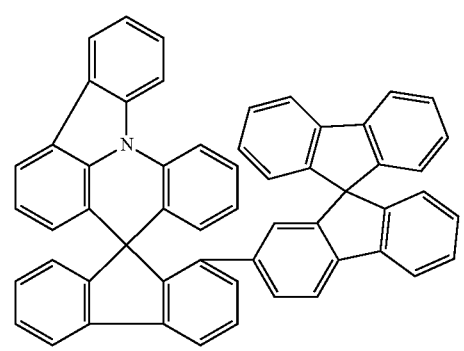
-continued
8-81
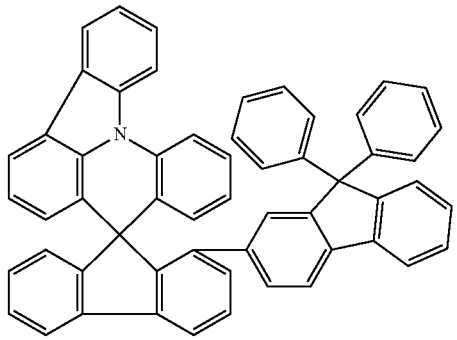
8-82
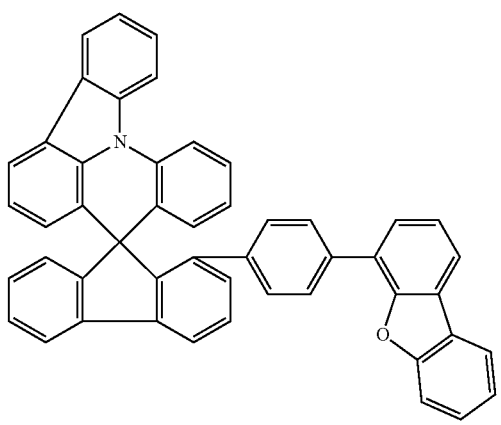
8-83
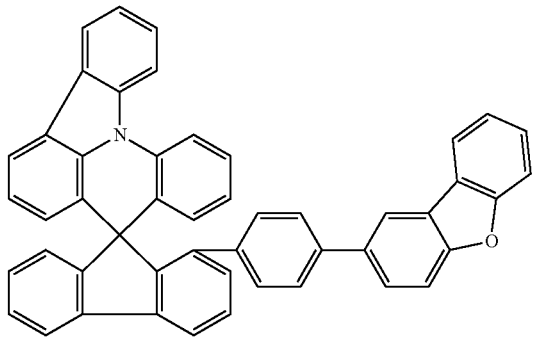
8-84
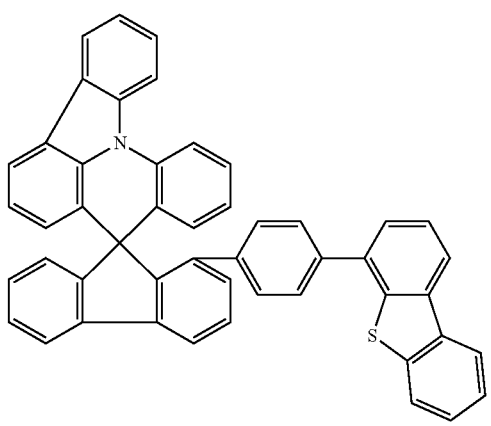

8-85
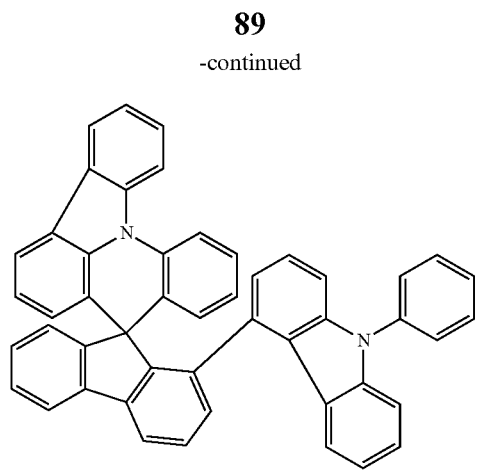
SYNTHESIS EXAMPLES
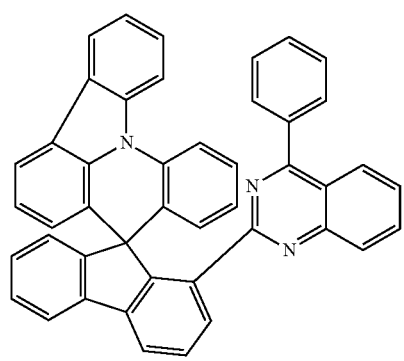
8-86
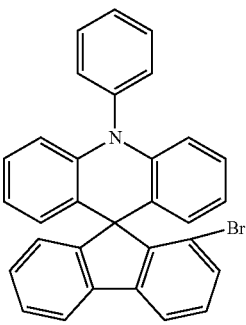
A
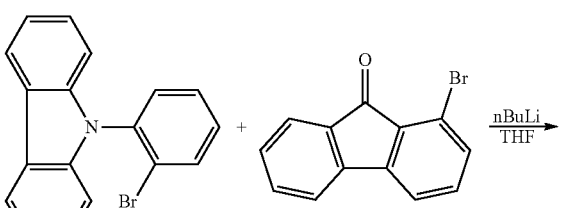
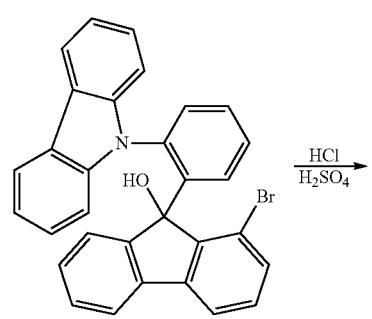
B
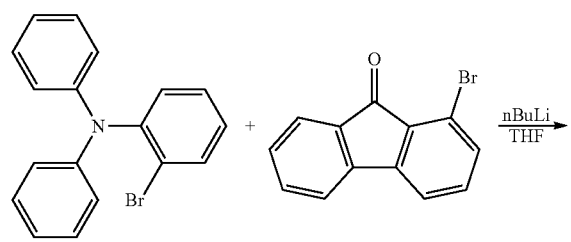
A     B
$\text{Ar}_1\text{—L}_1\text{—B(OH)}_2 \xrightarrow[\text{THF/H}_2\text{O, reflux}]{\text{Pd(PPh}_3)_4,\ K_2CO_3}$
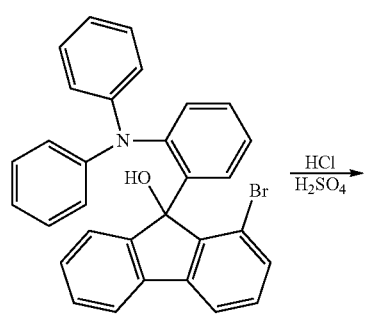

-continued

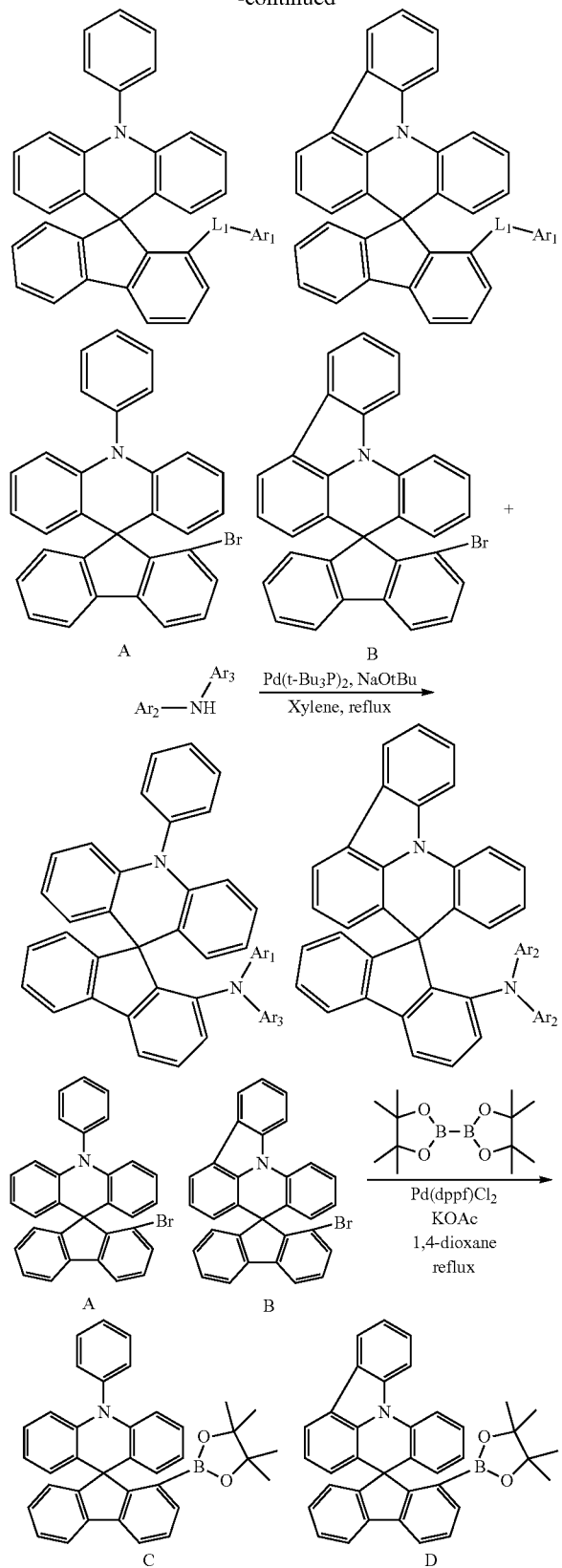

The reaction formulae relate to an example in which a specific substituent is introduced, but the person skilled in the art may not introduce a substituent by using the technology known in the art, if necessary, and when a substituent is introduced, the introduction may be performed by changing the kind or number of substituents. In addition, the person skilled in the art may perform the introduction by changing the samples, reaction conditions, or starting materials of the following reaction formulae using the technology known in the art.

Furthermore, the present specification provides an organic light emitting device including the compound represented by Chemical Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transport layer, a light emitting layer, an electron transport layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transport layer, or a layer which injects and transports holes simultaneously, and the hole injection layer, the hole transport layer, or the layer which injects and transports holes simultaneously includes the compound of Chemical Formula 1.

In another exemplary embodiment, the organic material layer includes a light emitting layer, and the light emitting layer includes the compound of Chemical Formula 1.

In an exemplary embodiment of the present specification, the light emitting layer includes the compound of Chemical Formula 1 and further includes a light emitting dopant.

In another exemplary embodiment, the light emitting dopant includes a fluorescent dopant or a phosphorescent dopant.

In still another exemplary embodiment, the phosphorescent dopant includes an iridium-based phosphorescent dopant.

In yet another exemplary embodiment, the phosphorescent dopant material includes Ir(ppy)$_3$ or (piq)$_2$Ir(acac).

In an exemplary embodiment of the present specification, the organic material layer includes an electron transport layer or an electron injection layer, and the electron transport layer or the electron injection layer includes the compound of Chemical Formula 1.

In an exemplary embodiment of the present specification, the organic material layer includes an electron blocking layer, and the electron blocking layer includes the compound of Chemical Formula 1.

In an exemplary embodiment of the present specification, the electron transport layer, the electron injection layer, or the layer which transports and injects electrons simultaneously includes the compound of Chemical Formula 1.

In another exemplary embodiment, the organic material layer includes a light emitting layer and an electron transport layer, and the electron transport layer includes the compound of Chemical Formula 1.

An exemplary embodiment of the present specification provides an organic light emitting device including: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the heterocyclic compound. In one exemplary embodiment, as the two or more organic material layers, two or more may be selected from the group consisting of an electron transport layer, an electron injection layer, a layer which transports and injects electrons simultaneously, and a hole blocking layer.

In an exemplary embodiment of the present specification, the organic material layer includes two or more electron transport layers, and at least one of the two or more electron transport layers includes the heterocyclic compound. Specifically, in an exemplary embodiment of the present specification, the heterocyclic compound may also be included in one layer of the two or more electron transport layers, and may be included in each of the two or more electron transport layers.

Further, in an exemplary embodiment of the present specification, when the heterocyclic compound is included in each of the two or more electron transport layers, the other materials except for the heterocyclic compound may be the same as or different from each other.

In another exemplary embodiment, the organic light emitting device may be an organic light emitting device having a structure (normal type) in which a positive electrode, one or more organic material layers, and a negative electrode are sequentially stacked on a substrate.

In still another exemplary embodiment, the organic light emitting device may be an organic light emitting device having a reverse-direction structure (inverted type) in which a negative electrode, one or more organic material layers, and a positive electrode are sequentially stacked on a substrate.

Figure 2:
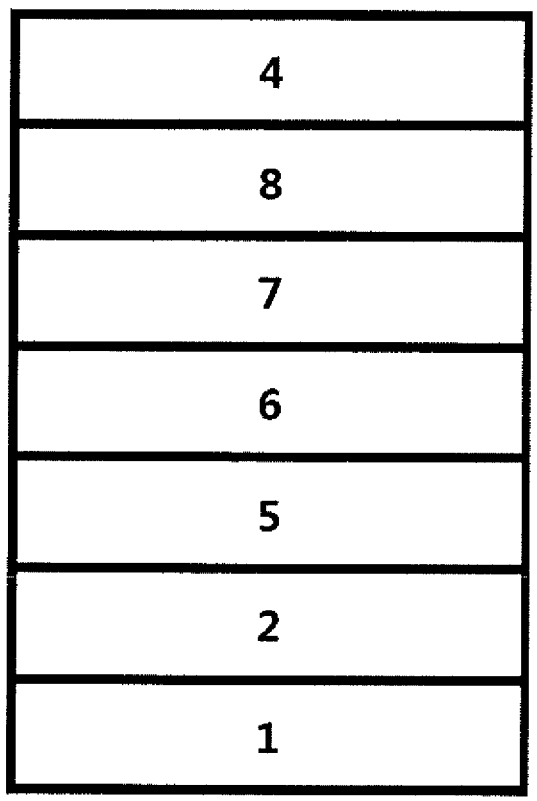
FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4.

For example, the structure of the organic light emitting device according to an exemplary embodiment of the present specification is exemplified in FIGS. 1 and 2.

FIG. 1 illustrates an example of an organic light emitting device composed of a substrate 1, a positive electrode 2, a light emitting layer 3, and a negative electrode 4. In the structure as described above, the compound may be included in the light emitting layer.

FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4. In the structure as described above, the compound may be included in one or more layers of the hole injection layer, the hole transport layer, the light emitting layer, and the electron transport layer.

The organic light emitting device of the present specification may be manufactured by the materials and methods known in the art, except that one or more layers of the organic material layers include the compound of the present specification, that is, the compound of Chemical Formula 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layers include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as $ZnO:Al$ or $SnO_2:Sb$; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as $LiF/Al$ or $LiO_2/Al$, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

According to an exemplary embodiment of the present specification, the organic material layer includes the light emitting layer, and the light emitting layer includes a compound represented by the following Chemical Formula 1-A.

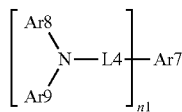

[Chemical Formula 1-A]

in Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L4 is a direct bond.

According to an exemplary embodiment of the present specification, n1 is 2.

In an exemplary embodiment of the present specification, Ar7 is a divalent pyrene group which is unsubstituted or substituted with deuterium, a methyl group, an ethyl group, or a tert-butyl group.

According to an exemplary embodiment of the present specification, Ar8 and Ar9 are the same as or different from each other, and are each independently a substituted or unsubstituted aryl group having 6 to 30 carbon atoms.

According to an exemplary embodiment of the present specification, Ar8 and Ar9 are the same as or different from each other, and are each independently an aryl group which is unsubstituted or substituted with a germanium group substituted with an alkyl group.

According to an exemplary embodiment of the present specification, Ar8 and Ar9 are the same as or different from each other, and are each independently an aryl group which is unsubstituted or substituted with a trimethylgermanium group.

According to an exemplary embodiment of the present specification, Ar8 and Ar9 are the same as or different from each other, and are each independently a substituted or unsubstituted phenyl group.

According to an exemplary embodiment of the present specification, Ar8 and Ar9 are a phenyl group which is unsubstituted or substituted with a trimethylgermanium group.

According to an exemplary embodiment of the present specification, Chemical Formula 1-A is represented by the following compound.

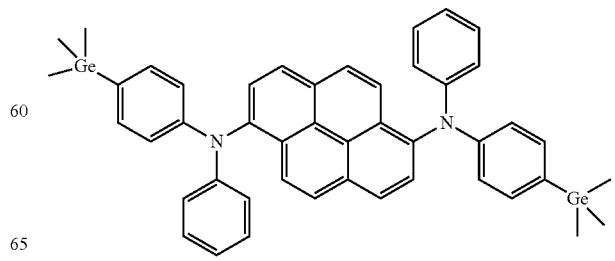

According to an exemplary embodiment of the present specification, the organic material layer includes a light emitting layer, and the light emitting layer includes a compound represented by the following Chemical Formula 2-A.

[Chemical Formula 2-A]

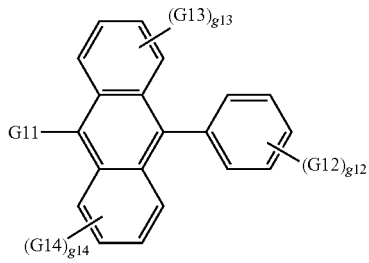

In Chemical Formula 2-A,

G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

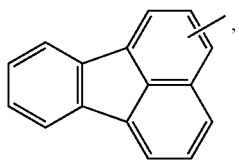

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, G11 is a 1-naphthyl group.

According to an exemplary embodiment of the present specification, G12 is a 2-naphthyl group.

According to an exemplary embodiment of the present specification, G13 and G14 are hydrogen.

According to an exemplary embodiment of the present specification, Chemical Formula 2-A is represented by the following compound.

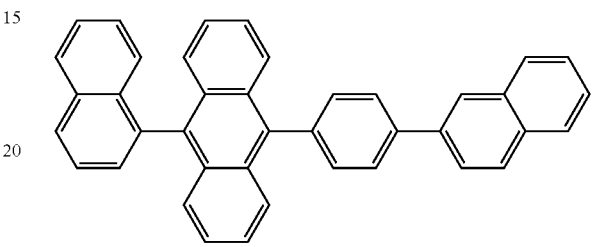

The organic light emitting device of the present specification may be manufactured by the materials and methods known in the art, except that one or more layers of the organic material layers include the heterocyclic compound of the present specification, that is, the heterocyclic compound represented by Chemical Formula 1.

When the organic light emitting device includes a plurality of organic material layers, the organic material layers may be formed of the same material or different materials.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material is suitably a material which may inject electrons well from a negative electrode and may transfer the electrons to a light emitting layer, and has large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Chemical Formula 1 may be included in an organic solar cell or an organic transistor in addition to an organic light emitting device.

The preparation of the compound represented by Chemical Formula 1 and the organic light emitting device including the same will be specifically described in the following Examples. However, the following Examples are provided for exemplifying the present specification, and the scope of the present specification is not limited thereby.

PREPARATION EXAMPLES

Synthesis Examples

The reaction formulae relate to an example in which a specific substituent is introduced, but the person skilled in the art may not introduce a substituent by using the technology known in the art, if necessary, and when a substituent is introduced, the introduction may be performed by changing the kind or number of substituents. Further, the person skilled in the art may perform the introduction by changing the samples, reaction conditions, or starting materials of the following reaction formulae using the technology known in the art.

<Preparation Example 1> Synthesis of the Following Compound 1-1

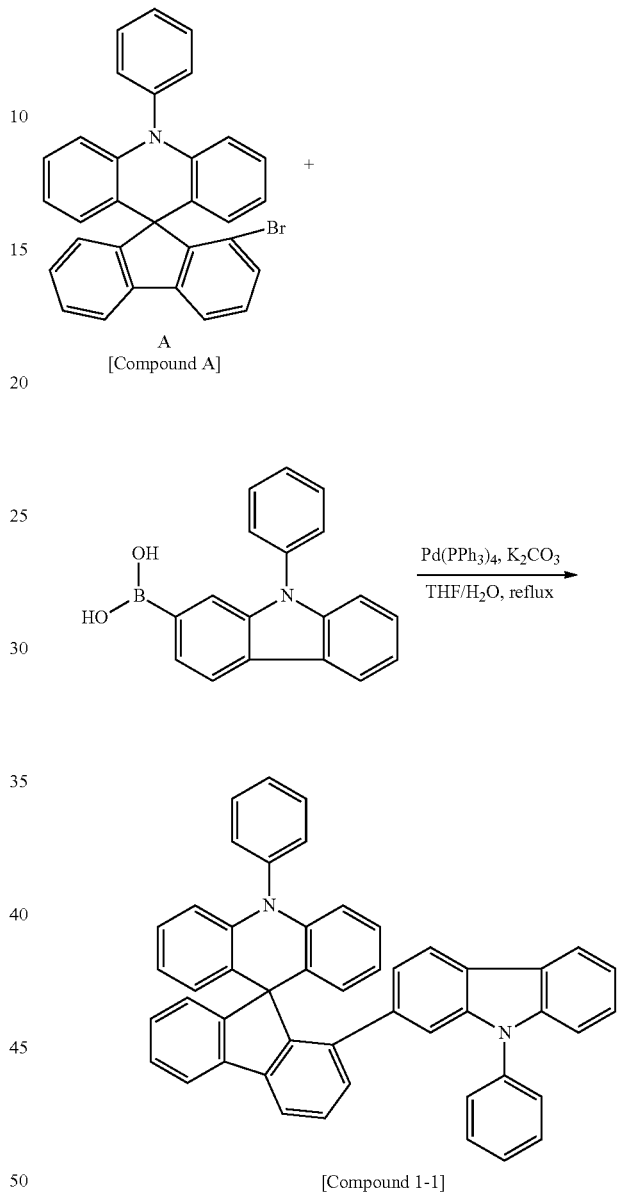

Compound A (10.0 g, 20.62 mmol) and (9-phenyl-9H-carbazol-2-yl)boronic acid (6.51 g, 22.68 mmol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.69 g, 0.61 mmol) was put thereinto, and then the resulting mixture was heated and stirred for 3 hours. The temperature was lowered to normal temperature, the aqueous layer was removed, and the resulting product was dried over anhydrous magnesium sulfate, and then concentrated under reduced pressure, and recrystallized with 230 ml of ethyl acetate to prepare Compound 1-1 (10.18 g, yield: 76%).

MS[M+H]$^+$=649

<Preparation Example 2> Synthesis of the Following Compound 1-2

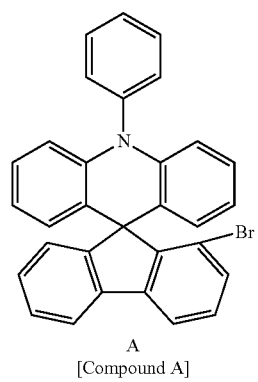
[Compound A]

+

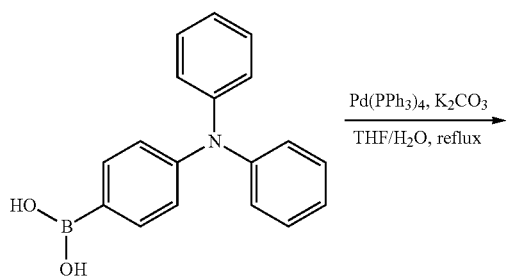

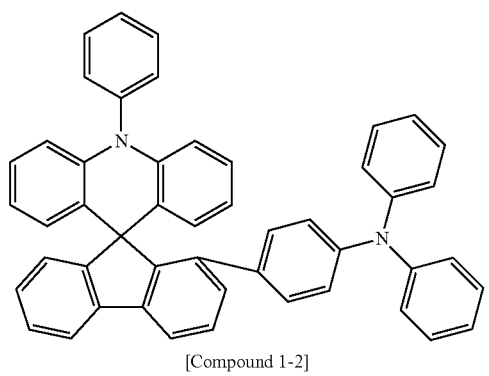

[Compound 1-2]

Compound A (10.0 g, 20.62 mmol) and (4-(diphenylamino)phenyl)boronic acid (6.51 g, 22.68 mmol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.69 g, 0.61 mmol) was put thereinto, and then the resulting mixture was heated and stirred for 3 hours. The temperature was lowered to normal temperature, the aqueous layer was removed, and the resulting product was dried over anhydrous magnesium sulfate, and then concentrated under reduced pressure, and recrystallized with 230 ml of ethyl acetate to prepare Compound 1-2 (10.18 g, yield: 76%).

MS[M+H]$^+$=651

<Preparation Example 3> Synthesis of the Following Compound 1-3

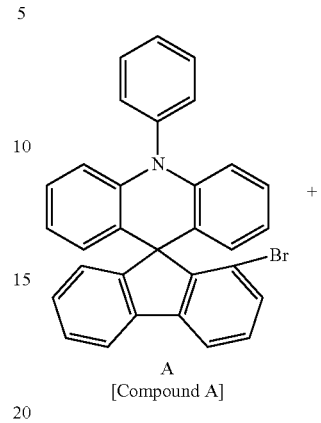
[Compound A]

+

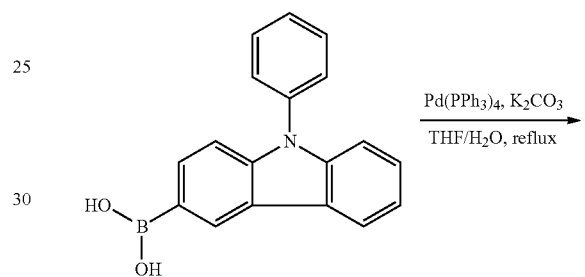

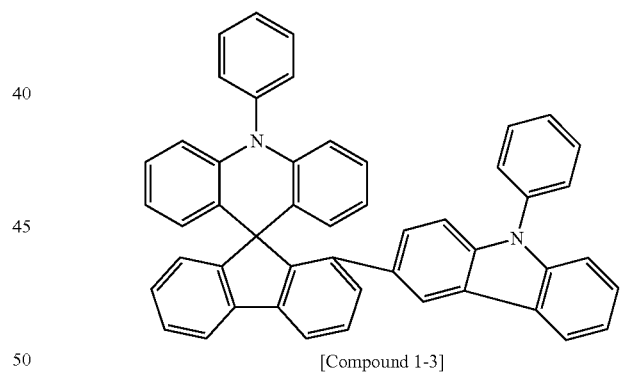

[Compound 1-3]

Compound A (10.0 g, 20.62 mmol) and (4-(diphenylamino)phenyl)boronic acid (6.51 g, 22.68 mmol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.69 g, 0.61 mmol) was put thereinto, and then the resulting mixture was heated and stirred for 3 hours. The temperature was lowered to normal temperature, the aqueous layer was removed, and the resulting product was dried over anhydrous magnesium sulfate, and then concentrated under reduced pressure, and recrystallized with 230 ml of ethyl acetate to prepare Compound 1-3 (10.18 g, yield: 76%).

MS[M+H]$^+$=649

<Preparation Example 4> Synthesis of the Following Compound 1-4

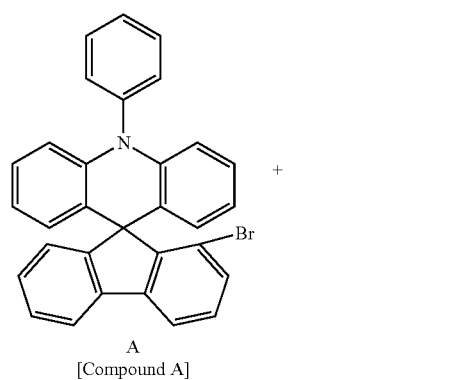

<Preparation Example 5> Synthesis of the Following Compound 1-5

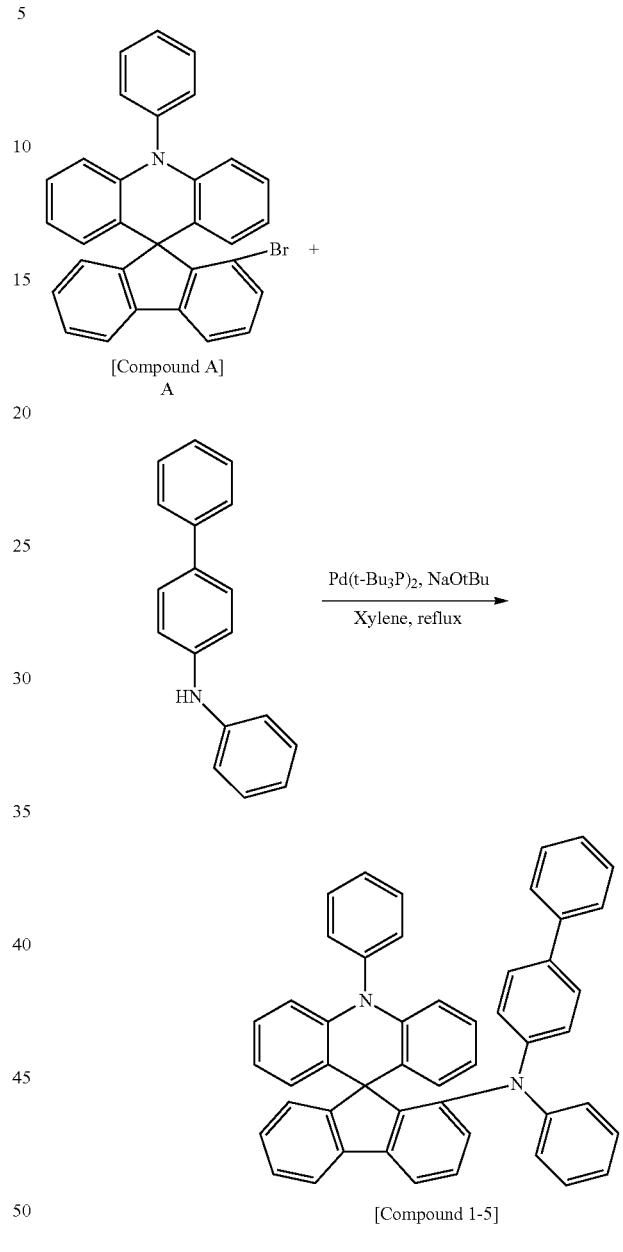

Compound A (10.0 g, 20.62 mmol) and diphenylamine (3.82 g, 22.68 mmol) were completely dissolved in 220 ml of xylene in a 500-ml round bottom flask under a nitrogen atmosphere, and then sodium tert-butoxide (2.58 g, 26.81 mol) was added thereto, bis(tri-tert-butylphosphine) palladium(0) (0.11 g, 0.21 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:20 to prepare Compound 1-4 (8.26 g, yield: 69%).

MS[M+H]$^+$=575

Compound A (10.0 g, 20.62 mmol) and N-phenyl-[1,1'-biphenyl]-4-amine(N-phenyl-[1,1'-biphenyl]-4-amine) (5.56 g, 22.68 mmol) were completely dissolved in 260 ml of xylene in a 500-ml round bottom flask under a nitrogen atmosphere, and then sodium tert-butoxide (2.58 g, 26.81 mol) was added thereto, bis(tri-tert-butylphosphine) palladium(0) (0.11 g, 0.21 mmol) was put thereinto, and then the resulting mixture was heated and stirred for 5 hours. The temperature was lowered to normal temperature, the mixture was filtered to remove the base, and then xylene was concentrated under reduced pressure, and the residue was columned at a ratio of tetrahydrofuran:hexane=1:20 to prepare Compound 1-5 (10.95 g, yield: 82%).

MS[M+H]$^+$=651

105

<Preparation Example 6> Synthesis of the Following Compound 1-6

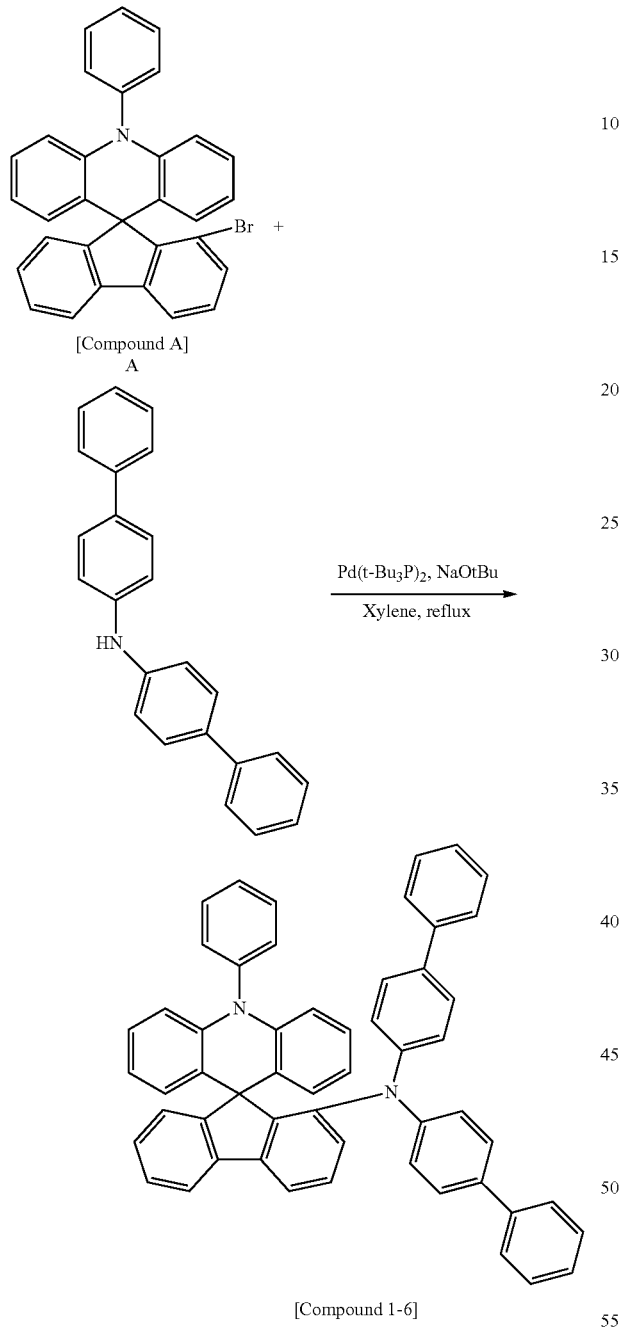

[Compound 1-6]

Compound A (10.0 g, 20.62 mmol) and di([1,1'-biphenyl]-4-yl)amine (7.28 g, 22.68 mmol) were completely dissolved in 240 ml of xylene in a 500-ml round bottom flask under a nitrogen atmosphere, and then sodium tert-butoxide (2.58 g, 26.81 mol) was added thereto, bis(tri-tert-butylphosphine) palladium(0) (0.11 g, 0.21 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:20 to prepare Compound 1-6 (12.05 g, yield: 81%).
MS[M+H]$^+$=727

106

<Preparation Example 7> Synthesis of the Following Compound 1-7

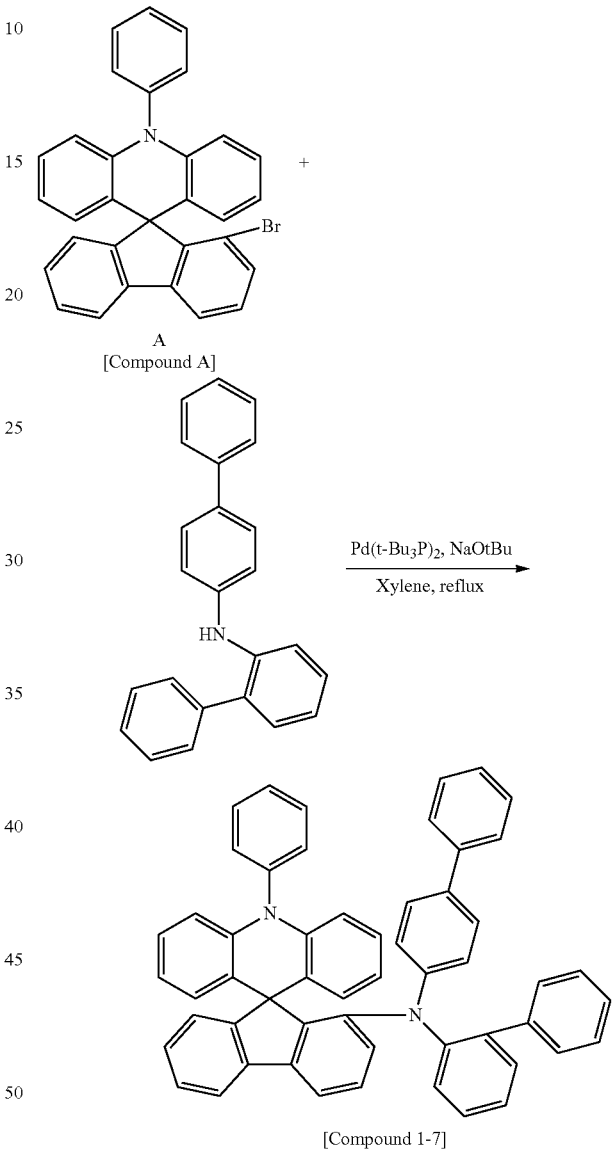

[Compound 1-7]

Compound A (10.0 g, 20.62 mmol) and N-([1,1'-biphenyl]-4-yl)-[1,1'-biphenyl]-2-amine (7.28 g, 22.68 mmol) were completely dissolved in 240 ml of xylene in a 500-ml round bottom flask under a nitrogen atmosphere, and then sodium tert-butoxide (2.58 g, 26.81 mol) was added thereto, bis(tri-tert-butylphosphine) palladium(0) (0.11 g, 0.21 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:20 to prepare Compound 1-6 (10.84 g, yield: 72%).
MS[M+H]$^+$=727

<Preparation Example 8> Synthesis of the Following Compound 1-8

<Preparation Example 9> Synthesis of the Following Compound 1-9

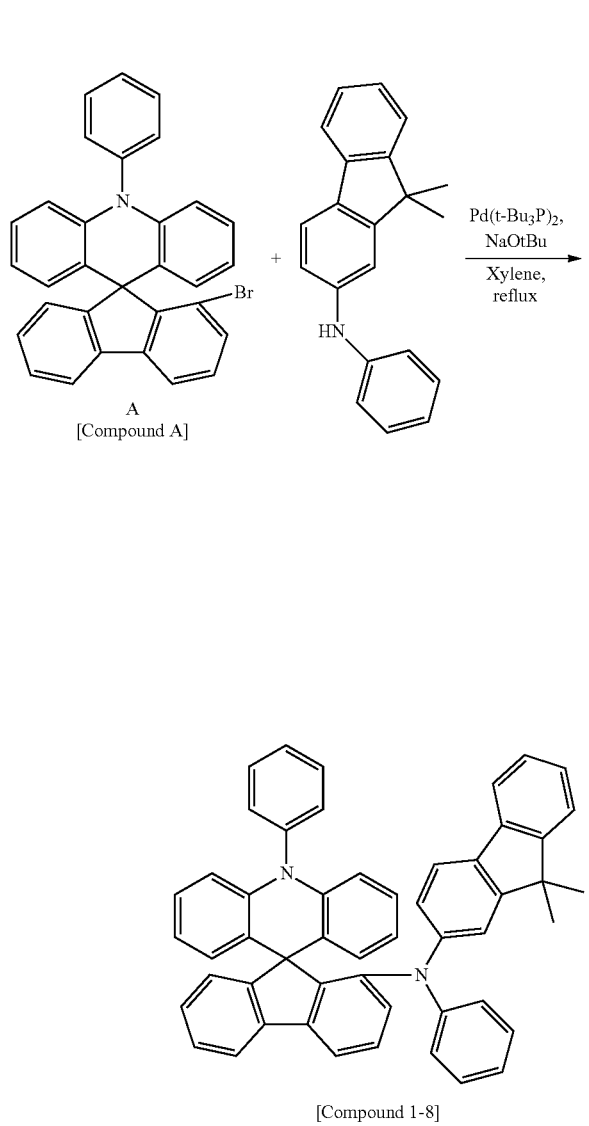

[Compound 1-8]

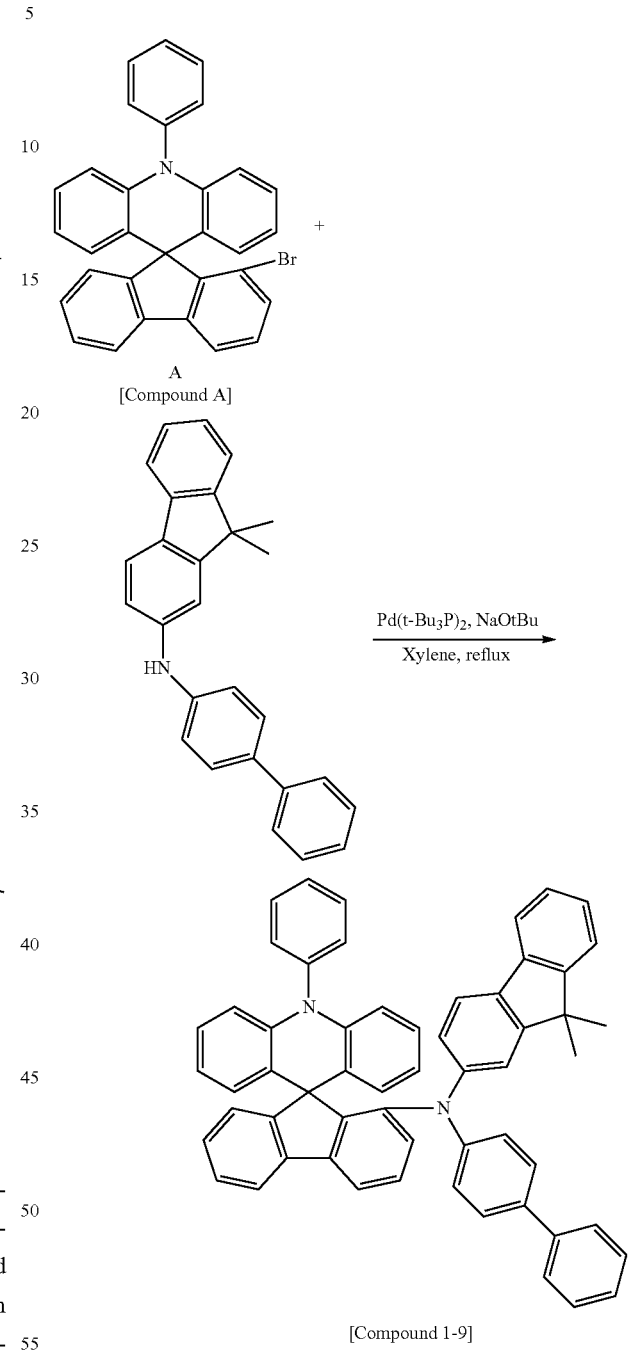

[Compound 1-9]

Compound A (10.0 g, 20.62 mmol) and 9,9-dimethyl-N-phenyl-9H-fluoren-2-amine (7.28 g, 22.68 mmol) were completely dissolved in 240 ml of xylene in a 500-ml round bottom flask under a nitrogen atmosphere, and then sodium tert-butoxide (2.58 g, 26.81 mol) was added thereto, bis(tri-tert-butylphosphine) palladium(0) (0.11 g, 0.21 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:19 to prepare Compound 1-8 (7.95 g, yield: 56%).

MS[M+H]$^+$=691

Compound A (10.0 g, 20.62 mmol) and N-([1,1'-biphenyl]-4-yl)-9,9-dimethyl-9H-fluoren-2-amine (8.21 g, 22.68 mmol) were completely dissolved in 240 ml of xylene in a 500-ml round bottom flask under a nitrogen atmosphere, and then sodium tert-butoxide (2.58 g, 26.81 mol) was added thereto, bis(tri-tert-butylphosphine) palladium(0) (0.11 g, 0.21 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:12 to prepare Compound 1-9 (12.88 g, yield: 81%).

MS[M+H]$^+$=767

<Preparation Example 10> Synthesis of the Following Compound 1-10

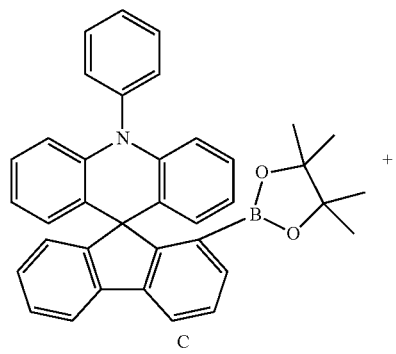

[Compound C]

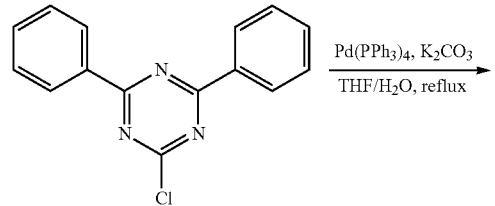

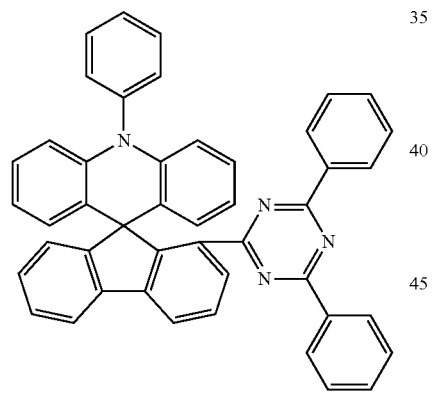

[Compound 1-10]

Compound C (10.0 g, 18.35 mmol) and 2-chloro-4,6-diphenyl-1,3,5-triazine (4.45 g, 16.68 mol) were completely dissolved in 200 ml of tetrahydrofuran in a 500-ml round bottom flask under a nitrogen atmosphere, and then a 2 M aqueous potassium carbonate solution (100 ml) was added thereto, tetrakis-(triphenylphosphine)palladium (0.58 g, 0.51 mmol) was put thereinto, and then the resulting mixture was heated and stirred for 4 hours. The temperature was lowered to normal temperature, the aqueous layer was removed, and the resulting product was dried over anhydrous magnesium sulfate, and then concentrated under reduced pressure, and recrystallized with 280 ml of ethyl acetate to prepare Compound 1-10 (9.92 g, yield: 85%).

MS[M+H]$^+$=639

<Preparation Example 11> Synthesis of the Following Compound 1-11

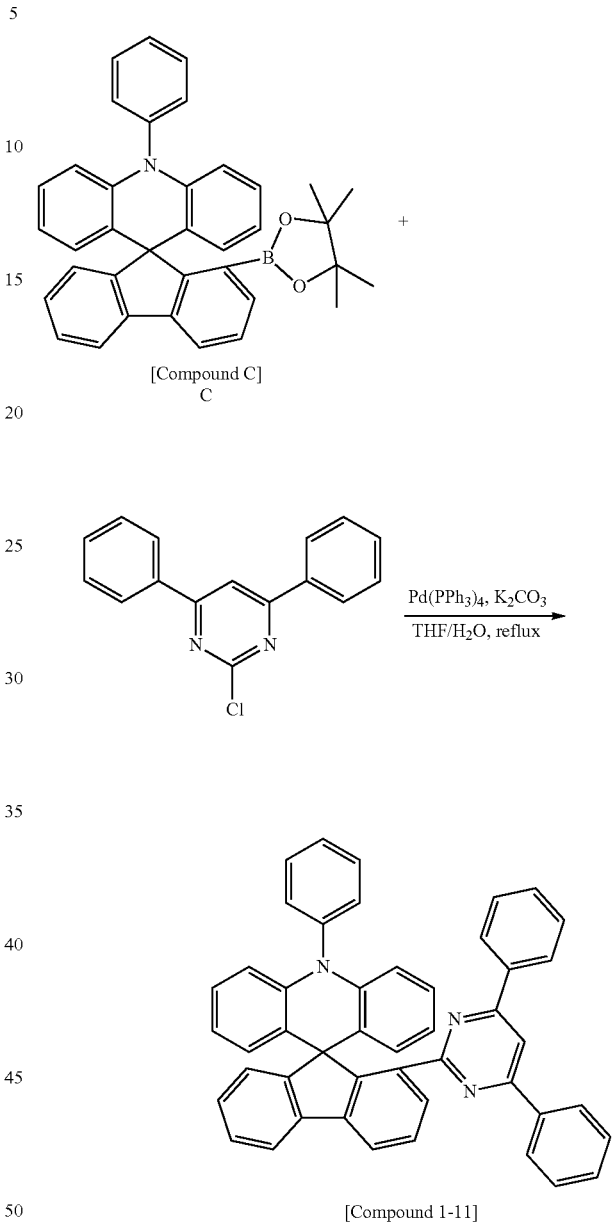

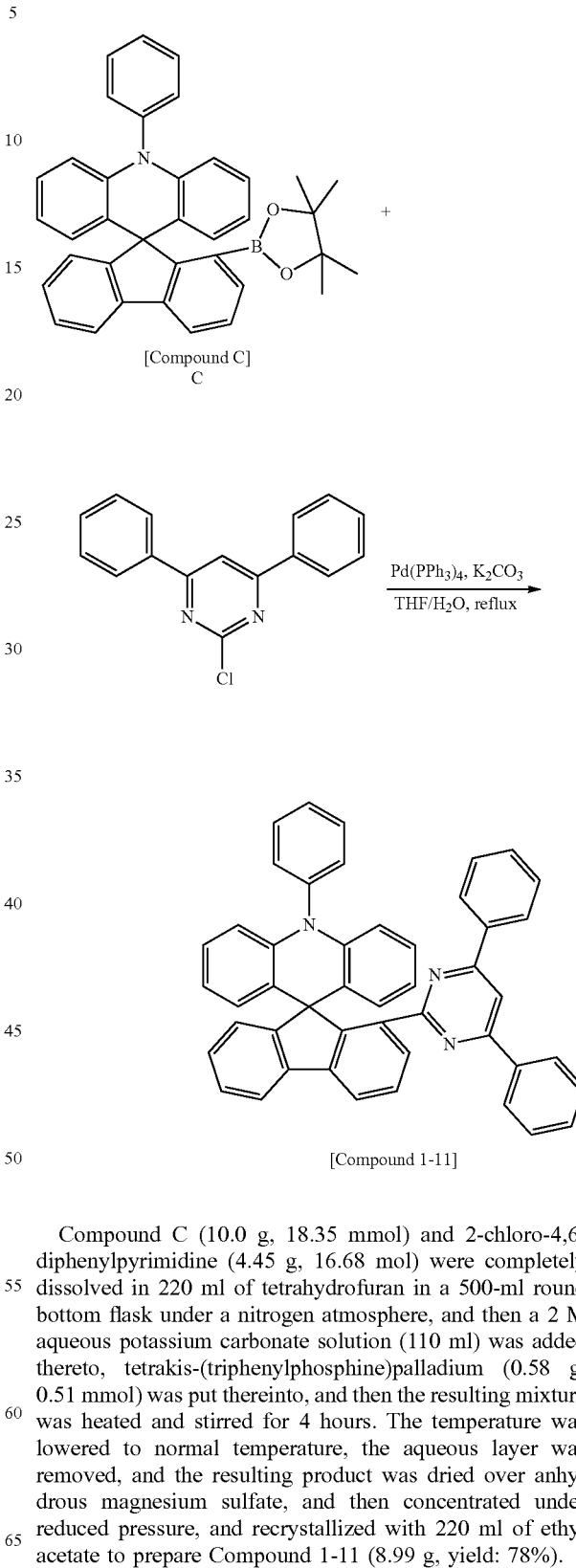

[Compound 1-11]

Compound C (10.0 g, 18.35 mmol) and 2-chloro-4,6-diphenylpyrimidine (4.45 g, 16.68 mol) were completely dissolved in 220 ml of tetrahydrofuran in a 500-ml round bottom flask under a nitrogen atmosphere, and then a 2 M aqueous potassium carbonate solution (110 ml) was added thereto, tetrakis-(triphenylphosphine)palladium (0.58 g, 0.51 mmol) was put thereinto, and then the resulting mixture was heated and stirred for 4 hours. The temperature was lowered to normal temperature, the aqueous layer was removed, and the resulting product was dried over anhydrous magnesium sulfate, and then concentrated under reduced pressure, and recrystallized with 220 ml of ethyl acetate to prepare Compound 1-11 (8.99 g, yield: 78%).

MS[M+H]$^+$=638

<Preparation Example 12> Synthesis of the Following Compound 1-12

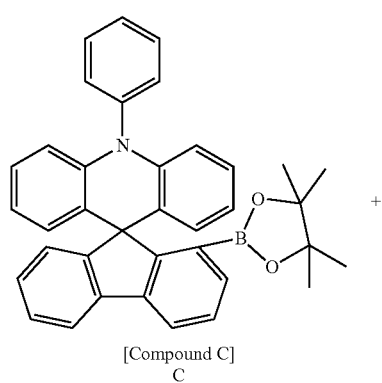

[Compound C]
C

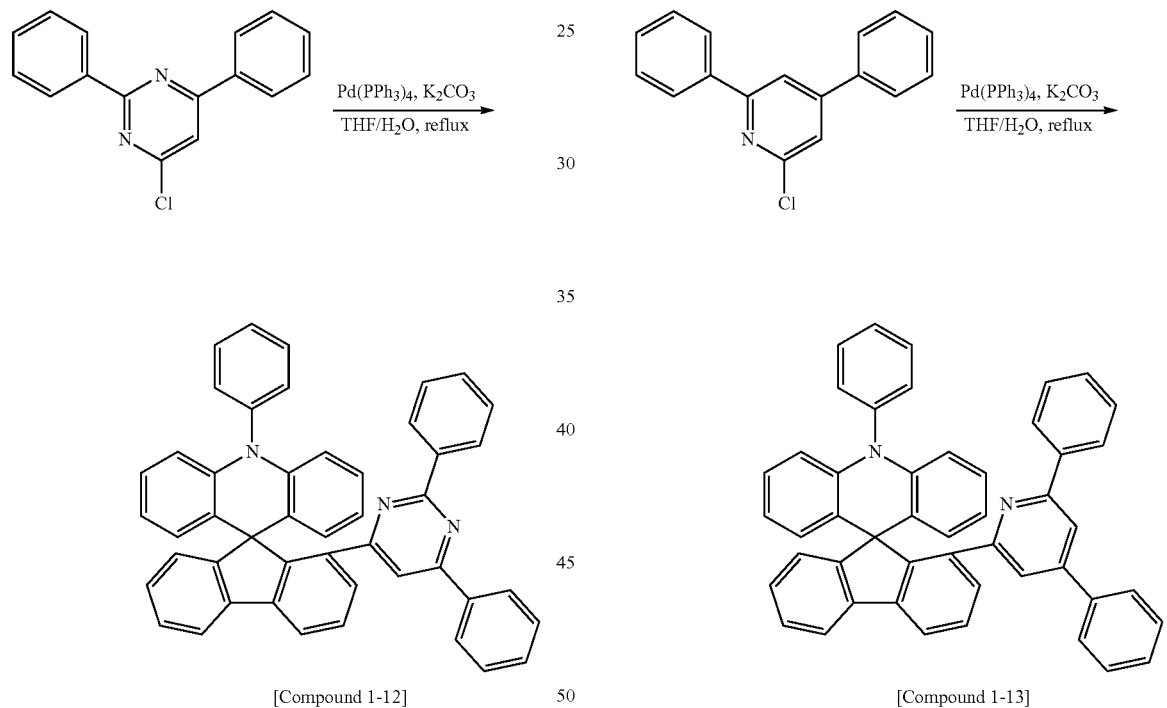

[Compound 1-12]

Compound C (10.0 g, 18.35 mmol) and 4-chloro-2,6-diphenylpyrimidine (4.45 g, 6.68 mol) were completely dissolved in 240 ml of tetrahydrofuran in a 500-ml round bottom flask under a nitrogen atmosphere, and then a 2 M aqueous potassium carbonate solution (120 ml) was added thereto, tetrakis-(triphenylphosphine)palladium (0.58 g, 0.51 mmol) was put thereinto, and then the resulting mixture was heated and stirred for 4 hours. The temperature was lowered to normal temperature, the aqueous layer was removed, and the resulting product was dried over anhydrous magnesium sulfate, and then concentrated under reduced pressure, and recrystallized with 240 ml of ethyl acetate to prepare Compound 1-12 (8.05 g, yield: 70%).

MS[M+H]$^+$=638

<Preparation Example 13> Synthesis of the Following Compound 1-13

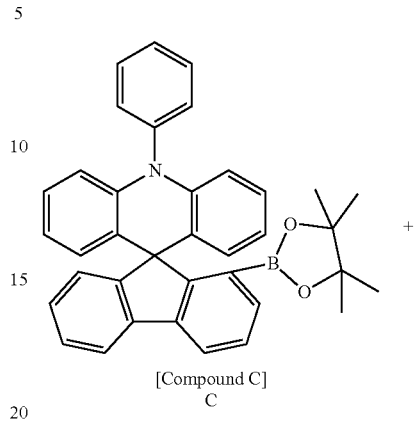

[Compound C]
C

[Compound 1-13]

Compound C (10.0 g, 18.35 mmol) and 2-chloro-4,6-diphenylpyridine (4.45 g, 16.68 mol) were completely dissolved in 300 ml of tetrahydrofuran in a 500-ml round bottom flask under a nitrogen atmosphere, and then a 2 M aqueous potassium carbonate solution (150 ml) was added thereto, tetrakis-(triphenylphosphine)palladium (0.58 g, 0.51 mmol) was put thereinto, and then the resulting mixture was heated and stirred for 4 hours. The temperature was lowered to normal temperature, the aqueous layer was removed, and the resulting product was dried over anhydrous magnesium sulfate, and then concentrated under reduced pressure, and recrystallized with 280 ml of ethyl acetate to prepare Compound 1-13 (7.23 g, yield: 63%).

MS[M+H]$^+$=637

<Preparation Example 14> Synthesis of the Following Compound 1-14

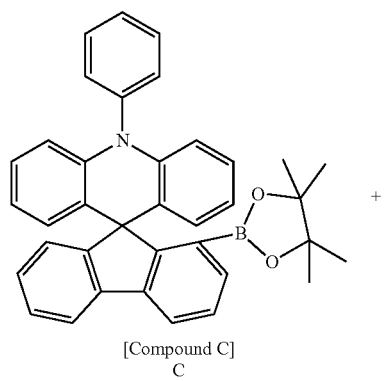

[Compound C]
C

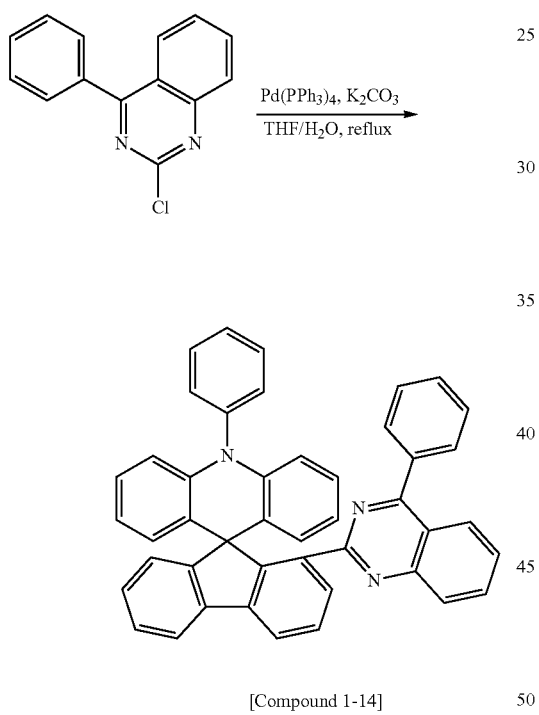

[Compound 1-14]

Compound C (10.0 g, 18.35 mmol) and 2-chloro-4-phenylquinazoline (4.45 g, 16.68 mol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.58 g, 0.51 mmol) was put thereinto, and then the resulting mixture was heated and stirred for 4 hours. The temperature was lowered to normal temperature, the aqueous layer was removed, and the resulting product was dried over anhydrous magnesium sulfate, and then concentrated under reduced pressure, and recrystallized with 300 ml of ethyl acetate to prepare Compound 1-14 (7.23 g, yield: 63%).

MS[M+H]$^+$=638

<Preparation Example 15> Synthesis of the Following Compounds 1-15 to 1-28

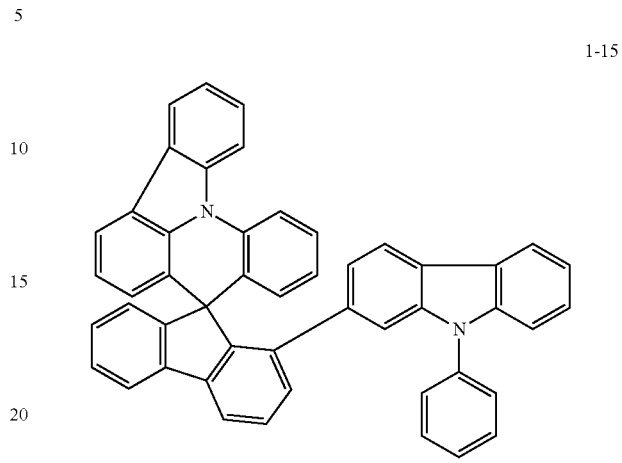

1-15

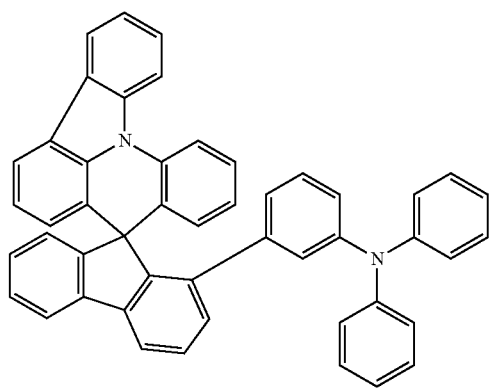

1-16

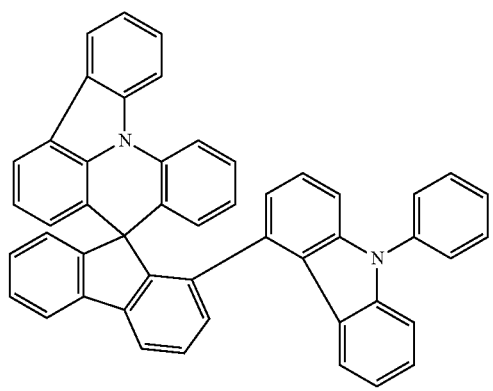

1-17

1-18
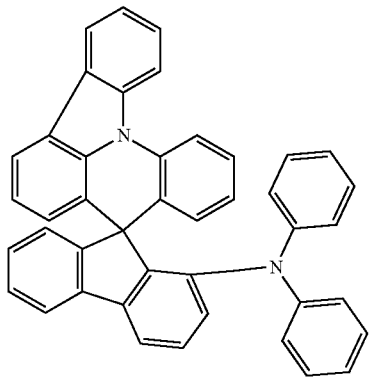
1-19
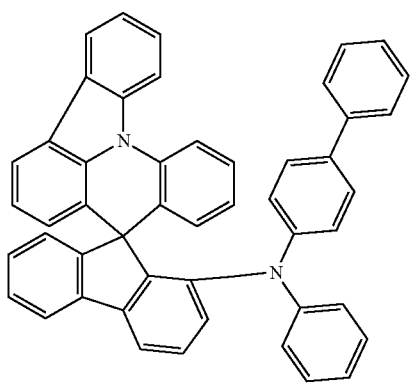
1-20
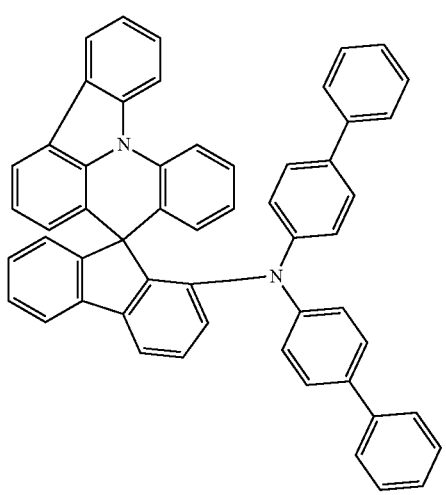
1-21
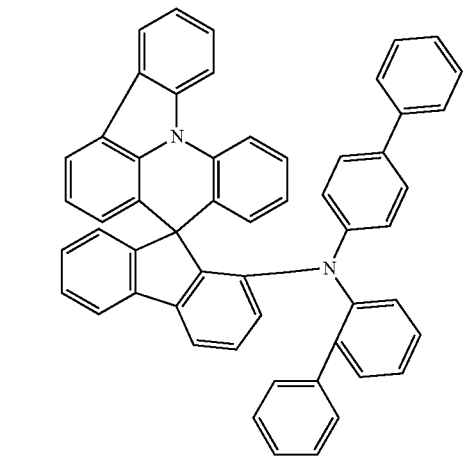
1-22
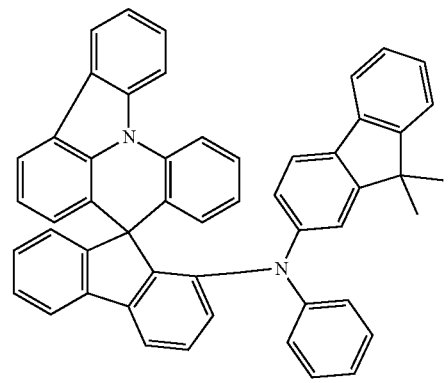
1-23
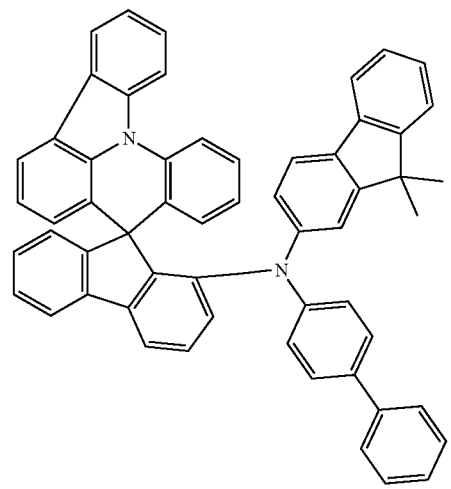

-continued 1-24
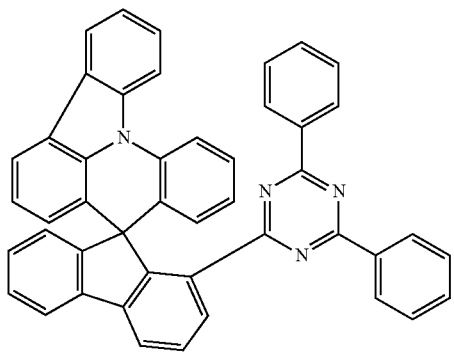

1-25
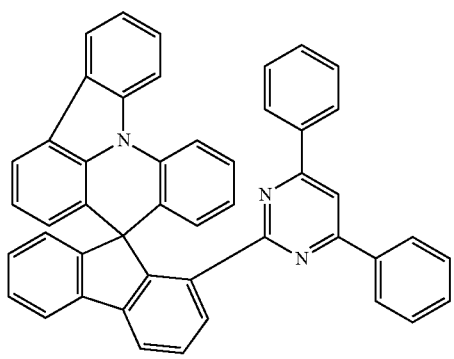

1-26
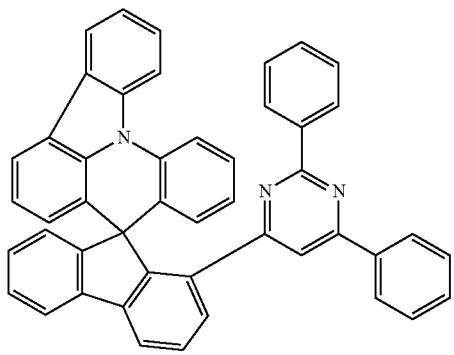

1-27
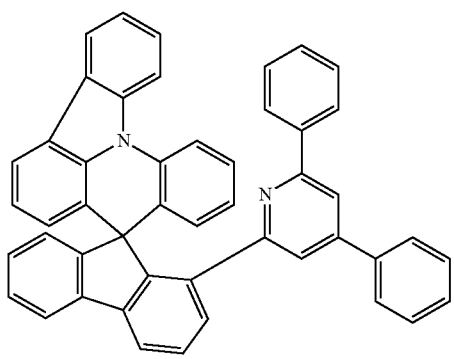

-continued 1-28
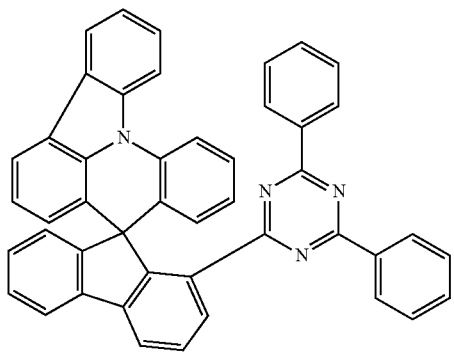

Compounds 1-15 to 1-28 were prepared in the same manner as in the methods of preparing Compounds 1-1 to 1-14, except that materials which are Compound B and Compound D were used instead of Compound A and Compound C, respectively as starting materials in Preparation Examples 1 to 14.

Experimental Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

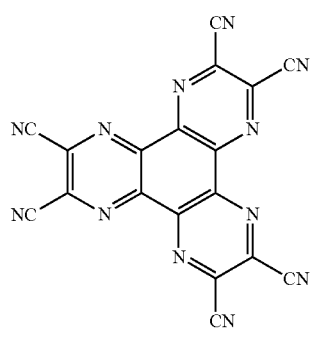

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transport layer.

[NPB]

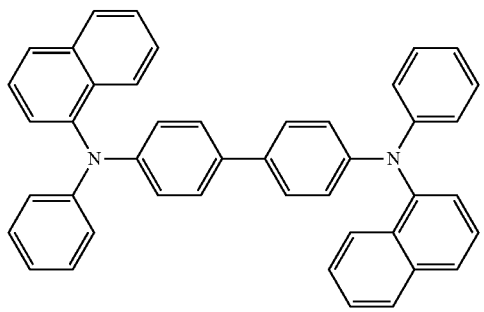

Subsequently, the following Compound 1-1 was vacuum deposited to have a film thickness of 100 Å on the hole transport layer, thereby forming an electron blocking layer.

[Compound 1-1]

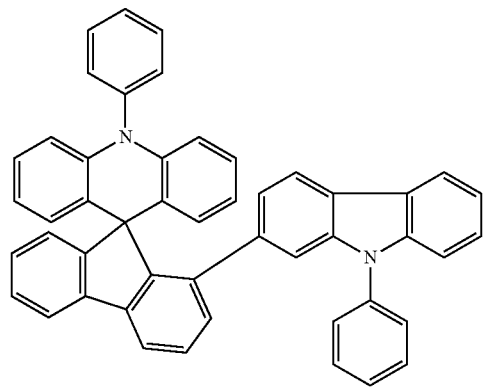

Subsequently, the following BH and BD were vacuum deposited at a weight ratio of 25:1 to have a film thickness of 300 Å on the electron blocking layer, thereby forming a light emitting layer.

[BH]

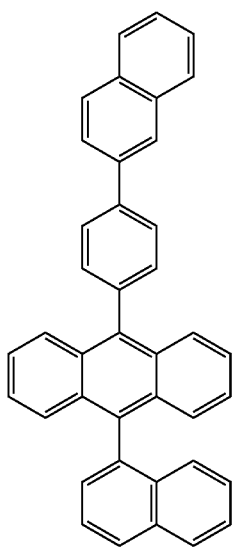

[BD]

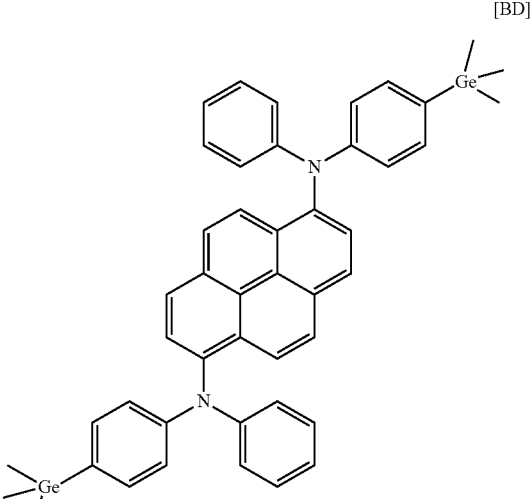

[ET1]

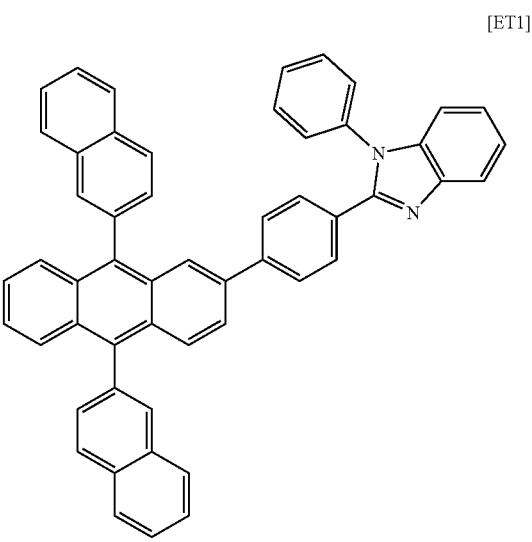

[Liq]

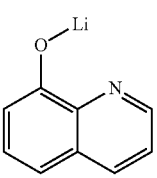

Compound ET1 and Compound Liq (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Experimental Example 1-2

An organic light emitting device was manufactured in the same manner as in Experimental Example 1-1, except that Compound 1-2 was used instead of Compound 1-1 in Experimental Example 1-1.

Experimental Example 1-3

An organic light emitting device was manufactured in the same manner as in Experimental Example 1-1, except that Compound 1-3 was used instead of Compound 1-1 in Experimental Example 1-1.

Experimental Example 1-4

An organic light emitting device was manufactured in the same manner as in Experimental Example 1-1, except that Compound 1-4 was used instead of Compound 1-1 in Experimental Example 1-1.

Experimental Example 1-5

An organic light emitting device was manufactured in the same manner as in Experimental Example 1-1, except that Compound 1-5 was used instead of Compound 1-1 in Experimental Example 1-1.

Experimental Example 1-6

An organic light emitting device was manufactured in the same manner as in Experimental Example 1-1, except that Compound 1-6 was used instead of Compound 1-1 in Experimental Example 1-1.

Experimental Example 1-7

An organic light emitting device was manufactured in the same manner as in Experimental Example 1-1, except that Compound 1-7 was used instead of Compound 1-1 in Experimental Example 1-1.

Experimental Example 1-8

An organic light emitting device was manufactured in the same manner as in Experimental Example 1-1, except that Compound 1-8 was used instead of Compound 1-1 in Experimental Example 1-1.

Experimental Example 1-9

An organic light emitting device was manufactured in the same manner as in Experimental Example 1-1, except that Compound 1-9 was used instead of Compound 1-1 in Experimental Example 1-1.

Experimental Example 1-10

An organic light emitting device was manufactured in the same manner as in Experimental Example 1-1, except that Compound 1-15 was used instead of Compound 1-1 in Experimental Example 1-1.

Experimental Example 1-11

An organic light emitting device was manufactured in the same manner as in Experimental Example 1-1, except that Compound 1-16 was used instead of Compound 1-1 in Experimental Example 1-1.

Experimental Example 1-12

An organic light emitting device was manufactured in the same manner as in Experimental Example 1-1, except that Compound 1-17 was used instead of Compound 1-1 in Experimental Example 1-1.

Experimental Example 1-13

An organic light emitting device was manufactured in the same manner as in Experimental Example 1-1, except that Compound 1-18 was used instead of Compound 1-1 in Experimental Example 1-1.

Experimental Example 1-14

An organic light emitting device was manufactured in the same manner as in Experimental Example 1-1, except that Compound 1-19 was used instead of Compound 1-1 in Experimental Example 1-1.

Experimental Example 1-15

An organic light emitting device was manufactured in the same manner as in Experimental Example 1-1, except that Compound 1-20 was used instead of Compound 1-2 in Experimental Example 1-1.

Experimental Example 1-16

An organic light emitting device was manufactured in the same manner as in Experimental Example 1-1, except that Compound 1-21 was used instead of Compound 1-2 in Experimental Example 1-1.

Experimental Example 1-17

An organic light emitting device was manufactured in the same manner as in Experimental Example 1-1, except that Compound 1-22 was used instead of Compound 1-1 in Experimental Example 1-1.

Experimental Example 1-18

An organic light emitting device was manufactured in the same manner as in Experimental Example 1-1, except that Compound 1-23 was used instead of Compound 1-1 in Experimental Example 1-1.

Comparative Example 1-1

An organic light emitting device was manufactured in the same manner as in Experimental Example 1-1, except that EB 1 (TCTA) was used instead of Compound 1 in Experimental Example 1-1.

[EB 1]

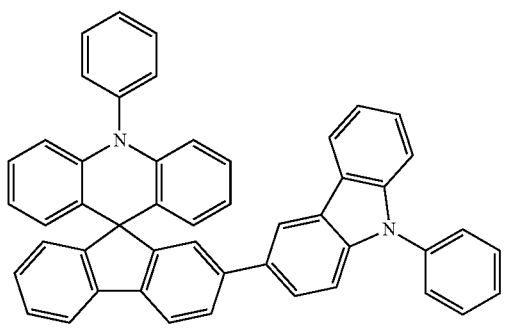

Comparative Example 1-2

An organic light emitting device was manufactured in the same manner as in Experimental Example 1-1, except that EB 2 was used instead of Compound 1 in Experimental Example 1-1.

[EB 2]

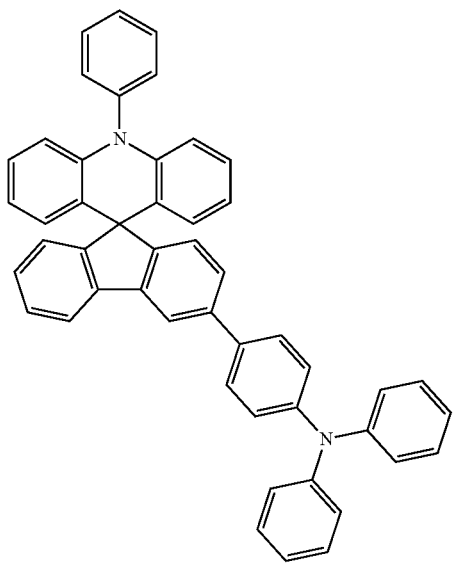

When current was applied to the organic light emitting devices manufactured in Experimental Examples 1-1 to 1-18 and Comparative Examples 1-1 and 1-2, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1-1 | 3.85 | 5.20 | (0.139, 0.125) |
| Experimental Example 1-2 | Compound 1-2 | 3.72 | 5.35 | (0.138, 0.126) |
| Experimental Example 1-3 | Compound 1-3 | 3.57 | 5.79 | (0.138, 0.127) |
| Experimental Example 1-4 | Compound 1-4 | 3.58 | 5.67 | (0.137, 0.125) |
| Experimental Example 1-5 | Compound 1-5 | 3.59 | 5.78 | (0.136, 0.125) |
| Experimental Example 1-6 | Compound 1-6 | 3.54 | 5.61 | (0.136, 0.127) |
| Experimental Example 1-7 | Compound 1-7 | 3.53 | 5.73 | (0.136, 0.125) |
| Experimental Example 1-8 | Compound 1-8 | 3.54 | 5.65 | (0.137, 0.125) |
| Experimental Example 1-9 | Compound 1-9 | 3.63 | 5.54 | (0.138, 0.125) |
| Experimental Example 1-10 | Compound 1-15 | 3.68 | 5.43 | (0.136, 0.125) |
| Experimental Example 1-11 | Compound 1-16 | 3.63 | 5.51 | (0.137, 0.125) |
| Experimental Example 1-12 | Compound 1-17 | 3.65 | 5.41 | (0.136, 0.125) |
| Experimental Example 1-13 | Compound 1-18 | 3.72 | 5.55 | (0.138, 0.126) |
| Experimental Example 1-14 | Compound 1-19 | 3.77 | 5.54 | (0.137, 0.125) |
| Experimental Example 1-15 | Compound 1-20 | 3.70 | 5.46 | (0.136, 0.127) |
| Experimental Example 1-16 | Compound 1-21 | 3.71 | 5.58 | (0.135, 0.127) |
| Experimental Example 1-17 | Compound 1-22 | 3.54 | 5.67 | (0.138, 0.127) |
| Experimental Example 1-18 | Compound 1-23 | 3.63 | 5.55 | (0.137, 0.125) |
| Comparative Example 1-1 | EB 1 | 4.26 | 4.62 | (0.138, 0.127) |
| Comparative Example 1-2 | EB 2 | 4.45 | 4.58 | (0.139, 0.125) |

As observed in Table 1, it can be seen that the compounds in Experimental Examples 1-1 to 1-18 exhibit lower voltage and higher efficiency characteristics than those in Comparative Examples 1-1 and 1-2, in which a substituent is linked to Nos. 2 and 3 positions of the core as an electron blocking layer in the organic light emitting device.

It could be confirmed that the compound derivatives of Chemical Formulae according to the present invention have excellent electron blocking capability, and thus exhibit low voltage and high efficiency characteristics, and may be applied to an organic light emitting device.

Experimental Example 2-1

The compounds prepared in the Synthesis Examples were subjected to high-purity sublimation purification by a typically known method, and then green organic light emitting devices were manufactured by the following method.

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

An organic light emitting device was manufactured by configuring the light emitting device in the order of m-MTDATA (60 nm)/TCTA (80 nm)/Compound 1-10+10%

Ir(ppy)₃ (300 nm)/BCP (10 nm)/Alq₃ (30 nm)/LiF (1 nm)/Al (200 nm) on the thus prepared ITO transparent electrode by using Compound 1-10 as a host.

The structures of m-MTDATA, TCTA, Ir(ppy)₃, and BCP are as follows.

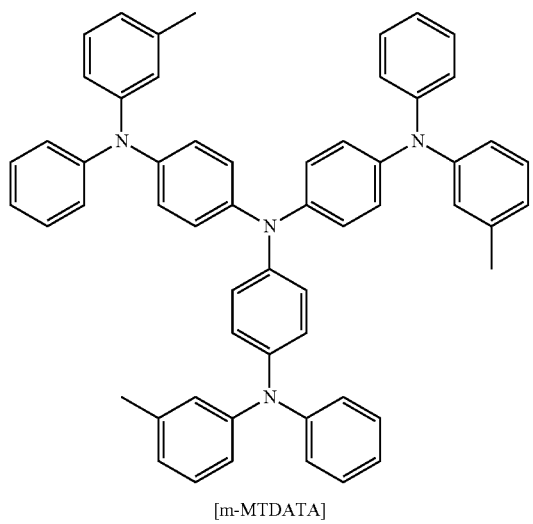

[m-MTDATA]

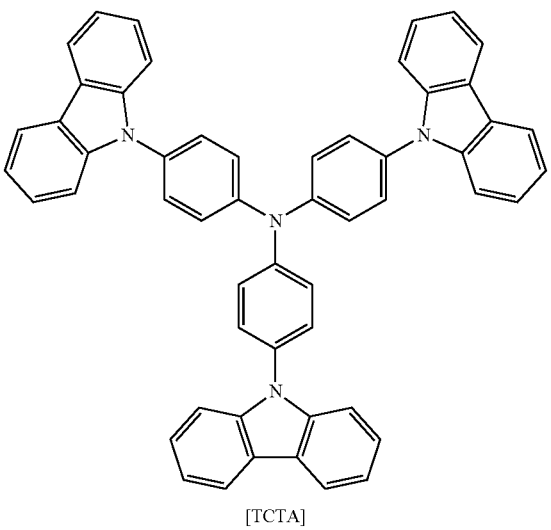

[TCTA]

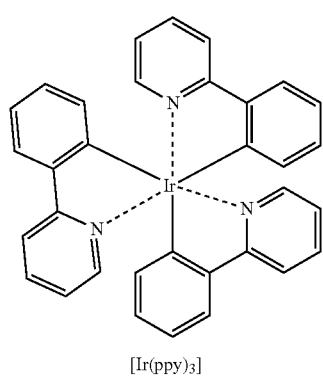

[Ir(ppy)₃]

-continued

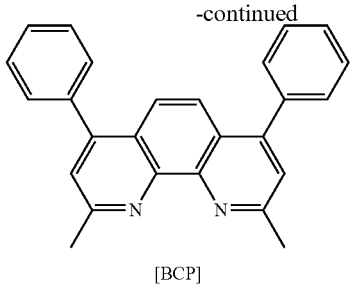

[BCP]

Experimental Example 2-2

An organic light emitting device was manufactured in the same manner as in Experimental Example 2-1, except that Compound 1-11 was used instead of Compound 1-10 in Experimental Example 2-1.

Experimental Example 2-3

An organic light emitting device was manufactured in the same manner as in Experimental Example 2-1, except that Compound 1-12 was used instead of Compound 1-10 in Experimental Example 2-1.

Experimental Example 2-4

An organic light emitting device was manufactured in the same manner as in Experimental Example 2-1, except that Compound 1-13 was used instead of Compound 1-10 in Experimental Example 2-1.

Experimental Example 2-5

An organic light emitting device was manufactured in the same manner as in Experimental Example 2-1, except that Compound 1-14 was used instead of Compound 1-10 in Experimental Example 2-1.

Experimental Example 2-6

An organic light emitting device was manufactured in the same manner as in Experimental Example 2-1, except that Compound 1-24 was used instead of Compound 1-10 in Experimental Example 2-1.

Experimental Example 2-7

An organic light emitting device was manufactured in the same manner as in Experimental Example 2-1, except that Compound 1-25 was used instead of Compound 1-10 in Experimental Example 2-1.

Experimental Example 2-8

An organic light emitting device was manufactured in the same manner as in Experimental Example 2-1, except that Compound 1-26 was used instead of Compound 1-10 in Experimental Example 2-1.

Experimental Example 2-9

An organic light emitting device was manufactured in the same manner as in Experimental Example 2-1, except that Compound 1-27 was used instead of Compound 1-10 in Experimental Example 2-1.

Experimental Example 2-10

An organic light emitting device was manufactured in the same manner as in Experimental Example 2-1, except that Compound 1-28 was used instead of Compound 1-10 in Experimental Example 2-1.

Comparative Example 2-1

An organic light emitting device was manufactured in the same manner as in Experimental Example 2-1, except that GH 1 (CBP) was used instead of Compound 1-10 in Experimental Example 2-1.

[GH 1]

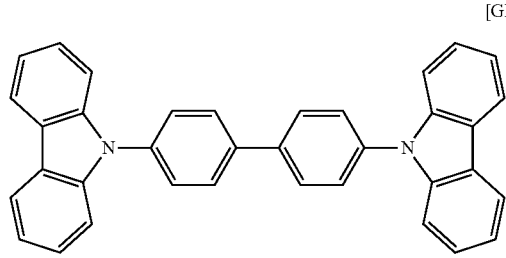

Comparative Example 2-2

An organic light emitting device was manufactured in the same manner as in Experimental Example 2-1, except that GH 2 was used instead of Compound 1-10 in Experimental Example 2-1.

[GH 2]

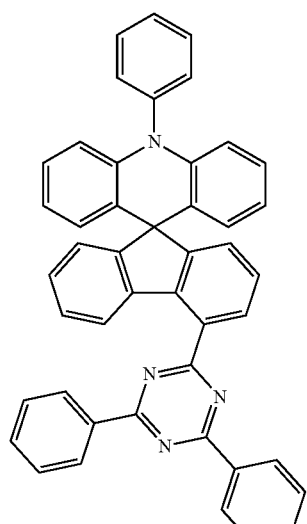

Comparative Example 2-3

An organic light emitting device was manufactured in the same manner as in Experimental Example 2-1, except that GH 3 was used instead of Compound 1-10 in Experimental Example 2-1.

[GH 3]

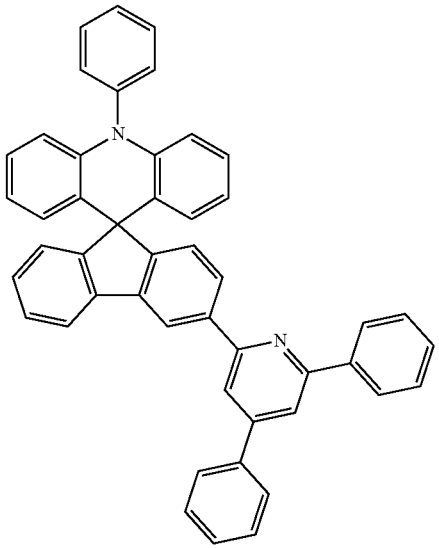

When current was applied to the organic light emitting devices manufactured in Experimental Examples 2-1 to 2-10 and Comparative Examples 1 to 3, the results of Table 2 were obtained.

TABLE 2

|  | Compound (Host) | Voltage (V@10 mA/cm$^2$) | Efficiency (cd/A@10 mA/cm$^2$) | EL peak (nm) |
| --- | --- | --- | --- | --- |
| Experimental Example 2-1 | Compound 1-10 | 5.18 | 43.93 | 517 |
| Experimental Example 2-2 | Compound 1-11 | 5.26 | 45.24 | 516 |
| Experimental Example 2-3 | Compound 1-12 | 5.15 | 44.79 | 518 |
| Experimental Example 2-4 | Compound 1-13 | 5.29 | 46.15 | 517 |
| Experimental Example 2-5 | Compound 1-14 | 5.28 | 44.31 | 515 |
| Experimental Example 2-6 | Compound 1-24 | 5.13 | 45.63 | 516 |
| Experimental Example 2-7 | Compound 1-25 | 5.29 | 45.62 | 516 |
| Experimental Example 2-8 | Compound 1-26 | 5.27 | 46.64 | 517 |
| Experimental Example 2-9 | Compound 1-27 | 5.24 | 46.68 | 518 |
| Experimental Example 2-10 | Compound 1-28 | 5.18 | 43.83 | 517 |
| Comparative Example 2-1 | GH 1 (CBP) | 7.01 | 36.72 | 517 |
| Comparative Example 2-2 | GH 2 | 6.51 | 38.72 | 517 |
| Comparative Example 2-3 | GH 3 | 6.61 | 38.72 | 517 |

As a result of the experiments, it could be confirmed that the green organic light emitting devices of Experimental Examples 2-1 to 2-10 in which the compound represented by Chemical Formula 1 according to the present invention was used as a host material of the green light emitting layer exhibited better performances in terms of current efficiency and driving voltage than the green organic light emitting devices of Comparative Example 2-1 in which CBP in the related art was used and Comparative Examples 2-2 and 2-3 in which a substituent is linked to Nos. 2 and 4 positions of the core.

Although the preferred exemplary embodiments (an electron blocking layer, a hole transport layer) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS

1: Substrate
2: Positive electrode
3: Light emitting layer
4: Negative electrode
5: Hole injection layer
6: Hole transport layer
7: Electron transport layer

The invention claimed is:

1. A compound represented by the following Chemical Formula 2:

[Chemical Formula 2]

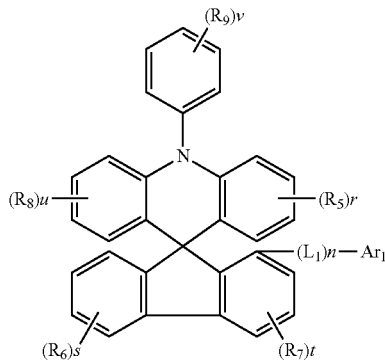

in Chemical Formula 2, $L_1$ is a direct bond; a substituted or unsubstituted arylene group; or a substituted or unsubstituted heteroarylene; n is an integer of 0 to 2, and when n is 2, each $L_1$ is the same as or different from each other;

$Ar_1$ is a substituted or unsubstituted aryl group; a substituted or unsubstituted heterocyclic group; a substituted or unsubstituted arylamino group; a substituted or unsubstituted arylphosphine group; or a substituted or unsubstituted silyl group; and $R_5$ to $R_7$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group; and each of $Ar_1$, $R_5$ and $R_6$ optionally combines with an adjacent group via a single bond to form a ring, $R_7$ does not combine with an adjacent group via a single bond to form a ring s, and r are each independently an integer of 0 to 4, t is an integer of 0 to 3, and when r, s, and t are each 2 or more, each of $R_5$, $R_6$ and $R_7$, respectively, is the same as or different from each other, $R_8$ and $R_9$ are hydrogen, and u=4, and v=5.

2. The compound of claim 1, wherein $R_5$ to $R_7$ are the same as or different from each other, and are each independently hydrogen; or deuterium.

3. The compound of claim 1, wherein $Ar_1$ is an aryl group which is unsubstituted or substituted with one or two or more groups of a halogen group, a nitrile group, an alkyl group, a silyl group, an arylamino group, an arylphosphine group, an aryl group, and a heteroaryl group; a heterocyclic group which is unsubstituted or substituted with one or two or more groups of a halogen group, a nitrile group, an alkyl group, a silyl group, an arylamino group, an arylphosphine group, an aryl group, and a heteroaryl group; an arylamino group which is unsubstituted or substituted with one or two or more groups of a halogen group, a nitrile group, an alkyl group, a silyl group, an arylamino group, an arylphosphine group, an aryl group, and a heteroaryl group; an arylphosphine group which is unsubstituted or substituted with one or two or more groups of a halogen group, a nitrile group, an alkyl group, a silyl group, an arylamino group, an arylphosphine group, an aryl group, and a heteroaryl group; a trialkylsilyl group; or a triarylsilyl group.

4. The compound of claim 1, wherein $L_1$ is a direct bond or a substituted or unsubstituted arylene.

5. The compound of claim 1, wherein $L_1$ is a direct bond, phenylene, biphenylylene, terphenylylene, quarterphenylylene, naphthylene, anthrylene, fluorene, phenanthrene, pyrene, or triphenylene.

6. The compound of claim 1, wherein the compound of Chemical Formula 2 is any one selected from the following structural formulae:

7-1

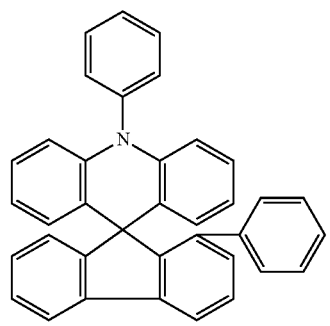

7-2
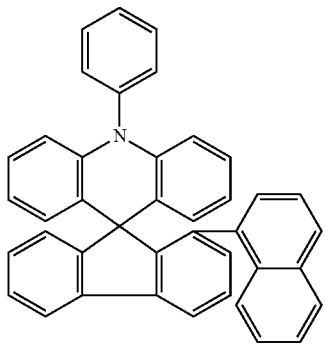
7-3
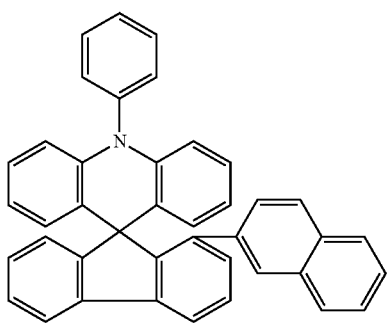
7-4
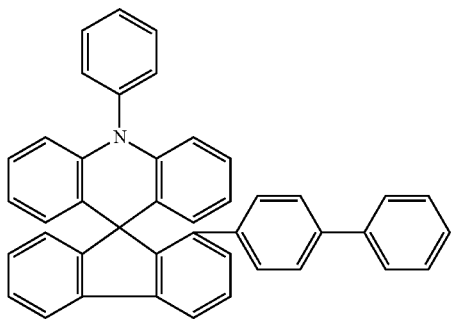
7-5
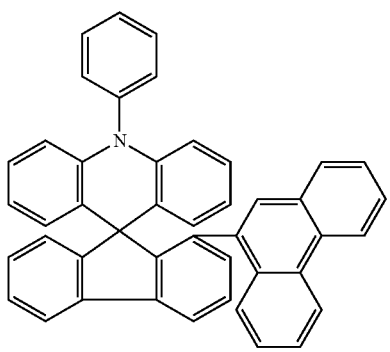
7-6
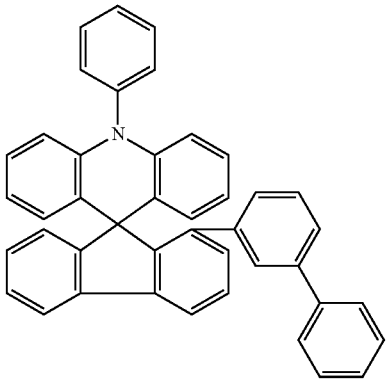
7-7
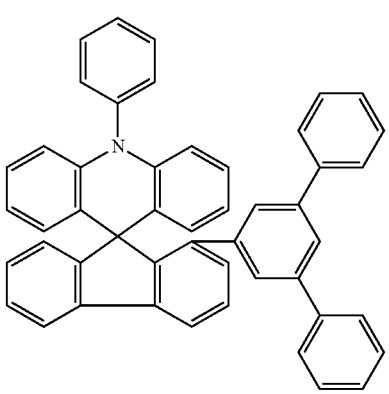
7-8
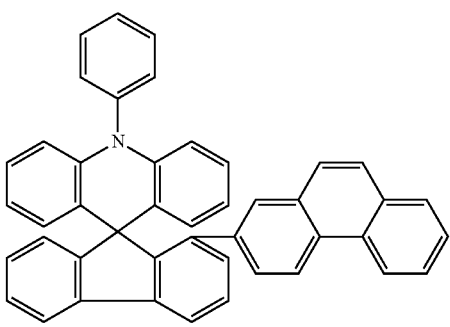
7-9
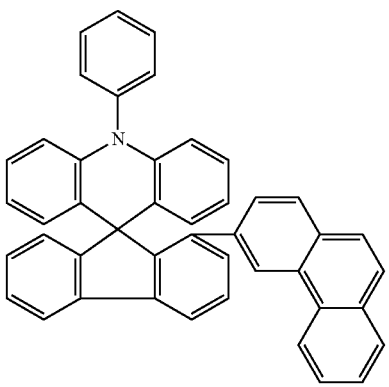

-continued
7-10
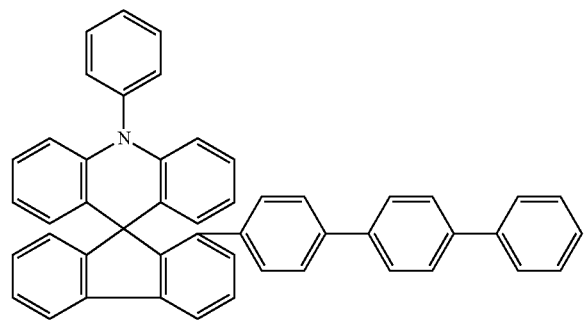
7-11
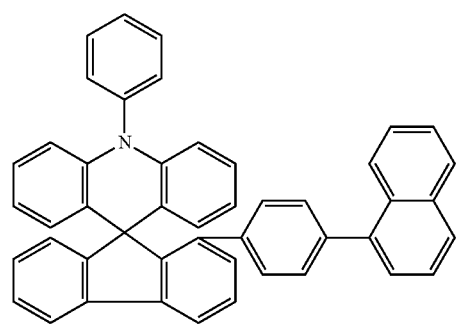
7-12
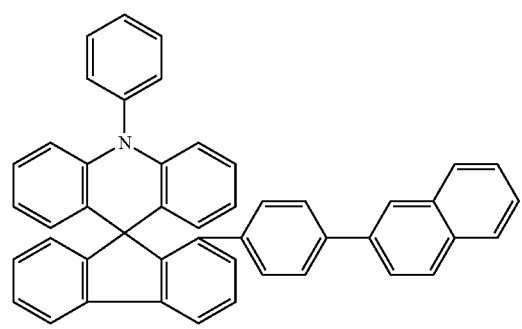
7-13
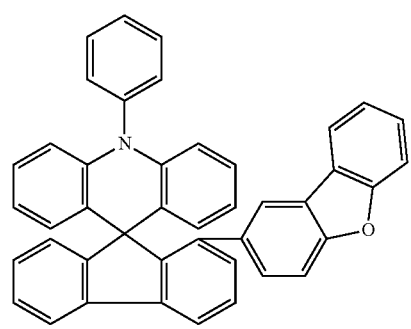
7-14
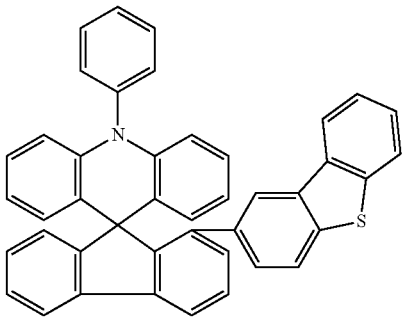
7-15
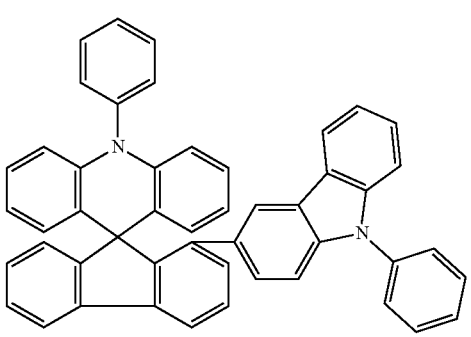
7-16
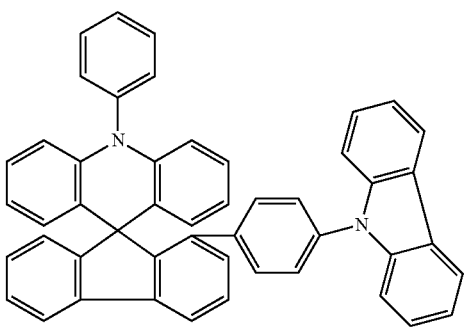
7-17
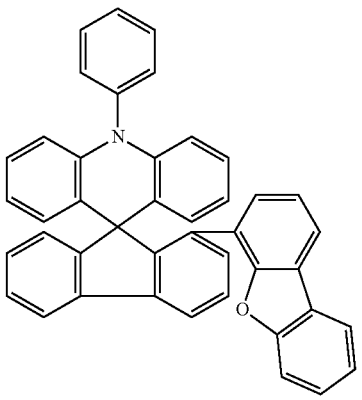

7-18
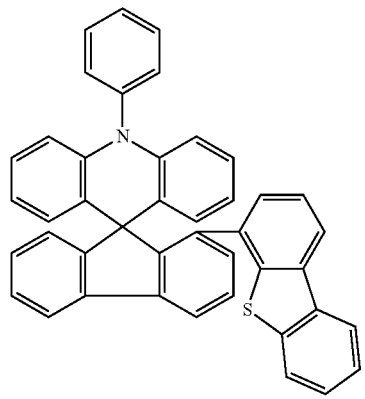
7-19
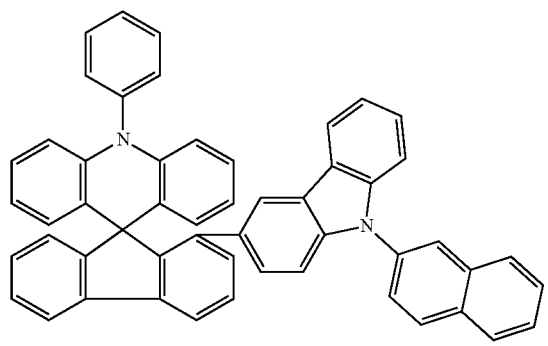
7-20
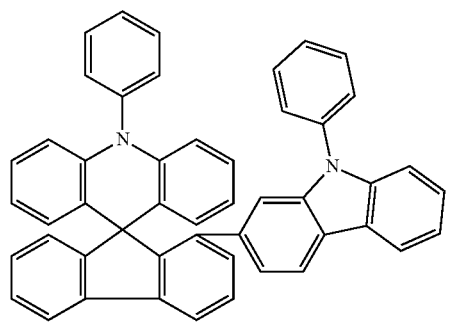
7-21
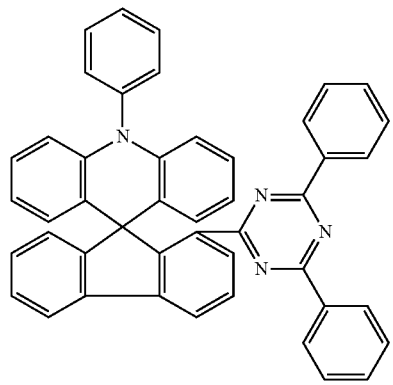
7-22
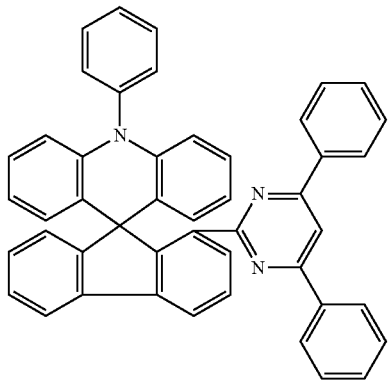
7-23
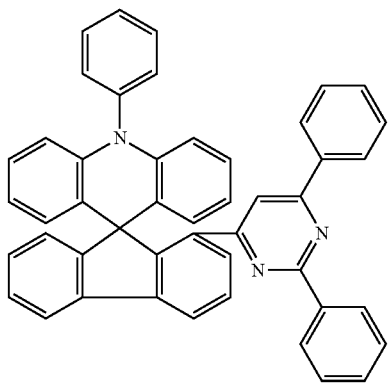
7-24
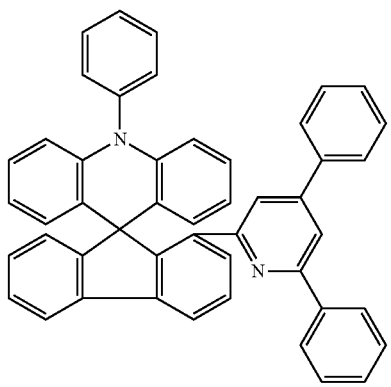
7-25
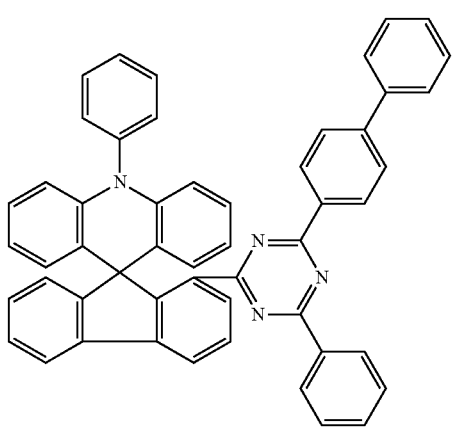

-continued
7-26
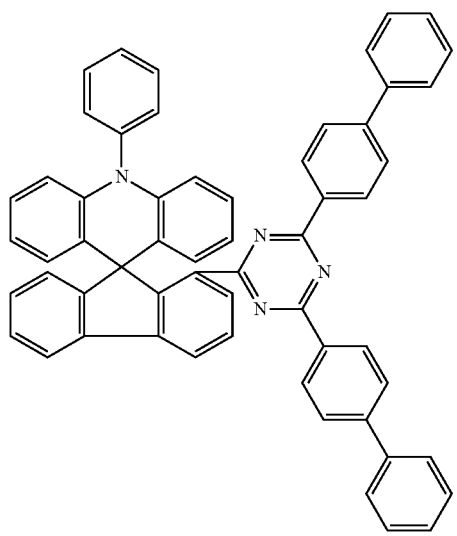
7-27
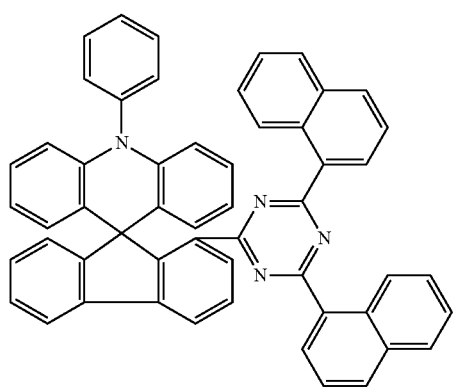
7-28
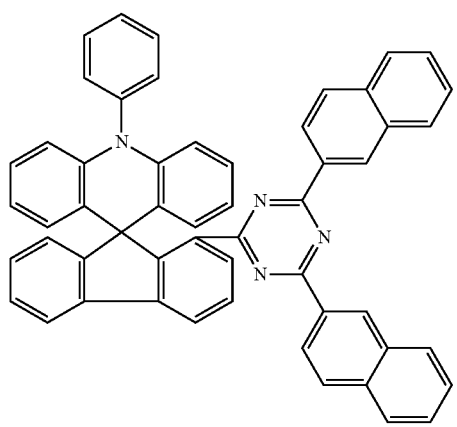
-continued
7-29
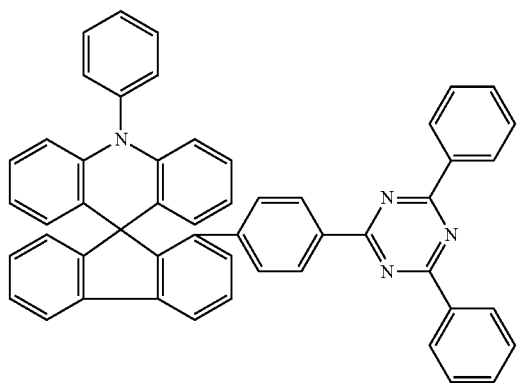
7-30
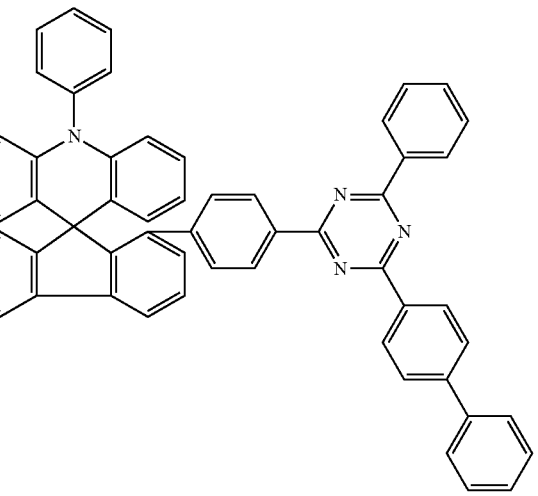
7-31
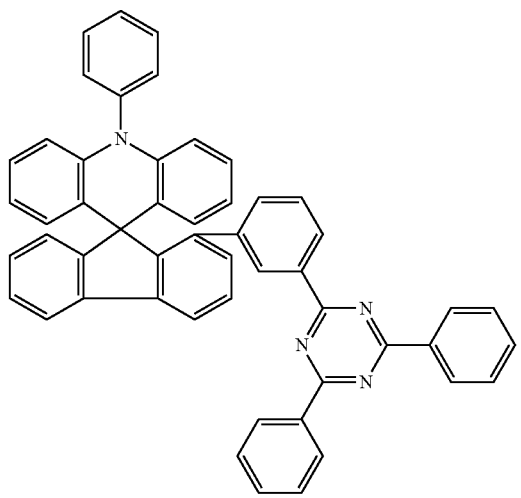

7-32
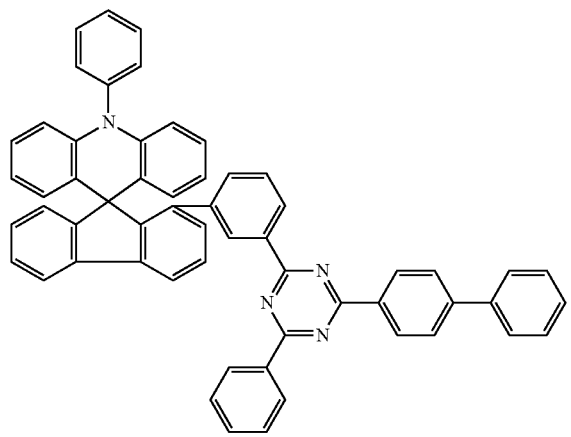
7-33
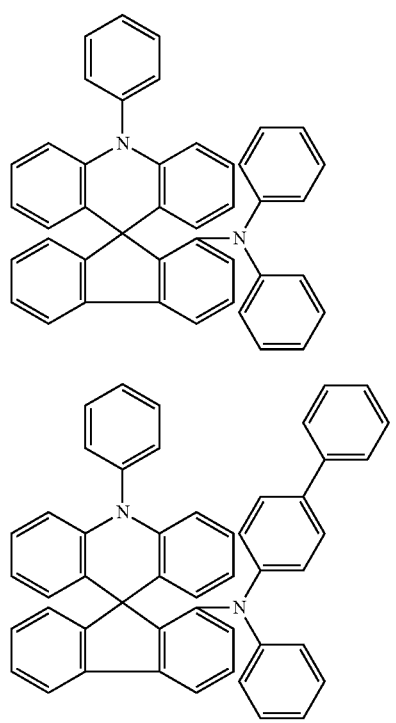
7-34
7-35
7-36
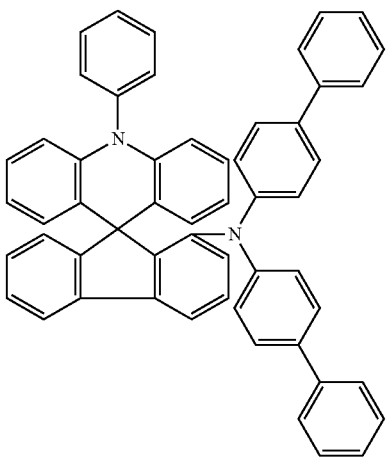
7-37
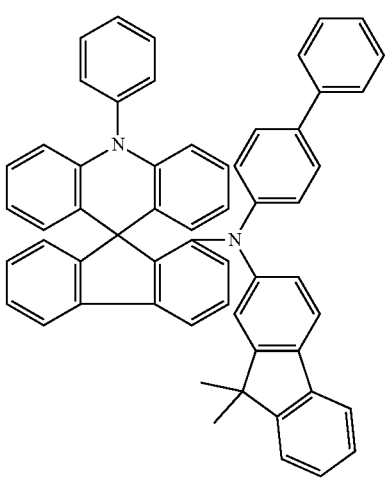
7-38
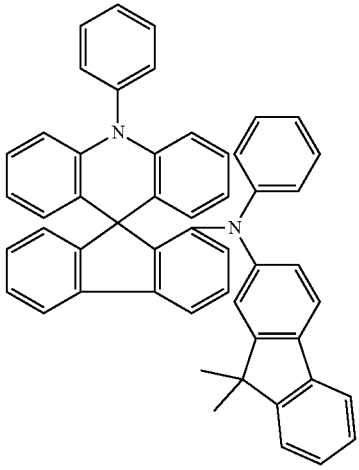
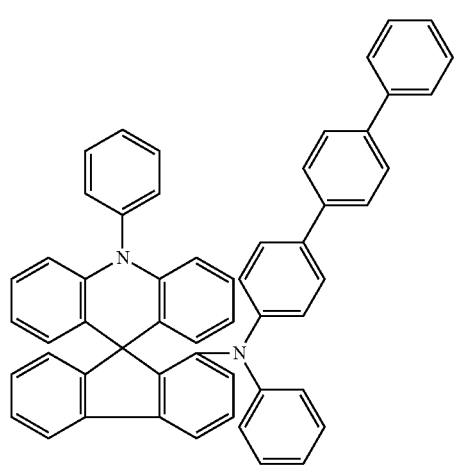

7-39
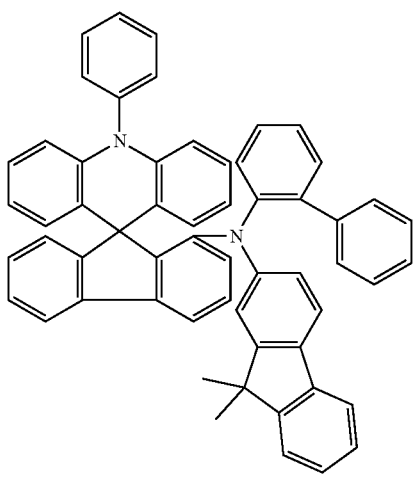
7-40
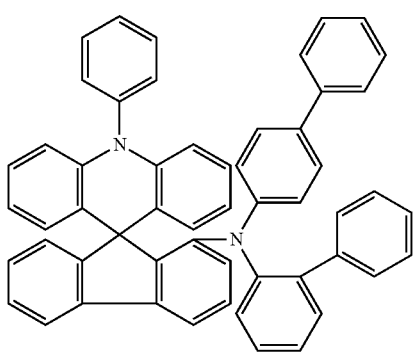
7-41
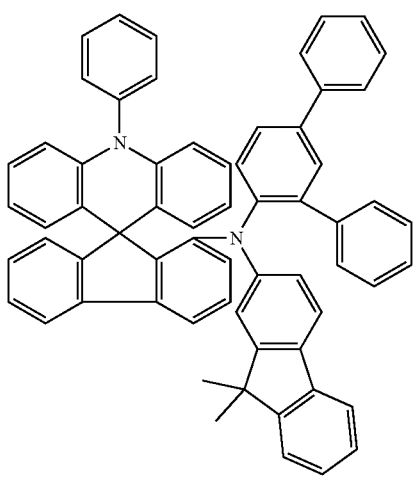
7-42
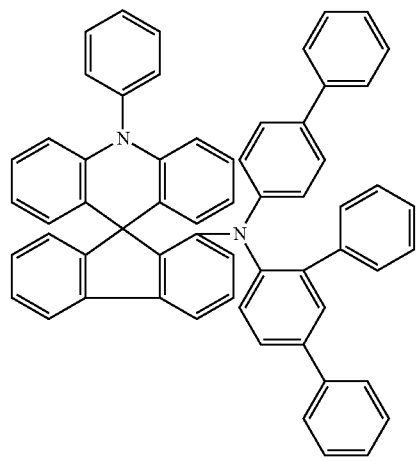
7-43
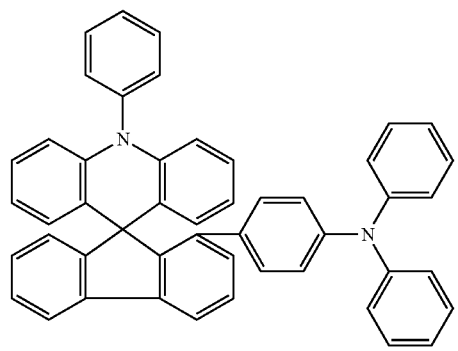
7-44
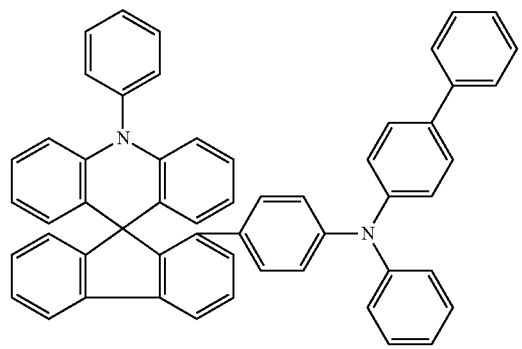

-continued
7-45
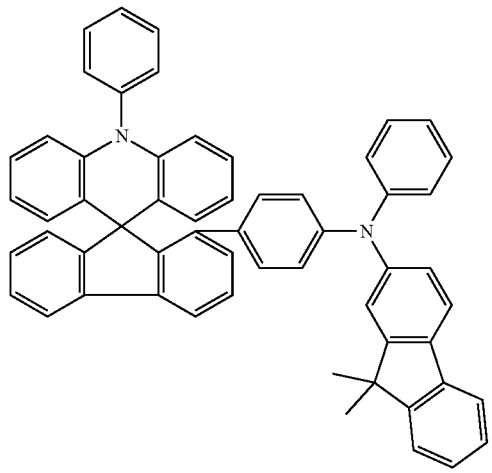
7-46
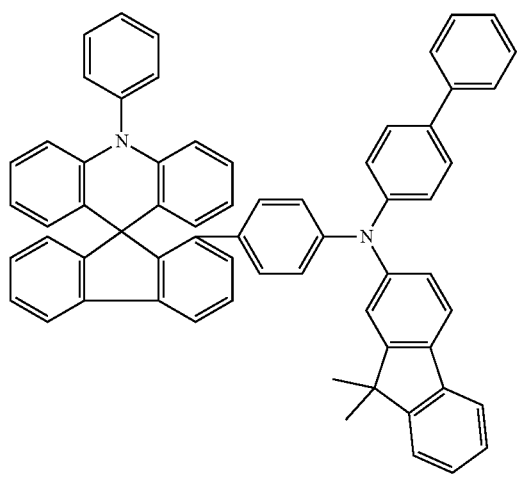
7-47
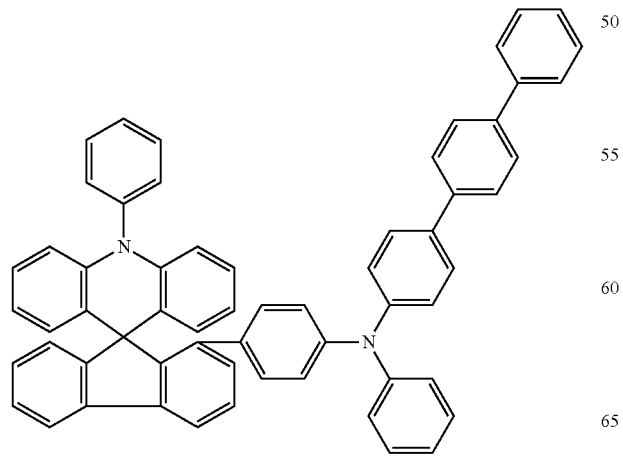
-continued
7-48
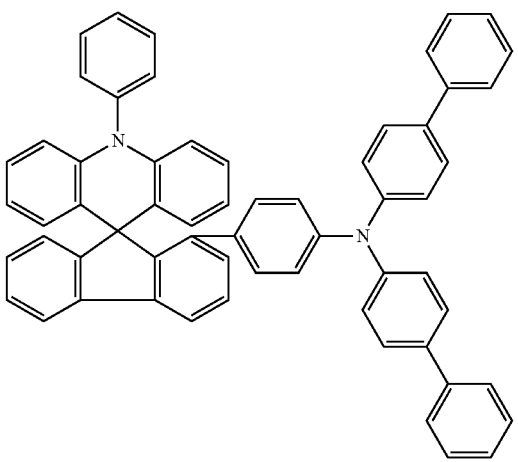
7-49
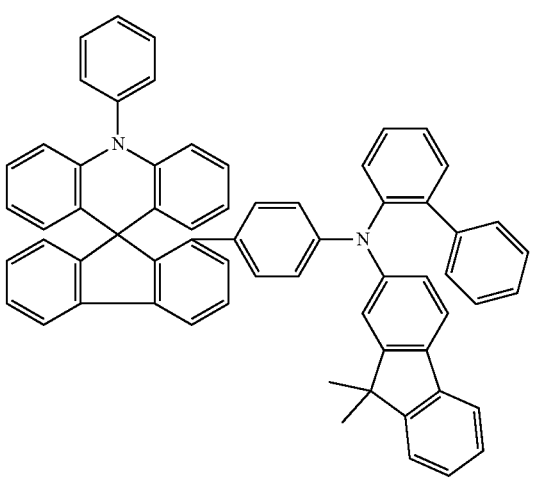
7-50
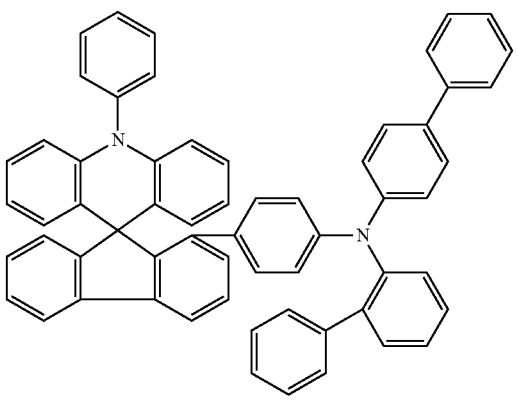

7-51 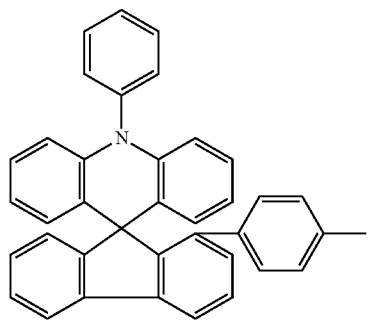
7-52 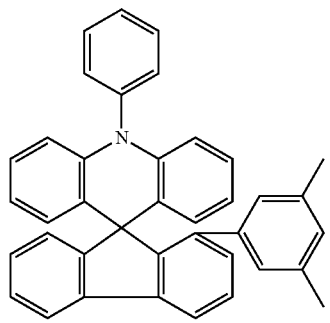
7-53 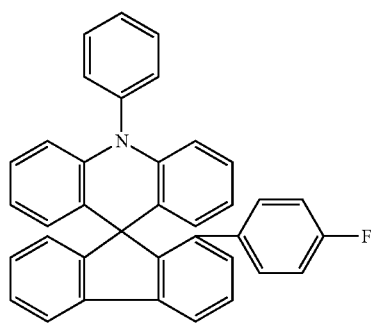
7-54 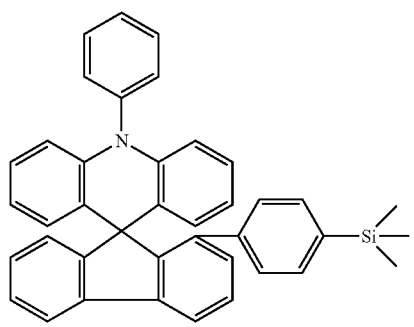
7-55 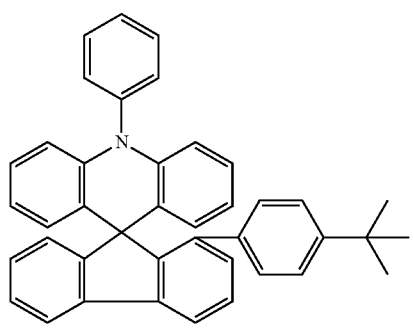
7-56 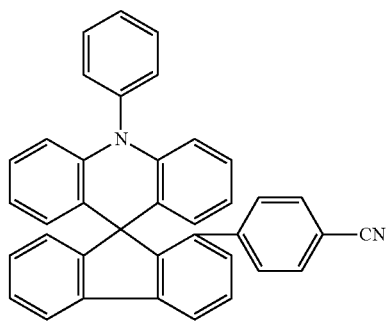
7-57 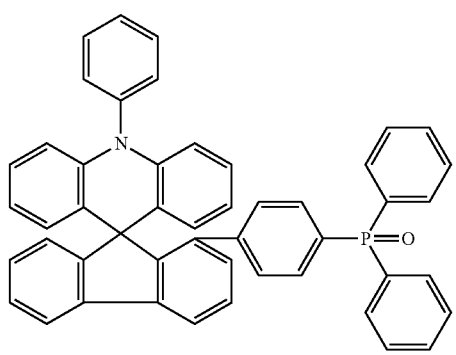
7-58 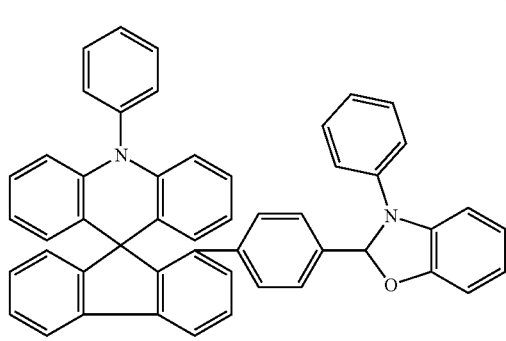
7-59 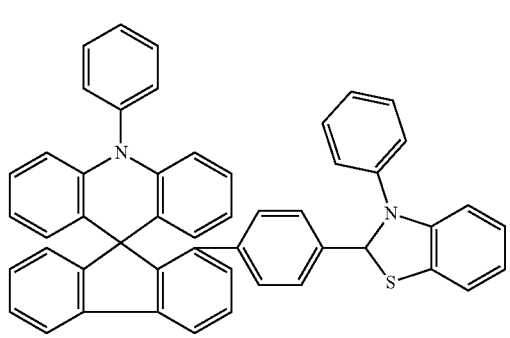

7-60
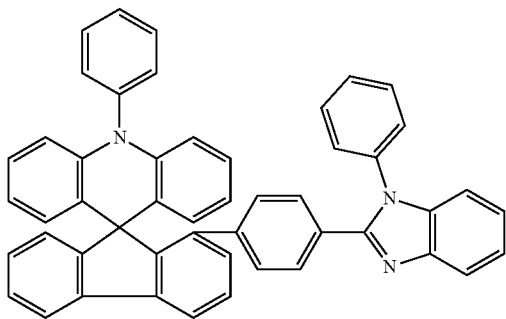
7-64
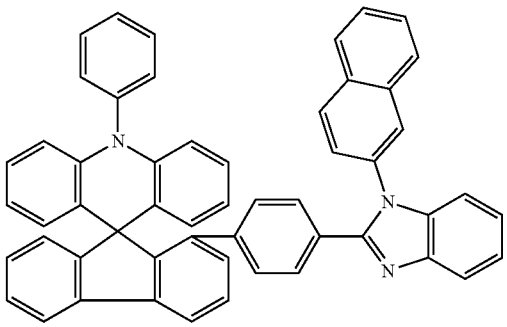
7-61
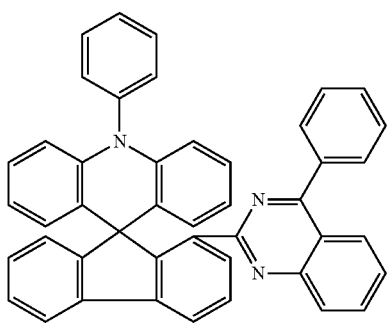
7-65
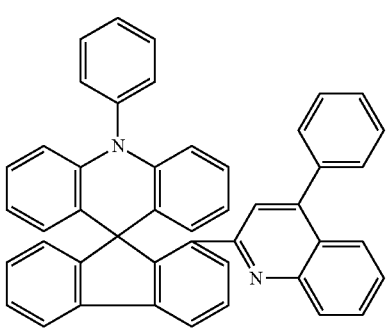
7-62
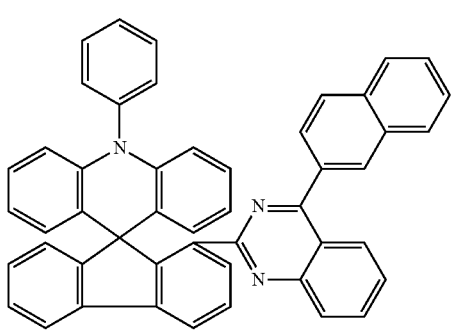
7-66
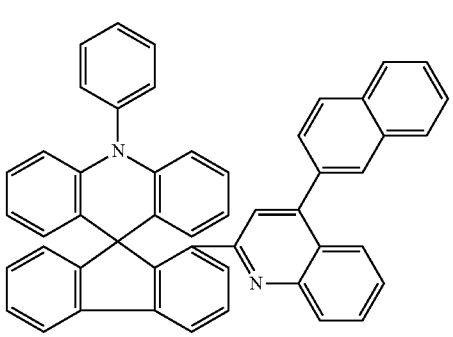
7-63
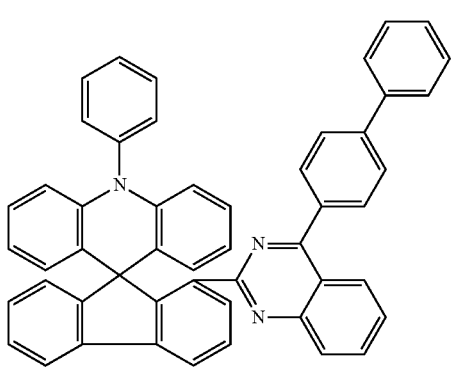
7-67
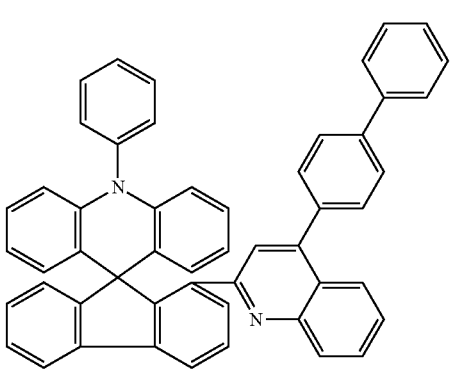

7-68
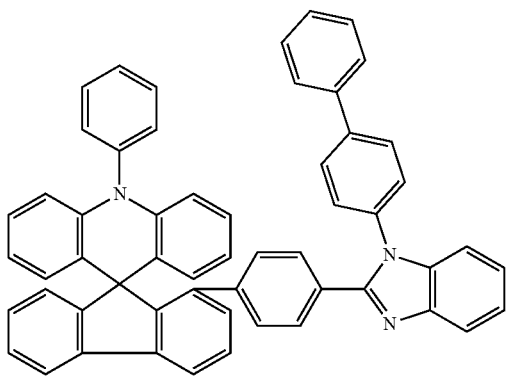
7-72
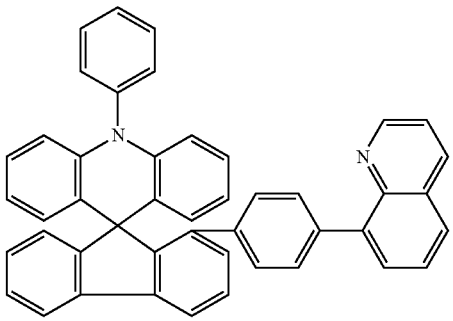
7-69
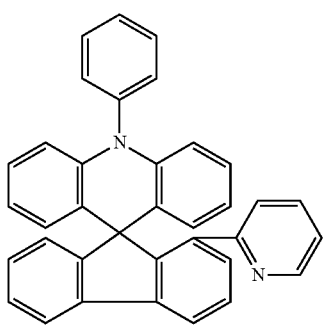
7-73
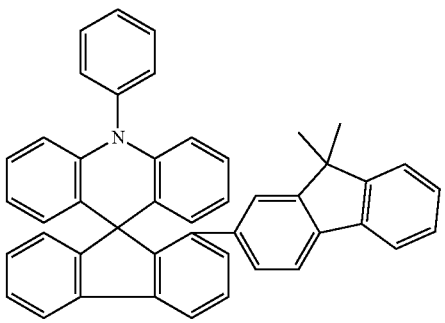
7-70
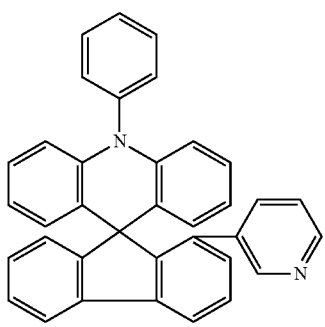
7-74
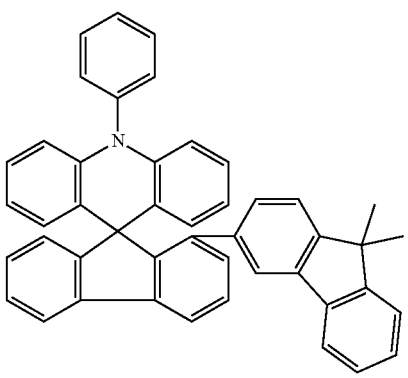
7-71
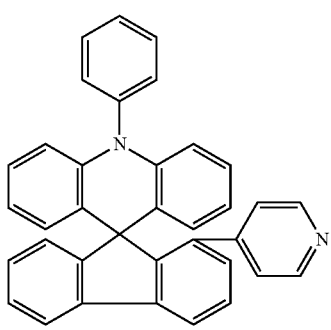
7-75
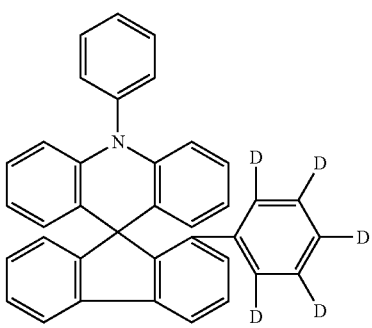

7-76
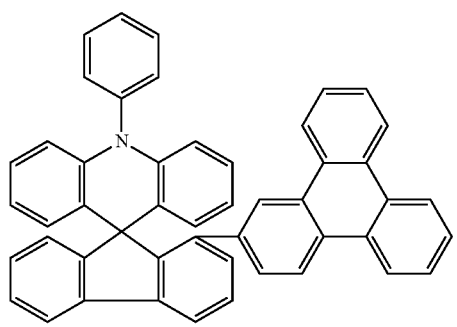
7-80
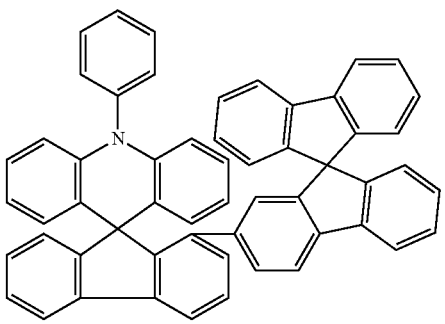
7-77
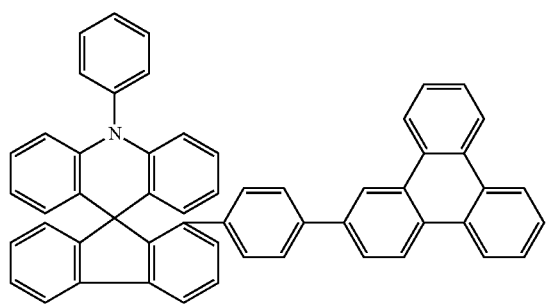
7-81
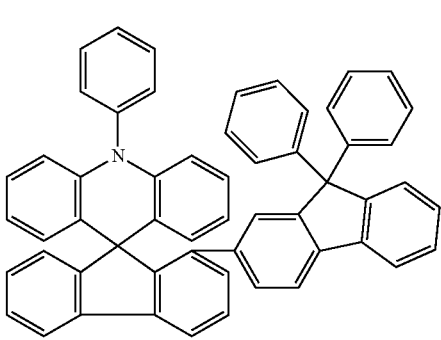
7-78
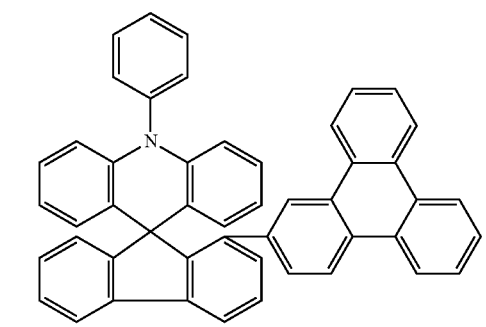
7-82
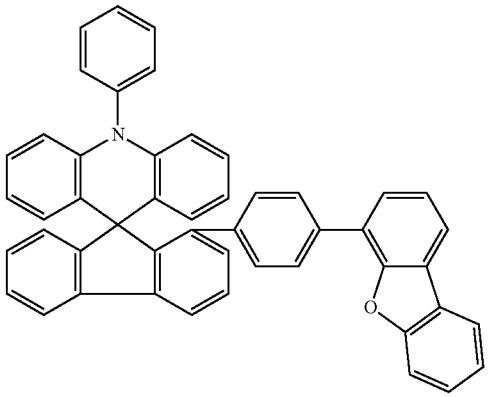
7-79
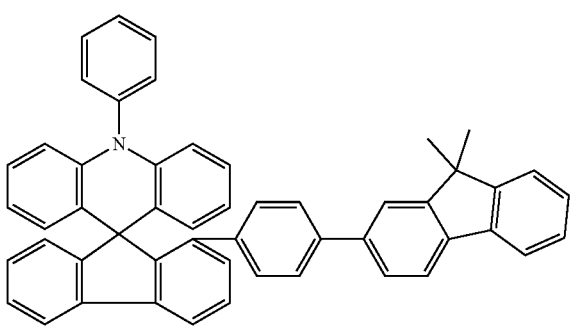
7-83
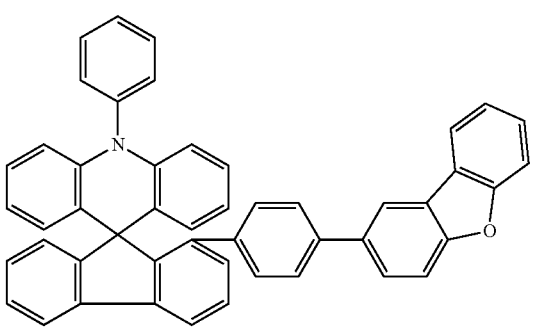

7-84

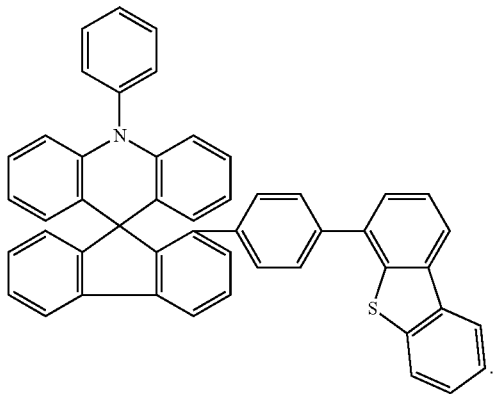

7. An organic light emitting device comprising:
a first electrode;
a second electrode provided to face the first electrode; and
one or more organic material layers provided between the first electrode and the second electrode,
wherein the one or more organic material layers comprise the compound of claim 1.

8. The organic light emitting device of claim 7, wherein the one or more organic material layers comprises a hole transport layer, and the hole transport layer comprises the compound.

9. The organic light emitting device of claim 7, wherein the one or more organic material layers comprises a hole injection layer, and the hole injection layer comprises the compound.

10. The organic light emitting device of claim 7, wherein the one or more organic material layers comprises an electron blocking layer, and the electron blocking layer comprises the compound.

11. The organic light emitting device of claim 7, wherein the one or more organic material layers comprises a layer which injects and transports holes simultaneously, and the layer which injects and transports holes simultaneously comprises the compound.

12. The organic light emitting device of claim 7, wherein the one or more organic material layers comprises a compound represented by the following Chemical Formula 1-A:

[Chemical Formula 1-A]

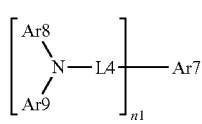

in Chemical Formula 1-A,
n1 is an integer of 1 or more,
Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L4 is a direct bond; a substituted or unsubstituted arylene group; or a substituted or unsubstituted heteroarylene group, Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group; and Ar8 and Ar9 optionally combine with each other via a single bond to form a substituted or unsubstituted ring, and
when n1 is 2 or more, each of L4, Ar8 and Ar9, respectively, is the same as or different from each other.

13. The organic light emitting device of claim 12, wherein L4 is a direct bond, Ar7 is a divalent pyrene group, Ar8 and Ar9 are the same as or different from each other, and are each independently an aryl group having 6 to 30 carbon atoms, which is unsubstituted or substituted with an alkyl group having 1 to 30 carbon atoms, or a substituted or unsubstituted heteroaryl group having 2 to 30 carbon atoms, and n1 is 2.

14. The organic light emitting device of claim 7, wherein the one or more organic material layers comprises a compound represented by the following Chemical Formula 2-A:

[Chemical Formula 2-A]

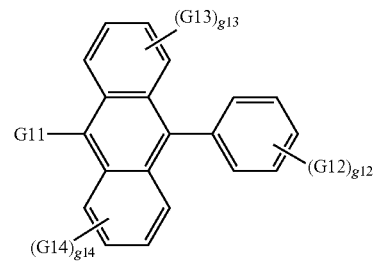

in Chemical Formula 2-A,
G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

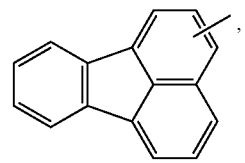

G12 is a phenyl group, a 1-naphthyl group, a 2-naphthyl group, a 1-anthryl group, a 2 anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl- 2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each independently an integer of 1 to 4, and when g12 to g14 are each 2 or more, each of G12, G13 and G14, respectively, is the same as or different from each other.

15. The organic light emitting device of claim 14, wherein G11 is a 1-naphthyl group, and G12 is a 2-naphthyl group.

16. The organic light emitting device of claim 12, wherein the one or more organic material layers comprises a compound represented by the following Chemical Formula 2-A:

[Chemical Formula 2-A]

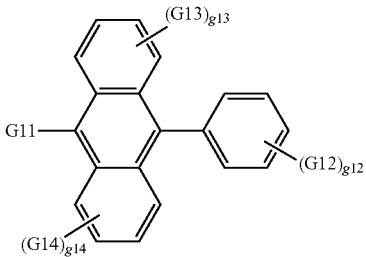

in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

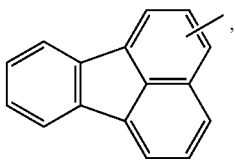

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each independently an integer of 1 to 4, and when g12 to g14 are each 2 or more, each of G12, G13 and G14, respectively, is the same as or different from each other.

17. A display device comprising the organic light emitting device of claim 1.

18. A lighting device comprising the organic light emitting device of claim 1.

* * * * *